US009493540B2

(12) United States Patent
Palli et al.

(10) Patent No.: US 9,493,540 B2
(45) Date of Patent: Nov. 15, 2016

(54) ECDYSONE RECEPTOR/INVERTEBRATE RETINOID X RECEPTOR-BASED INDUCIBLE GENE EXPRESSION SYSTEM

(75) Inventors: Subba Reddy Palli, Lexington, KY (US); Marianna Zinovievna Kapitskaya, Paris (FR)

(73) Assignee: Intrexon Corporation, Blacksburg, VA (US)

( * ) Notice: Subject to any disclaimer, the term of this patent is extended or adjusted under 35 U.S.C. 154(b) by 3821 days.

(21) Appl. No.: 10/468,200

(22) PCT Filed: Feb. 20, 2002

(86) PCT No.: PCT/US02/05235

§ 371 (c)(1), (2), (4) Date: Dec. 15, 2011

(87) PCT Pub. No.: WO02/066613

PCT Pub. Date: Aug. 29, 2002

(65) Prior Publication Data

US 2012/0167239 A1 Jun. 28, 2012

Related U.S. Application Data

(60) Provisional application No. 60/269,799, filed on Feb. 20, 2001, provisional application No. 60/294,814, filed on May 31, 2001.

(51) Int. Cl.

| | |
|---|---|
| ***C12N 15/63*** | (2006.01) |
| ***C12N 5/02*** | (2006.01) |
| ***C07K 14/705*** | (2006.01) |
| ***C07K 14/72*** | (2006.01) |

(52) U.S. Cl.

CPC ....... *C07K 14/70567* (2013.01); *C07K 14/721* (2013.01)

(58) Field of Classification Search

None

See application file for complete search history.

(56) References Cited

U.S. PATENT DOCUMENTS

| | | | |
|---|---|---|---|
| 4,631,211 | A | 12/1986 | Houghten |
| 4,859,609 | A | 8/1989 | Dull et al. |
| 4,954,655 | A | 9/1990 | Kelly |
| 4,981,784 | A | 1/1991 | Evans et al. |
| 4,985,461 | A | 1/1991 | Hsu et al. |
| 5,010,175 | A | 4/1991 | Rutter et al. |
| 5,071,773 | A | 12/1991 | Evans |
| 5,117,057 | A | 5/1992 | Hsu et al. |
| 5,171,671 | A | 12/1992 | Evans et al. |
| 5,225,443 | A | 7/1993 | Murphy et al. |
| 5,283,173 | A | 2/1994 | Fields et al. |
| 5,378,726 | A | 1/1995 | Yanagi et al. |
| 5,424,333 | A | 6/1995 | Wing |
| 5,429,952 | A | 7/1995 | Garner et al. |
| 5,459,127 | A | 10/1995 | Felgner et al. |
| 5,514,578 | A | 5/1996 | Hogness et al. |
| 5,530,021 | A | 6/1996 | Yanagi et al. |
| 5,530,028 | A | 6/1996 | Lidert et al. |
| 5,599,904 | A | 2/1997 | Evans et al. |
| 5,639,616 | A | 6/1997 | Ulm et al. |
| 5,641,652 | A | 6/1997 | Oro et al. |
| 5,668,175 | A | 9/1997 | Evans et al. |
| 5,688,691 | A | 11/1997 | Oro et al. |
| 5,710,004 | A | 1/1998 | Evans et al. |
| 5,723,329 | A | 3/1998 | Mangelsdorf et al. |
| 5,880,333 | A | 3/1999 | Goff et al. |
| 5,919,667 | A | 7/1999 | Gage et al. |
| 5,939,442 | A | 8/1999 | Evans et al. |
| 5,989,863 | A | 11/1999 | Tang et al. |
| 6,013,836 | A | 1/2000 | Hsu et al. |
| 6,025,483 | A | 2/2000 | Yanofsky |
| 6,096,787 | A | 8/2000 | Evans et al. |
| 6,117,639 | A | 9/2000 | Germann et al. |
| 6,147,282 | A | 11/2000 | Goff et al. |
| 6,214,620 | B1 | 4/2001 | Johns et al. |
| 6,245,531 | B1 | 6/2001 | Hogness et al. |
| 6,258,603 | B1 | 7/2001 | Carlson et al. |
| 6,265,173 | B1 | 7/2001 | Evans et al. |
| 6,281,330 | B1 | 8/2001 | Evans et al. |
| 6,300,488 | B1 | 10/2001 | Gage et al. |
| 6,326,166 | B1 | 12/2001 | Pomerantz et al. |
| 6,333,318 | B1 | 12/2001 | Evans et al. |
| 6,379,945 | B1 | 4/2002 | Jepson et al. |
| 6,410,245 | B1 | 6/2002 | Northrop et al. |

(Continued)

FOREIGN PATENT DOCUMENTS

| | | |
|---|---|---|
| CN | 1313276 | 9/2001 |
| EP | 234994 A1 | 1/1987 |

(Continued)

OTHER PUBLICATIONS

Tease et al. (1978) 69: 163-178.*

Holt Jr et al, "Functional expression of exogenous proteins in mammalian sensory hair cells infected with adenoviral vectors." J Neurophysiol. 1999, 81:1881-1888.

Glass CK et al. "Nuclear Receptor Coactivators." Curr Opin Cell Biol. 1997, 9:222-232.

Filmus J et al."Synergistic induction of promoters containing metal- and glucocorticoid-responsive elements."Nucleic Acids Res. Jun. 11, 1992; 20(11): 2755-2760.

(Continued)

*Primary Examiner* — Michael Pak

(74) *Attorney, Agent, or Firm* — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to a novel ecdysone receptor/invertebrate retinoid X receptor-based inducible gene expression system and methods of modulating gene expression in a host cell for applications such as gene therapy, large-scale production of proteins and antibodies, cell-based high throughput screening assays, functional genomics and regulation of traits in transgenic organisms.

27 Claims, 11 Drawing Sheets

(56) References Cited

U.S. PATENT DOCUMENTS

| | | | | |
|---|---|---|---|---|
| 6,458,926 | B1 | 10/2002 | Evans et al. | |
| 6,504,082 | B1 | 1/2003 | Albertsen | |
| 6,635,429 | B1 | 10/2003 | Leid et al. | |
| 6,723,531 | B2 | 4/2004 | Evans et al. | |
| 6,756,491 | B2 | 6/2004 | Evans et al. | |
| 6,875,569 | B2 | 4/2005 | Gage et al. | |
| 6,939,711 | B2 | 9/2005 | Goff et al. | |
| 7,038,022 | B1 | 5/2006 | Evans et al. | |
| 7,045,315 | B2 | 5/2006 | Evans et al. | |
| 7,057,015 | B1 | 6/2006 | Gage et al. | |
| 7,091,038 | B2 * | 8/2006 | Palli | C12N 15/1055 435/320.1 |
| 7,119,077 | B1 | 10/2006 | Evans et al. | |
| 7,183,061 | B2 | 2/2007 | Jepson et al. | |
| 7,456,315 | B2 | 11/2008 | Hormann et al. | |
| 7,531,326 | B2 | 5/2009 | Kapitskaya et al. | |
| 7,563,879 | B2 | 7/2009 | Palli et al. | |
| 7,601,508 | B2 | 10/2009 | Palli et al. | |
| 7,776,587 | B2 | 8/2010 | Palli et al. | |
| 7,807,417 | B2 | 10/2010 | Palli et al. | |
| 7,829,676 | B2 | 11/2010 | Zhang et al. | |
| 7,919,269 | B2 | 4/2011 | Zhang et al. | |
| 7,935,510 | B2 | 5/2011 | Palli et al. | |
| 8,021,878 | B2 | 9/2011 | Palli et al. | |
| 8,030,067 | B2 | 10/2011 | Zhang et al. | |
| 8,076,454 | B2 | 12/2011 | Palli et al. | |
| 8,105,825 | B2 | 1/2012 | Dhadialla et al. | |
| 8,115,059 | B1 | 2/2012 | Palli et al. | |
| 8,168,426 | B2 | 5/2012 | Dhadialla et al. | |
| 8,202,718 | B2 | 6/2012 | Palli et al. | |
| 8,236,556 | B2 | 8/2012 | Kapitskaya et al. | |
| 8,497,093 | B2 | 7/2013 | Palli et al. | |
| 8,598,409 | B2 | 12/2013 | Kapitskaya et al. | |
| 8,669,051 | B2 | 3/2014 | Palli et al. | |
| 8,680,249 | B2 | 3/2014 | Palli et al. | |
| 8,691,527 | B2 | 4/2014 | Palli et al. | |
| 8,715,959 | B2 | 5/2014 | Palli et al. | |
| 8,728,808 | B2 | 5/2014 | Dhadialla et al. | |
| 2002/0037514 | A1 * | 3/2002 | Klein et al. | 435/6 |
| 2002/0110861 | A1 | 8/2002 | Dhadialla et al. | |
| 2002/0119521 | A1 | 8/2002 | Palli et al. | |
| 2004/0033600 | A1 | 2/2004 | Palli et al. | |
| 2004/0096942 | A1 | 5/2004 | Palli et al. | |
| 2004/0197861 | A1 | 10/2004 | Palli et al. | |
| 2004/0235097 | A1 | 11/2004 | Zhang et al. | |
| 2005/0266457 | A1 | 12/2005 | Palli et al. | |
| 2006/0100416 | A1 | 5/2006 | Palli et al. | |
| 2007/0161086 | A1 | 7/2007 | Palli et al. | |
| 2007/0300313 | A1 | 12/2007 | Palli et al. | |
| 2008/0115237 | A1 | 5/2008 | Palli et al. | |
| 2008/0145935 | A1 | 6/2008 | Palli et al. | |
| 2008/0176280 | A1 | 7/2008 | Kapitskaya et al. | |
| 2008/0216184 | A1 | 9/2008 | Palli et al. | |
| 2008/0235816 | A1 | 9/2008 | Dhadialla et al. | |
| 2008/0263687 | A1 | 10/2008 | Kapitskaya et al. | |
| 2008/0301825 | A1 | 12/2008 | Palli et al. | |
| 2010/0275281 | A1 | 10/2010 | Dhadialla et al. | |
| 2011/0059525 | A1 | 3/2011 | Palli et al. | |
| 2011/0059530 | A1 | 3/2011 | Palli et al. | |
| 2012/0167239 | A1 | 6/2012 | Palli et al. | |
| 2012/0185954 | A1 | 7/2012 | Palli et al. | |
| 2012/0322148 | A1 | 12/2012 | Palli et al. | |
| 2013/0117872 | A1 | 5/2013 | Palli et al. | |
| 2013/0232588 | A1 | 9/2013 | Kapitskaya et al. | |
| 2013/0244330 | A1 | 9/2013 | Palli et al. | |
| 2013/0267023 | A1 | 10/2013 | Dhadialla et al. | |
| 2013/0286156 | A1 | 10/2013 | Dhadialla et al. | |

FOREIGN PATENT DOCUMENTS

| | | | |
|---|---|---|---|
| EP | 461809 | A1 | 6/1991 |
| EP | 798378 | B1 | 3/1997 |
| EP | 965644 | A2 | 6/1999 |
| EP | 965 644 | A2 | 12/1999 |
| EP | 1266015 | B1 | 3/2001 |
| WO | WO8912690 | A1 | 6/1989 |
| WO | WO9200252 | A1 | 1/1992 |
| WO | WO9428028 | A1 | 5/1994 |
| WO | WO9518863 | A1 | 1/1995 |
| WO | WO9521931 | A1 | 1/1995 |
| WO | WO9625508 | A1 | 2/1996 |
| WO | 9637609 | A1 | 5/1996 |
| WO | WO9617823 | A1 | 6/1996 |
| WO | 9627673 | A1 | 9/1996 |
| WO | 9735985 | A1 | 3/1997 |
| WO | 9738117 | A1 | 10/1997 |
| WO | 9833162 | A2 | 1/1998 |
| WO | WO 98/35550 | A2 | 8/1998 |
| WO | 9902683 | A1 | 1/1999 |
| WO | WO9936520 | A1 | 1/1999 |
| WO | 9910510 | A2 | 3/1999 |
| WO | 9951777 | A2 | 4/1999 |
| WO | 9951777 | A3 | 4/1999 |
| WO | 9927365 | A1 | 6/1999 |
| WO | WO 99/26966 | A2 | 6/1999 |
| WO | 9910510 | A3 | 7/1999 |
| WO | 9936520 | A1 | 7/1999 |
| WO | 9958155 | A1 | 11/1999 |
| WO | 0071743 | | 11/2000 |
| WO | WO 01/02436 | A1 | 1/2001 |
| WO | 0136447 | | 3/2001 |
| WO | WO0170816 | A2 | 3/2001 |
| WO | 0162780 | | 8/2001 |
| WO | WO0266612 | A2 | 2/2002 |
| WO | WO0266613 | A2 | 2/2002 |
| WO | WO0266614 | A2 | 2/2002 |
| WO | WO0266615 | A2 | 2/2002 |
| WO | WO0229075 | A2 | 4/2002 |
| WO | 03105849 | A1 | 6/2003 |
| WO | WO03105489 | A1 | 6/2003 |
| WO | WO2004005478 | A2 | 1/2004 |
| WO | WO2004072254 | A2 | 2/2004 |
| WO | WO2004078924 | A2 | 2/2004 |
| WO | WO2005017126 | A2 | 2/2005 |
| WO | WO2006083253 | A1 | 2/2005 |
| WO | WO2005108617 | A2 | 5/2005 |

OTHER PUBLICATIONS

Fields S et al. "A novel genetic system to detect protein-protein interactions." Nature 1989, 340:245-246.

Doyle DF et al."Engineering orthogonal ligand-receptor pairs from near drugs." J Am Chem Soc. Nov. 21, 2001;123 (46):11367-71.

Carlson GR et al. "The chemical and biological properties of methoxyfenozide, a new insecticidal ecdysteroid agonist." Pest Manag Sci. Feb. 2001;57(2):115-9.

Cao S et al. "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis." Canadian Journal of Chemistry, Mar. 2001 , 79(3):272-278.

Belshaw PJ et al. "Rational Design of Orthogonal Receptor-Ligand Combinations." Angewandte Chemie. International edition in English (Angew. Chem., Int. ed. Engl.) 1995, vol. 34, No. 19, pp. 2129-2132.

Belshaw PJ et al."Controlling Protein Association and Subcellular Localization with a Synthetic Ligand that Induces Heterodimerization of Proteins." Proc Natl Acad Sci. 1996, 93:4604-7.

Andrianov VG et al. "4-Aminofurazan-3-hydroximic halides." Chemistry of Heterocyclic Compounds 1992, 28(5):581-585.

Andrianov VG et al. "4-Amino-δ2-1,2,4-oxadiazolines." Chemistry of Heterocyclic Compounds 1991, 22(2):216-218.

Brennan JD. "Preparation and Entrapment of Fluorescently Labeled Proteins for the Development of Reagentless Optical Biosensors." Journal of Fluorescence, Dec. 1999, 9(4): 295-312.

Hoppe UC et al. "Adenovirus-mediated Inducible Gene Expression in Vivo by Hybrid Ecdysone Receptor." Mol Therapy 2000 1(2):159-164.

Horwitz KB et al. "Nuclear receptor coactivators and corepressors." Mol Endocrinol. Oct. 1996; 10(10):1167-77.

Kim JS et al."Design of TATA box-binding protein/zinc finger fusions for targeted regulation of gene expression." Proc Natl Acad Sci U S A. Apr. 15, 1997;94(8):3616-20.

(56) References Cited

OTHER PUBLICATIONS

Kirken RA et al. "Two discrete regions of interleukin-2 (IL2) receptor beta independently mediate IL2 activation of a PD98059/rapamycin/wortmannin-insensitive Stat5a/b serine kinase." J Biol Chem. Jun. 13, 1997;272(24):15459-65.
Nakagawa Y et al. "Quantitative structure-activity studies of insect growth regulators: XIX. Effects of substituents on the aromatic moiety of dibenzoylhydrazines on larvicidal activity against the beet armyworm Spodoptera exigua." Pest Manag Sci. Feb. 2002;58(2):131-8.
O'Brien RN et al. "Structural and functional analysis of the human phosphoenolpyruvate carboxykinase gene promoter." Biochim Biophys Acta. Dec. 27, 1995;1264(3):284-8.
Peet DJ et al."Engineering novel specificities for ligand-activated transcription in the nuclear hormone receptor RXR." Chem Biol. Jan. 1998;5(1):13-21.
Pierce AC et al."Computational Binding Studies of Orthogonal Cyclosporin-Cyclophilin Pairs." Angewandte Chemie. International edition in English (Angew. Chem., Int. ed. Engl.) 1997, vol. 36, No. 13-14, pp. 1466-1469.
Spencer DM et al. "Controlling signal transduction with synthetic ligands." Science. Nov. 12, 1993;262(5136):1019-24.
Trisyono A et al. "Effect of Nonsteroidal ecdysone agonists, methoxyfenozide and tebufenozide, on the European Corn Borer (Lepidoptera: Pyralidae)." J Economic Entomology 1997, 90:1486-1492.
Wurm FM et al. "Inducible overproduction of the mouse c-myc protein in mammalian cells." Proc Natl Acad Sci U S A. 1986, 83(15):5414-8.
Wipf P, et al. "Combinatorial synthesis and biological evaluation of library of small-molecule Ser/Thr-protein phosphatase inhibitors." Bioorg Med Chem. 1997, 5(1):165-77.
Wing KD et al. "RH 5849, a Nonsteroidal Ecdysone Agonist: Effects on Larval Lepidoptera." Science. 1988, 241 (4864):470-472.
Zhang X et al."Study on synthesis and bioactivity of new diacylhydrazine IGR JS1 18." Nongyao 2003, 42:18-20.
Antoniewski C et al., The ecdysone response enhancer of the Fbp1 gene of *Drosophila melanogaster* is a direct target for the EcR/USP nuclear receptor, Mol Cell Biol, (1994), 14:4465-74.
Ashburner M et al., Temporal control of puffing activity in polytene chromosomes, Cold Spring Herb Symp Quant Biol, (1974), 38:655-62.
Cherbas L et al., Identification of ecdysone response elements by analysis of the *Drosophila* Eip28/29 gene, Genes Dev, (1991), 5:120-31.
Cho WL et al., Mosquito ecdysteroid receptor: analysis of the cDNA and expression during vitellogenesis, Insect Biochem Mol Biol, (1995), 25:19-27.
Chung AC et al., Cloning of crustacean ecdysteroid receptor and retinoid-X receptor gene homologs and elevation of retinoid-X receptor mRNA by retinoic acid, Mol Cell Endocrinol, (1998), 139:209-27.
D'Avino PP et al., The moulting hormone ecdysone is able to recognize target elements composed of direct repeats, Mol Cell Endocrinol, (1995), 113:1-9.
Dhadialla TS et al., New insecticides with ecdysteroidal and juvenile hormone activity, Annu Rev Entomol, (1998), 43:545-69.
Evans RM, The steroid and thyroid hormone receptor superfamily, Science, (1988), 240:889-95.
Fujiwara H et al., Cloning of an ecdysone receptor homolog from Manduca sexta and the developmental profile of its mRNA in wings, Insect Biochem Mol Biol, (1995), 25:845-56.
Godowski PJ et al., Signal transduction and transcriptional regulation by glucocorticoid receptor-LexA fusion proteins, Science, (1988), 241:812-6.
Guo X et al., Isolation of a functional ecdysteroid receptor homologue from the ixodid tick Amblyomma americanum (L.), Insect Biochem Mol Biol, (1997), 27:945-62.
Hannan GN et al., Cloning and characterization of LcEcR: a functional ecdysone receptor from the sheep blowfly Lucilia cuprina, Insect Biochem Mol Biol, (1997), 27:479-88.
Heberlein U et al., Characterization of *Drosophila* transcription factors that activate the tandem promoters of the alcohol dehydrogenase gene, Cell, (1985), 41:965-77.
Imhof Mo et al., Cloning of a Chironomus tentans cDNA encoding a protein (cEcRH) homologous to the *Drosophila melanogaster* ecdysteroid receptor (dEcR), Insect Biochem Mol Biol, (1993), 23:115-24.
Kothapalli R et al., Cloning and developmental expression of the ecdysone receptor gene from the spruce budworm, Choristoneura furniferana, Dev Genet, (1995), 17:319-30.
Licitra EJ et al., A three-hybrid system for detecting small ligand-protein receptor interactions, Proc Natl Acad Sci U S A, (1996), 93:12817-21.
Martinez A et al., Transcriptional activation of the cloned Heliothis virescens (Lepidoptera) ecdysone receptor (HvEcR) by muristeroneA, Insect Biochem Mol Biol, (1999), 29:915-30.
Morrison DA et al., Isolation of transformation-deficient *Streptococcus* pneumoniae mutants defective in control of competence, using insertion-duplication mutagenesis with the erythromycin resistance determinant of pAM beta 1, J Bacteriol, (1984), 159:870-6.
Mouillet JF et al., Cloning of two putative ecdysteroid receptor isoforms from Tenebrio molitor and their developmental expression in the epidermis during metamorphosis, Eur J Biochem, (1997), 248:856-63.
Neuberger MS et al., Recombinant antibodies possessing novel effector functions, Nature, (1984), 312:604-8.
Riddiford LM et al., Ecdysone receptors and their biological actions, Vitam Horm, (2000), 60:1-73.
Saleh DS et al., Cloning and characterization of an ecdysone receptor cDNA from Locusta migratoria, Mol Cell Endocrinol, (1998), 143:91-9.
Srini C. Perera MSPJKARTSDSRP, An analysis of ecdysone receptor domains required for heterodirnerization with ultraspiracle, Archives of Insect Biochemistry and Physiology, (1999), 41:61-70.
Suhr ST et al., High level transactivation by a modified Bombyx ecdysone receptor in mammalian cells without exogenous retinoid X receptor, Proc Natl Acad Sci U S A, (1998), 95:7999-8004.
Swevers L et al., The silkmoth homolog of the *Drosophila* ecdysone receptor (B1 isoform): cloning and analysis of expression during follicular cell differentiation, Insect Biochem Mol Biol, (1995), 25:857-66.
Verras M et al., Cloning and characterization of CcEcR. An ecdysone receptor homolog from the mediterranean fruit fly Ceratitis capitata, Eur J Biochem, (1999), 265:798-808.
Wilson JM et al., Hepatocyte-directed gene transfer in vivo leads to transient improvement of hypercholesterolemia in low density lipoprotein receptor-deficient rabbits, J Biol Chem, (1992), 267:963-7.
Yao TP et al., *Drosophila* ultraspiracle modulates ecdysone receptor function via heterodimer formation, Cell, (1992), 71:63-72.
Yao TP et al., Functional ecdysone receptor is the product of EcR and Ultraspiracle genes, Nature, (1993), 366:476-9.
Christopherson KS et al., Ecdysteroid-dependent regulation of genes in mammalian cells by a *Drosophila* ecdysone receptor and chimeric transactivators, Proc Natl Acad Sci U S A, (1992), 89:6314-8.
Kakizawa T et al., Ligand-dependent heterodimerization of thyroid hormone receptor and retinoid X receptor, J Biol Chem, (1997), 272:23799-804.
Koelle Mr et al., The *Drosophila* EcR gene encodes an ecdysone receptor, a new member of the steroid receptor superfamily, Cell, (1991), 67:59-77.
Leid M et al., Purification, cloning, and RXR identity of the HeLa cell factor with which RAR or TR heterodimerizes to bind target sequences efficiently, Cell, (1992), 68:377-95.
Leonhardt SA et al., Agonist and antagonists induce homodimerization and mixed ligand heterodimerization of human progesterone receptors in vivo by a mammalian two-hybrid assay, Mol Endocrinol, (1998), 12:1914-30.

(56) References Cited

OTHER PUBLICATIONS

Metzger D et al., The human oestrogen receptor functions in yeast, Nature, (1988), 334:31-6.
No D et al., Ecdysone-inducible gene expression in mammalian cells and transgenic mice, Proc Natl Acad Sci U S A, (1996), 93:3346-51.
Perera SC et al., Studies on two ecdysone receptor isoforms of the spruce budworm, Choristoneura fumiferana, Mol Cell Endocrinol, (1999), 152:73-84.
Office Action mailed Jun. 13, 2005 in U.S. Appl. No. 09/965,703, inventors Palli, et al., filed on Sep. 26, 2001.
Office Action mailed Nov. 24, 2004 in U.S. Appl. No. 09/965,703, inventors Palli, et al., filed on Sep. 26, 2001.
Office Action mailed May 14, 2004 in U.S. Appl. No. 09/965,703, inventors Palli, et al., filed on Sep. 26, 2001.
Office Action mailed Sep. 19, 2007 in U.S. Appl. No. 10/468,193, inventors Palli, et al., filed on Dec. 17, 2003.
Office Action mailed Dec. 9, 2008 in U.S. Appl. No. 09/965,697, inventors Dhadialla, et al., filed on Sep. 27, 2001.
Office Action mailed May 28, 2008 in U.S. Appl. No. 09/965,697, inventors Dhadialla, et al., filed on Sep. 27, 2001.
Office Action mailed Aug. 9, 2007 in U.S. Appl. No. 09/965,697, inventors Dhadialla, et al., filed on Sep. 27, 2001.
Office Action mailed Nov. 13, 2006 in U.S. Appl. No. 09/965,697, inventors Dhadialla, et al., filed on Sep. 27, 2001.
Office Action mailed Apr. 18, 2006 in U.S. Appl. No. 09/965,697, inventors Dhadialla, et al., filed on Sep. 27, 2001.
Office Action mailed Jul. 12, 2005 in U.S. Appl. No. 09/965,697, inventors Dhadialla, et al., filed on Sep. 27, 2001.
Office Action delivered electronically Aug. 21, 2008 in U.S. Appl. No. 11/677,968, inventors Palli, et al., filed on Feb. 22, 2007.
Office Action mailed Mar. 13, 2008 in U.S. Appl. No. 10/468,199, inventors Kapitskaya, et al., filed on Dec. 17, 2003.
Office Action mailed Jun. 11, 2007 in U.S. Appl. No. 10/468,199, inventors Kapitskaya, et al., filed on Dec. 17, 2003.
Office Action mailed Oct. 26, 2006 in U.S. Appl. No. 10/468,199, inventors Kapitskaya, et al., filed on Dec. 17, 2003.
Office action mailed Aug. 22, 2006 in U.S. Appl. No. 10/239,134, inventors Palli et al., filed Sep. 19,2002.
Office Action mailed Feb. 20, 2009 in U.S. Appl. No. 11/677,968, inventors Palli et al., filed on Feb. 22, 2007.
Office Action mailed Feb. 25, 2009 in U.S. Appl. No. 11/841,325, inventors Dhadialla et al., filed on Aug. 20, 2007.
Office Action mailed Feb. 24, 2009 in U.S. Appl. No. 11/841,495, inventors Palli et al., filed on Aug. 20, 2007.
Office Action mailed Apr. 2, 2009 in U.S. Appl. No. 11/841,529, inventors Palli et al., filed on Aug. 20, 2007.
U.S. Appl. No. 09/965,697, inventors Dhadialla, et al., filed Sep. 27, 2001, published as US 2002/0110861 A1.
U.S. Appl. No. 11/841,631, inventors Palli, et al. , filed Aug. 20, 2007.
U.S. Appl. No. 10/468,192, inventors Palli, et al., filed Aug. 15, 2003.
U.S. Appl. No. 10/468,193, inventors Palli, et al., filed Dec. 17, 2003, published as US 2006/0100416 A1.
U.S. Appl. No. 10/468,199, inventors Kapitskaya, et al., filed Dec. 17, 2003, published as US 2004/0096942 A1.
U.S. Appl. No. 11/841,529, inventors Palli, et al., filed Aug. 20, 2007, published as US 2007/0300313 A1.
U.S. Appl. No. 11/841,464, inventors Palli, et al., filed Aug. 20, 2007, published as US 2008/0145935 A1.
U.S. Appl. No. 11/841,495, inventors Palli, et al., filed Aug. 20, 2007, published as 2008/0115237 A1.
U.S. Appl. No. 11/841,597, inventors Kapitskaya, et al., filed Aug. 20, 2007, published as US 2008/0176280 A1.
U.S. Appl. No. 11/841,631, inventors Palli, et al., filed Aug. 20, 2007, published as US 2008/0216184 A1.
U.S. Appl. No. 11/841,644, inventors Palli, et al., filed Aug. 20, 2007, published as US 2008/0301825 A1.
U.S. Appl. No. 11/841,325, inventors Dhadialla, et al., filed Aug. 20, 2007, published as US 2008/0235816 A1.
U.S. Appl. No. 11/841,648, inventors Kapitskava, et al., filed Aug. 24, 2007, published as US 2008/0263687 A1.
U.S. Appl. No. 11/677,968, inventors Palli, et al., filed Feb. 22, 2007, published as US 2007/0161086 A1.
U.S. Appl. No. 11/841,464, inventors Palli, et al., filed Aug. 20, 2007.
Hayward, D.C., et al., "The sequence of *Locust* RXR, homologous to *Drosophila* Ultraspiracle, and its evolutionary implications," *Development Genes and Evolution* 209: 564-571, Springer Berlin/ Heidelberg (1999).
Helmreich E.J.M., "The Biochemistry of Cell Signalling," p. 192, Oxford University Press (2001).
Hofmann, A. et al., "Rapid retroviral delivery of tetracycline-inducible genes in a single autoregulatory cassette," *Proc. Natl. Acad. Sci. USA* 93: 51855190, National Academy of Sciences (1996).
Perera, S.C. et al., "An Analysis of Ecdysone Receptor Domains Required for Heterodimerization With Ultraspiracle," *Archives of Insect Biochemistry and Physiology* 41: 61-70, Wiley-Liss, Inc. (1999).
Shimizu, B-i. et al., "Molting hormonal and larvicidal activities of aliphatic acyl analogs of dibenzoylhydrazine insecticides," *Steroids* 62:638-642, Elsevier Science Inc. (1997).
Talbot, W.S., et al., "*Drosophila* Tissues with Different Metamorphic Responses to Ecdysone Express Different Ecdysone Receptor Isoforms," *Cell* 73:1323-1337, Cell Press (1993).
UniProtKB/Swiss-Protein Database, Accession No. P49880, "Ecdysone receptor," 2 pages (1996).
UniProtKB/Swiss-Protein Database, Accession No. P49883, "Ecdysone receptor," 2 pages (1996).
Examiner's SCORE Search Results for U.S. Appl. No. 11/118,855, inventors Palli et al., filed Apr. 28, 2005, 27 pages (conducted on Aug. 14, 2007).
Examiner's SCORE Search Results for U.S. Appl. No. 11/118,855, inventors Palli et al., filed Apr. 28, 2005, 17 pages (conducted on Aug. 14, 2007).
U.S. Appl. No. 13/613,597, inventors Dhadialla et al., filed Sep. 13, 2012.
U.S. Appl. No. 13/618,693, inventors Palli et al., filed Sep. 13, 2012.
U.S. Appl. No. 13/618/693, inventors Palli et al., filed Sep. 13, 2012.
U.S. Application No. 13/618,742, inventors Kapitskaya et al., filed Sep. 14, 2012.
U.S. Appl. No. 13/431,636, inventors Dhadialla et al., filed Mar. 27, 2012.
Palmer, M.J. et al., "*Amblyomma americanum* retinoid X receptor (RXR1) mRNA complete cds.," Genebank Accession No. AF035577 (2000), downloaded from ncbi.nlm.nih/gov/nuccore/ AF035577 on Apr. 26, 2013.
Palmer, M.J. et al., "*Amblyomma americanum* retinoid X receptor (RXR2) mRNA, complete cds.," Genebank Accension No. AF035578 (2000), downloaded from ncbi.nlm.nih/gov/nuccore/ AF035578 Apr. 26, 2013.
Palmer, M.J. et al , "retinoid X receptor (*Amblyomma americanum*)," Genebank Accession No. AAC15588 (2000), downloaded from ncbi.nlm.nih/gov/nuccore/AAC15588 on Apr. 26, 2013.
Palmer, M.J. et al., "retinoid X receptor (*Amblyomma americanum*)," Genebank Accession No. AAC15589 (2000), downloaded from ncbi.nlm.nih/gov/nuccore/AAC15588 on Apr. 26, 2013.
Nicolai, M., "*Tenebrio molitor* mRNA for USP protein (usp gene)," Genebank Accession No. AJ251542 (2000), downloaded from ncbi.nlm.nih/gov/nuccore/AJ251542 on Apr. 26, 2013.
Nicolai, M., "USP protein (*Tenebrio molitor*)," Genebank Accession No. CAB75361 (2000), downloaded from ncbi.nlm.nih/gov/nuccore/CAB75361 on Apr. 26, 2013.
Hayward, D.C., "RXR [*Locusta migratoria*]," Genebank Accession No. AAF00981 (1999), downloaded from ncbi.nlm.nih/gov/nuccore/AAF00981 on Apr. 26, 2013.
Blumberg, B., et al., "Multiple retinoid-responsive receptors in a single cell: Families of retinoid "X" receptors and retinoic acid

(56) References Cited

OTHER PUBLICATIONS receptors in the *Xenopus* egg," *Proc. Natl. Acad. Sci. USA* 89:2321-2325, National Academy of Sciences, United States (1992).
Clayton, G.M., et al., "The structure of the ultraspiracle ligand-binding domain reveals a nuclear receptor locked in an inactive conformation," *Proc. Natl. Acad. Sci.* 98:1549-1554, National Academy of Sciences, United States (2001).
Laudet, V., et al., "A Unified Nomenclature System for the Nuclear Receptor Superfamily," *Cell* 97:161-163, Cell Press, United States (1999).
Mangelsdorf, D.J., et al., "Nuclear receptor that identifies a novel retinoic acid response pathway," *Nature* 345:224-229, Nature Publishing Group, England (1990).
Marklew, S., et al., "Isolation of a novel RXR from Xenopus that most closely resembles mammalian RXRβand is expressed throughout early development," *Biochim Biophys Acta* 1218:267-272, Elsevier Science B.V., Netherlands (1994).
Martinez et al., "Creation of ecdysone receptor chimeras in plants for controlled regulation of gene expression," *Molec. General Genetics* 261:546-552, Springer-Verlag, United States (1999).
Palmer, M.J., et al., "Characterization of EcR and RXR Homologous in the Ixodid Tick, *Amblyomma amerianum* (L.)," *Am. Zool.* 39:747-757, American Society of Zoologists, United States (1999).
Perera, S.C. et al., "Studies on two ecdysone receptor isoforms of the spruce budworm, *Choristoneura fumiferana*," *Molec. Cell. Endocrinol.* 152: 73-84, Elsevier (1999).
Kumar, M.B., "A single point mutation in ecdysone receptor leads to increased ligand specificity: Implications for gene switch applications," *Proc. Natl. Acad. Sci.* 99: 14710-14715, National Academy of Sciences, United States (2002).
Palli, S.R. et al., "Improved ecdysone receptor-based inducible gene regulation system," *Eur. J. Biochem.* 270: 1308-1315, Wiley Interscience (2003).
Tran, H.T. et al., "Reconstruction of Ligand-Dependent Transactivation of *Choristoneura fumiferana* Ecdysone Receptor in Yeast," *Molecular Endocrinology* 15: 1140-1153, The Endocrine Society (2001).
Office Action mailed Jun. 30, 2009 in U.S. Appl. No. 11/118,855, inventors Palli et al., filed Apr. 20, 2005.
Office Action mailed Sep. 7, 2007 in U.S. Appl. No. 11/118,855, inventors Palli et al., filed Apr. 20, 2005.
Office Action mailed Sep. 28, 2010 in U.S. Appl. No. 11/841,631, inventors Palli et al., filed Aug. 20, 2007.
Office Action mailed May 12, 2010 in U.S. Appl. No. 11/841,464, inventors Palli et al., filed Aug. 20, 2007.
Office Action mailed Oct. 31, 2012 in U.S. Appl. No. 11/841,464, inventors Palli et al., filed Aug. 20, 2007.
Office Action mailed Sep. 5, 2012 in U.S. Appl. No. 13/289,127, inventors Palli et al., filed Nov. 4, 2011.
Office Action mailed Apr. 16, 2013 in U.S. Appl. No. 13/289,127, inventors Palli et al., filed Nov. 4, 2011.
Office Action mailed Feb. 18, 2010 in U.S. Appl. No. 10/468,193, inventors Palli et al., filed Dec. 17, 2003.
Office Action mailed Jun. 21, 2011 in U.S. Appl. No. 10/468,193, inventors Palli et al., filed Dec. 17, 2003.
Office Action mailed May 10, 2012 in U.S. Appl. No. 10/468,193, inventors Palli et al., filed Dec. 17, 2003.
Office Action mailed Nov. 29, 2012 in U.S. Appl. No. 10/468,193, inventors Palli et al., filed Dec. 17, 2003.
Office Action mailed Sep. 14, 2010 in U.S. Appl. No. 11/841,644, inventors Palli et al., filed Aug. 20, 2007.
Office Action mailed Feb. 14, 2012 in U.S. Appl. No. 11/841,644, inventors Palli et al., filed Aug. 20, 2007.
Office action mailed Jun. 29, 2009 in U.S. Appl. No. 11/841,648, inventors Kapitskaya et al., filed Aug. 24, 2007.
Office action mailed Mar. 22, 2010 in U.S. Appl. No. 11/841,648, inventors Kapitskaya et al., filed Aug. 24, 2007.
Office action mailed Dec. 7, 2010 in U.S. Application No. 11/841,648, inventors Kapitskaya et al., filed Aug. 24, 2007.
Office action mailed Aug. 9, 2011 in U.S. Appl. No. 11/841,648, inventors Kapitskaya et al., filed Aug. 24, 2007.
Office action mailed Jun. 5, 2012 in U.S. Appl. No. 11/841,648, inventors Kapitskaya et al., filed Aug. 24, 2007.
Office action mailed Dec. 10, 2012 in U.S. Appl. No. 11/841,648, inventors Kapitskaya et al., filed Aug. 24 ,2007.
Office Action mailed Apr. 1, 2010 in U.S. Appl. No. 11/841,529, inventors Palli et al., filed Aug. 20, 2007.
Office Action mailed Oct. 21, 2009 in U.S. Appl. No. 11/841,597, inventors Kapitskaya et al., filed Aug. 20, 2007.
Office Action mailed Apr. 20, 2010 in U.S. Appl. No. 11/841,597, inventors Kapitskaya et al., filed Aug. 20, 2007.
Office action mailed Nov. 10, 2010 in U.S. Appl. No. 11/841,597, inventors Kapitskaya et al., filed Aug. 20, 2007.
Office action mailed Nov. 3, 2011 in U.S. Appl. No. 11/841,597, inventors Kapitskaya et al., filed Aug. 20, 2007.
Office action mailed Mar. 30, 2011 in U.S. Appl. No. 12/818,034, inventors Palli et al, filed Jun. 17, 2010.
Office action mailed Oct. 18, 2011 in U.S. Appl. No. 12/818,034, inventors Palli et al., filed Jun. 17, 2010.
Office action mailed Jul. 27, 2012 in U.S. Appl. No. 12/859,940, inventors Palli et al., filed Aug. 20, 2010.
Office action mailed Dec. 28, 2012 in U.S. Appl. No. 12/859,940, inventors Palli et al., filed Aug. 20, 2010.
Office Action mailed Jun. 23, 2009 in U.S. Appl. No. 09/965,697, inventors Dhadialla, et al., filed on Sep. 27, 2001.
Office Action mailed May 25, 2010 in U.S. Appl. No. 09/965,697, inventors Dhadialla, et al., filed on Sep. 27, 2001.
Office Action mailed Feb. 15, 2011 in U.S. Appl. No. 09/965,697, inventors Dhadialla, et al., filed on Sep. 27, 2001.
Office action mailed Dec. 30, 2010 in U.S. Appl. No. 12/707,599, inventors Dhadialla et al., filed Feb. 17, 2010.
Office action mailed Jul. 20, 2011 in U.S. Appl. No. 12/707,599, inventors Dhadialla et al., filed Feb. 17, 2010.
Bonneton et al., "Rapid Divergence of the Ecdysone Receptor in Diptera and Lepidoptera Suggests Coevolution Between ECR and USP-RXR," *Molec. Biol. Evolution* 20: 541-553, University of Chicago Press, United States (2003).
Egea et al., "Effects of Ligand Binding on the Association Properties and Conformation in Solution of Retinoic Acid Receptors RXR and RAR," *J. Mol. Biol.* 307: 557-576, Academic Press, United States (2001).
Hayward et al., "The structure of the USP/RXR of *Xenos pecki* indicates that Strepsiptera are not closely related to Diptera," *Development Genes Evolution* 215: 213-219, Springer-Verlag, United States (2005).
Martinez et al., "Creation of ecdysone receptor chimeras in plants for controlled regulation of gene expression," *Molec. General Genetics* 261: 546-552, Springer-Verlag, United States (1999).
Moradpour et al., "Independent Regulation of Two Separate Gene Activities in a Continuous Human Cell Line," *Biol. Chemistry* 379: 1189-1191, Walter de Gruyter, United States (1988).
Shea et al., "An *rxr/usp* homolog from the parasitic nematode, *Dirofilaria immitis*," *Gene: An International Journal on Genes and Genomes* 324: 171-182, Elsevier B.V., The Netherlands (2004).
Guo, X., et al., "Isolation of two functional retinoid X receptor subtypes from the Ixodid tick, *Amblyomma americanum* (L.)," *Moleculat and Cellular Endocrinology* 139:45-60, Elsevier Science Ireland Ltd., Ireland (1998).

* cited by examiner

```
HsRXRbEF APEEMPVDRILEAELAVEQKSDQGVEGPGGTGGSGSSPNDPVTNICQAADKQLFTLVEWA 60
MmRXRbEF APEEMPVDRILEAELAVEQKSDQGVEGPGATGGGGSSPNDPVTNICQAADKQLFTLVEWA 60
HsRXRaEF ANEDMPVERILEAELAVEPKTETYVEAN--MGLNPSSPNDPVTNICQAADKQLFTLVEWA 58
MmRXRaEF ANEDMPVEKILEAELAVEPKTETYVEAN--MGLNPSSPNDPVTNICQAADKQLFTLVEWA 58
HsRXRgEF GHEDMPVERILEAELAVEPKTESYGDMN-----MENSTNDPVTNICHAADKQLFTLVEWA 55
MmRXRgEF SHEDMPVERILEAELAVEPKTESYGDMN-----VENSTNDPVTNICHAADKQLFTLVEWA 55
                     H1                                H3
                                                          B6
HsRXRbEF KRIPHFSSLPLDDQVILLRAGWNELLIASFSHRSIDVRDGILLATGLHVHRNSAHSAGVG 120
MmRXRbEF KRIPHFSSLPLDDQVILLRAGWNELLIASFSHRSIDVRDGILLATGLHVHRNSAHSAGVG 120
HsRXRaEF KRIPHFSELPLDDQVILLRAGWNELLIASFSHRSIAVKDGILLATGLHVHRNSAHSAGVG 118
MmRXRaEF KRIPHFSELPLDDQVILLRAGWNELLIASFSHRSIAVKDGILLATGLHVHRNSAHSAGVG 118
HsRXRgEF KRIPHFSDLTLEDQVILLRAGWNELLIASFSHRSVSVQDGILLATGLHVHRSSAHSAGVG 115
MmRXRgEF KRIPHFSDLTLEDQVILLRAGWNELLIASFSHRSVSVQDGILLATGLHVHRSSAHSRGVG 115
                    H4           H5            S1       S2       H6
                         B8A1                       B9
HsRXRbEF AIFDRVLTELVSKMRDMRMDKTELGCLRAIILFNPDAKGLSNPSEVEVLREKVYASLETY 180
MmRXRbEF AIFDRVLTELVSKMRDMRMDKTELGCLRAIIMFNPDAKGLSNPGEVEILREKVYASLETY 180
HsRXRaEF AIFDRVLTELVSKMRDMQMDKTELGCLRAIVLFNPDSKGLSNPAEVEALREKVYASLEAY 178
MmRXRaEF AIFDRVLTELVSKMRDMQMDKTELGCLRAIVLFNPDSKGLSNPAEVEALREKVYASLEAY 178
HsRXRgEF SIFDRVLTELVSKMKDMQMDKSELGCLRAIVLFNPDAKGLSNPSEVETLREKVYATLEAY 175
MmRXRgEF SIFDRVLTELVSKMKDMQMDKSELGCLRAIVLFNPDAKGLSNPSEVETLREKVYATLEAY 175
              H7                   H8                    H9
                  B10                  B11
HsRXRbEF CKQKYPEQQGRFAKLLLRLPALRSIGLKCLEHLFFFKLIGDTPIDTFLMEMLEAPHQLA 239
MmRXRbEF CKQKYPEQQGRFAKLLLRLPALRSIGLKCLEHLFFFKLIGDTPIDTFLMEMLEAPHQLA 239
HsRXRaEF CKHKYPEQPGRFAKLLLRLPALRSIGLKCLEHLFFFKLIGDTPIDTFLMEMLEAPHQMT 237
MmRXRaEF CKHKYPEQPGRFAKLLLRLPALRSIGLKCLEHLFFFKLIGDTPIDTFLMEMLEAPHQAT 237
HsRXRgEF TKQKYPEQPGRFAKLLLRLPALRSIGLKCLEHLFFFKLIGDTPIDTFLMEMLETPLQIT 234
MmRXRgEF TKQKYPEQPGRFAKLLLRLPALRSIGLKCLEHLFFFKLIGDTPIDSFLMEMLETPLQIT 234
                           H10         H11                H12   F
```

Figure 3A

```
LmRXREF   HTDMPVERILEAEKRVECKAENQ-----------------------------------VEY  26
AmRXREF   HSDMPIERILEAEKRVECKMEQQ-----------------------------------GNY  26
TmRXREF   -AEMPLDRIIEAEKRIECTPAGGSGG-----------------------------VGEQ  29
CpRXREF   -SDMPIASIREAELSVDPIDEQPLDQGVRLQVPLAPPDSEKCSFTLPFHPVSEVSCANPL  59
AmaRXR1EF PPEMPLERILEAELRVES-QTGTLSES----------------------------AQQ-  29
AmaRXR2EF SPDMPLERILEAEMRVEQPAPSVLAQT----------------------------AASG  31
                 H1

LmRXREF   E----------------LVEWAKHIPHFTSLPLEDQVLLLRAGWNELLIAAFSHRSVDVK  70
AmRXREF   ENAVSHICNATNKQLFQLVAWAKHIPHFTSLPLEDQVLLLRAGWNELLIASFSHRSIDVK  86
TmRXREF   HDGVNNICQATNKQLFQLVQWAKLIPHFTSLPMSDQVLLLRAGWNELLIAAFSHRSIQAQ  89
CpRXREF   QDVVSNICQAADRHLVQLVEWAKHIPHFTDLPIEDQVVLLKAGWNELLIASFSHRSMGVE 119
AmaRXR1EF QDPVSSICQAADRQLHQLVQWAKHIPHFEELPLEDRMVLLKAGWNELLIAAFSHRSVDVR  89
AmaRXR2EF RDPVNSMCQAAP-PLHELVQWARRIPHFEELPIEDRTALLKAGWNELLIAAFSHRSVAVR  90
                    H3                          H4          H5

                          B6                           B8 A1         B9
LmRXREF   DGTVLATGLTVHRNSAHQAGVGTIFDRVLTELVAKMREMKMDKTELGCLRSVILFNPEVR 130
AmRXREF   DGIVLATGITVHRNSAQQAGVGTIFDRVLSELVSKMREMKMDKTELGCLRSIILFNPEVR 146
TmRXREF   DAIVLATGLIVNKTSAHAVGVGNIYDRVLSELVNKMKEMKMDKTELGCLRAIILYNPTCR 149
CpRXREF   DGIVLATGLVIHRSSAHQAGVGAIFDRVLSELVAKMKEMKIDKTELGCLRSIVLFNPDAK 179
AmaRXR1EF DGTVLATGLVVQRHSAHGAGVGAIFDRVLTELVAKMREMKMDRTELGCLLAVVLFNPEAK 149
AmaRXR2EF DGIVLATGLVVQRHSAHGAGVGDIFDRVLAELVAKMRDMKMDKTELGCLRAVVLFNPDAK 150
           S1     S2   H6       H7                  H8

                                          B10                   B11
LmRXREF   GLKSAQEVELLREKVYAALEEYTRTTHPDEPGRFAKLLLRLPSLRSIGLKCLEHLFFFRL 190
AmRXREF   GLKSIQEVTLLREKIYGALEGYCRVAWPDDAGRFAKLLLRLPAIRSIGLKCLEYLFFFKM 206
TmRXREF   GIKSVQEVEMLREKIYGVLEEYTRTTHPNEPGRFAKLLLRLPALRSIGLKCSEHLFFFKL 209
CpRXREF   GLNCVNDVEILREKVYAALEEYTRTTYPDEPGRFAKLLLRLPALRSIGLKCLEYLFLFKL 239
AmaRXR1EF GLRTCPSGGPEGESV-SALEEHCRQQYPDQPGRFAKLLLRLPALRSIGLKCLEHLFFFKL 208
AmaRXR2EF GLRNATRVEALREKVYAALEEHCRRHHPDQPGRFGKLLLRLPALRSIGLKCLEHLFFFKL 210
                    H9                        H10           H11

LmRXREF   IGDVPIDTFLMEMLESPSDS-------   210
AmRXREF   IGDVPIDDFLVEMLESRSDP-------   226
TmRXREF   IGDVPIDTFLMEMLESPADA------    229
CpRXREF   IGDTPLDSYLMKMLVDNPNTSVTPPTS   266
AmaRXR1EF IGDTPIDNFLLSMLEAPSDP-------   228
AmaRXR2EF IGDTPIDSFLLNMLEAPADP-------   230
                H12   F
```

Figure 3B

ECDYSONE RECEPTOR/INVERTEBRATE RETINOID X RECEPTOR-BASED INDUCIBLE GENE EXPRESSION SYSTEM

This application is the U.S. national phase of International Application No. PCT/US02/005235, filed Feb. 20, 2002, which claims the benefit of U.S. Provisional Application No. 60/269,799, filed Feb. 20, 2001; and U.S. Provisional Application No. 60/294,814, filed May 31, 2001.

FIELD OF THE INVENTION

This invention relates to the field of biotechnology or genetic engineering. Specifically, this invention relates to the field of gene expression. More specifically, this invention relates to a novel ecdysone receptor/invertebrate retinoid X receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83: 5414-5418; Arnheiter et al., 1990, Cell 62: 51-61; Filmus et al., 1992, Nucleic Acids Research 20: 27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262:1019-24; Belshaw et al., 1996, *Proc Natl Acad Sci USA* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998, Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67: 59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, this system is not effective for inducing reporter gene expression in animal cells (for comparison, see Example 1.2, below).

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). For most applications that rely on modulating gene expression, these EcR-based systems are undesirable. Therefore, a need exists in the art for improved systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. Improved systems that are simple, compact, and dependent on ligands that are relatively inexpensive, readily available, and of low toxicity to the host would prove useful for regulating biological systems.

Recently, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215.

Applicants previously demonstrated that an ecdysone receptor-based gene expression system in partnership with a dipteran (*Drosophila melanogaster*) or a lepidopteran (*Choristoneura fumiferana*) ultraspiracle protein (USP) is constitutively expressed in mammalian cells, while an ecdysone receptor-based gene expression system in partnership with a vertebrate retinoid X receptor (RXR) is inducible in mammalian cells (pending application PCT/US01/09050). Applicants have now made the surprising discovery that a non-dipteran and non-lepidopteran invertebrate RXR homolog can function similar to vertebrate RXR in an ecdysone receptor-based inducible gene expression system. As described herein, Applicants' novel ecdysone receptor/invertebrate retinoid X receptor-based inducible gene expression system provides an improved inducible gene expression system in yeast and mammalian cells that is characterized by increased ligand sensitivity and magnitude of transactivation.

SUMMARY OF THE INVENTION

The present invention relates to a novel ecdysone receptor/invertebrate retinoid X receptor-based inducible gene expression system, novel receptor polynucleotides and polypeptides for use in the novel inducible gene expression system, and methods of modulating the expression of a gene within a host cell using this inducible gene expression system. In particular, Applicants' invention relates to an improved gene expression modulation system comprising a polynucleotide encoding a ligand binding domain of an invertebrate retinoid X receptor (RXR) polypeptide.

Specifically, the present invention relates to a gene expression modulation system comprising: a) a first gene expression cassette that is capable of being expressed in a host cell comprising a polynucleotide that encodes a first hybrid polypeptide comprising: i) a DNA-binding domain that recognizes a response element associated with a gene whose expression is to be modulated; and ii) an ecdysone receptor ligand binding domain; and b) a second gene expression cassette that is capable of being expressed in the host cell comprising a polynucleotide sequence that encodes a second hybrid polypeptide comprising: i) a transactivation domain; and an invertebrate retinoid X receptor ligand binding domain.

The present invention also relates to a gene expression modulation system comprising: a) a first gene expression cassette that is capable of being expressed in a host cell comprising a polynucleotide that encodes a first hybrid polypeptide comprising: i) a DNA-binding domain that recognizes a response element associated with a gene whose expression is to be modulated; and ii) an invertebrate retinoid X receptor ligand binding domain; and b) a second gene expression cassette that is capable of being expressed in the host cell comprising a polynucleotide sequence that encodes a second hybrid polypeptide comprising: i) a transactivation domain; and an ecdysone receptor ligand binding domain.

The present invention also relates to a gene expression modulation system according to the invention further comprising c) a third gene expression cassette comprising: i) a response element to which the DNA-binding domain of the first hybrid polypeptide binds; a promoter that is activated by the transactivation domain of the second hybrid polypeptide; and iii) a gene whose expression is to be modulated.

The present invention also relates to a gene expression cassette that is capable of being expressed in a host cell, wherein the gene expression cassette comprises a polynucleotide that encodes a hybrid polypeptide comprising either i) a DNA-binding domain that recognizes a response element associated with a gene whose expression is to be modulated, or ii) a transactivation domain; and an invertebrate retinoid X receptor ligand binding domain.

The present invention also relates to an isolated polynucleotide that encodes a hybrid polypeptide comprising either i) a DNA-binding domain that recognizes a response element associated with a gene whose expression is to be modulated, or ii) a transactivation domain; and an invertebrate retinoid X receptor ligand binding domain.

The present invention also relates to an isolated polynucleotide encoding a truncated invertebrate RXR polypeptide, wherein the truncation mutation affects ligand binding activity or ligand sensitivity of the invertebrate RXR polypeptide.

The present invention also relates to an isolated polynucleotide encoding a truncated invertebrate RXR polypeptide comprising a truncation mutation that increases ligand sensitivity of a heterodimer comprising the truncated invertebrate RXR polypeptide and a dimerization partner. In a specific embodiment, the dimerization partner is an ecdysone receptor polypeptide.

The present invention also relates to an isolated polypeptide encoded by a polynucleotide according to Applicants' invention.

The present invention also relates to an isolated hybrid polypeptide comprising either i) a DNA-binding domain that recognizes a response element associated with a gene whose expression is to be modulated, or ii) a transactivation domain; and an invertebrate retinoid X receptor ligand binding domain.

The present invention relates to an isolated truncated invertebrate RXR polypeptide comprising a truncation mutation, wherein the invertebrate RXR polypeptide is encoded by a polynucleotide according to the invention.

Thus, the present invention also relates to an isolated truncated invertebrate RXR polypeptide comprising a truncation mutation that affects ligand binding activity or ligand sensitivity of said invertebrate RXR polypeptide.

The present invention also relates to an isolated truncated invertebrate RXR polypeptide comprising a truncation mutation that increases ligand sensitivity of a heterodimer comprising the truncated invertebrate RXR polypeptide and a dimerization partner. In a specific embodiment, the dimerization partner is an ecdysone receptor polypeptide.

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; b) introducing into the host cell a gene expression cassette comprising i) a response element comprising a domain to which the DNA binding domain from the first hybrid polypeptide of the gene expression modulation system binds; ii) a promoter that is activated by the transactivation domain of the second hybrid polypeptide of the gene expression modulation system; and iii) a gene whose expression is to be modulated; and c) introducing into the host cell a ligand; whereby upon introduction of the ligand into the host cell, expression of the gene is modulated.

Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Applicants' invention also provides an isolated host cell comprising an inducible gene expression system according to the invention. The present invention also relates to an isolated host cell comprising a gene expression cassette, a polynucleotide, or a polypeptide according to the invention. Accordingly, Applicants' invention also relates to a non-human organism comprising a host cell according to the invention.

BRIEF DESCRIPTION OF THE DRAWINGS

FIG. 3: Amino acid sequence alignments of the EF domains of six vertebrate RXRs (A) and six invertebrate RXRs (B). Helices 1-12 are denoted as H1-H12 and β pleated sheets are denoted as S1 and S2. F denotes the F domain junction.

DETAILED DESCRIPTION OF THE INVENTION

Figure 1:
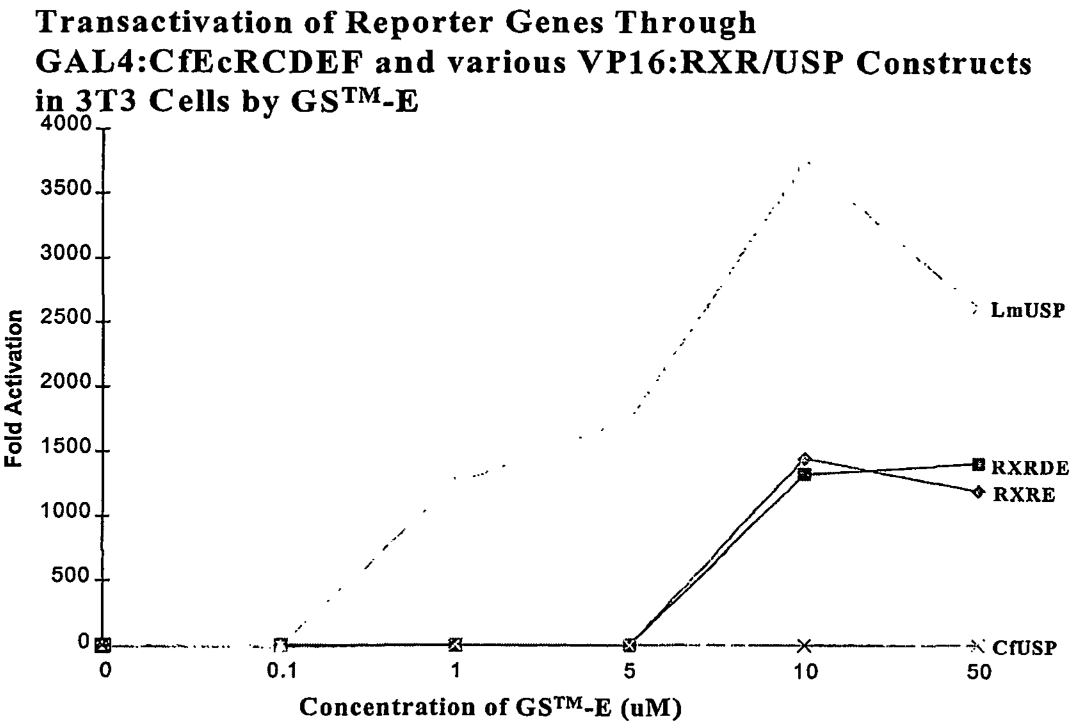
FIG. 1: Transactivation of reporter genes through VP16MmRXRDEF, VP16MmRXREF, VP16LmUSP, and VP16CfUSP constructs transfected into NIH3T3 cells along with GAL4CfEcRCDEF, pFRLuc and pTKRL plasmid DNAs by a non-steroidal ligand.

Applicants have developed a novel ecdysone receptor-based inducible gene expression system comprising an invertebrate retinoid X receptor polypeptide. Applicants have also shown that truncations of an invertebrate RXR polypeptide are also functional within this gene expression system and that these mutational effects may increase or reduce ligand binding activity or ligand sensitivity and may be steroid or non-steroid specific. Thus, Applicants' invention provides an ecdysone receptor/invertebrate RXR-based inducible gene expression system useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' novel inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

DEFINITIONS

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, I., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule. As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as PBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, PNAS 84: 7413; Mackey, et al., 1988, Proc. Natl. Acad. Sci. U.S.A. 85: 8027-8031; and Ulmer et al., 1993, Science 259: 1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5: 120-131); AGGTCAN$_{(n)}$AGGTCA, where N$_{(n)}$ can be one or more spacer nucleotides (see D'Avino P P., et. al., (1995), *Mol. Cell. Endocrinol* 113: 1-9); and GGGTTGAATGAATTT (see Antoniewski C., et. al., (1994), Mol. Cell Biol. 14: 4465-4474).

The term "operably linked" refers to the association of nucleic acid sequences on a single nucleic acid fragment so that the function of one is affected by the other. For example, a promoter is operably, linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $lP_L$, $lP_R$, T7, tac, and trc promoters (useful for expression in *Escherichia coli*); light regulated-promoters; animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

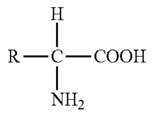

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, “substantially similar” refers to nucleic acid fragments wherein changes in one or more nucleotide bases results in substitution of one or more amino acids, but do not affect the functional properties of the protein encoded by the DNA sequence. “Substantially similar” also refers to nucleic acid fragments wherein changes in one or more nucleotide bases does not affect the ability of the nucleic acid fragment to mediate alteration of gene expression by antisense or co-suppression technology. “Substantially similar” also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are “substantially homologous” or “substantially similar” when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term “corresponding to” is used herein to refer to similar or homologous sequences, whether the exact position is identical or different from the molecule to which the similarity or homology is measured. A nucleic acid or amino acid sequence alignment may include spaces. Thus, the term “corresponding to” refers to the sequence similarity, and not the numbering of the amino acid residues or nucleotide bases.

A “substantial portion” of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a “substantial portion” of a nucleotide sequence comprises enough of the sequence to specifically identify and/or isolate a nucleic acid fragment comprising the sequence.

The term “percent identity”, as known in the art, is a relationship between two or more polypeptide sequences or two or more polynucleotide sequences, as determined by comparing the sequences. In the art, “identity” also means the degree of sequence relatedness between polypeptide or polynucleotide sequences, as the case may be, as determined by the match between strings of such sequences. “Identity” and “similarity” can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term “sequence analysis software” refers to any computer algorithm or software program that is useful for the analysis of nucleotide or amino acid sequences. “Sequence analysis software” may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215: 403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the “default values” of the program referenced, unless otherwise specified. As used herein “default values” will mean any set of values or parameters which originally load with the software when first initialized.

“Synthetic genes” can be assembled from oligonucleotide building blocks that are chemically synthesized using procedures known to those skilled in the art. These building blocks are ligated and annealed to form gene segments that are then enzymatically assembled to construct the entire gene. “Chemically synthesized”, as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Gene Expression Modulation System of the Invention

Applicants have previously shown that separating the transactivation and DNA binding domains by placing them on two different proteins results in greatly reduced background activity in the absence of a ligand and significantly increased activity over background in the presence of a ligand (pending application PCT/US01/09050). This two-hybrid system is a significantly improved inducible gene expression modulation system compared to the two systems disclosed in International Patent Applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

The two-hybrid ecdysone receptor-based gene expression modulation system may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9: 222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity.

Examples of corepressors include N—CoR and SMRT (for review, see Horwitz et al. Mol. Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240: 889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. This EcR receptor, like a subset of the steroid receptor family, also possesses less well-defined regions responsible for heterodimerization properties. Because the domains of EcR, USP, and RXR are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050). This two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a specific embodiment of the two-hybrid system, native DNA binding and transactivation domains of EcR or RXR are eliminated and as a result, these hybrid molecules have less chance of interacting with other steroid hormone receptors present in the cell resulting in reduced side effects.

Applicants have previously shown that an ecdysone receptor in partnership with a dipteran (fruit fly *Drosophila melanogaster*) or a lepidopteran (spruce bud worm *Choristoneura fumiferana*) ultraspiracle protein (USP) is constitutively expressed in mammalian cells, while an ecdysone receptor in partnership with a vertebrate retinoid X receptor (RXR) is inducible in mammalian cells (pending application PCT/US01/09050). Applicants have now made the surprising discovery that the ultraspiracle protein of *Locusta migratoria* ("LmUSP") and the RXR homolog 1 and RXR homolog 2 of the ixodid tick *Amblyomma americanum* ("AmaRXR1" and "AmaRXR2", respectively) can function similar to vertebrate retinoid X receptor (RXR) in an inducible ecdysone receptor-based inducible gene expression system. Thus, Applicants' findings that LmUSP, AmaRXR1, AmaRXR2, and their non-Dipteran, non-Lepidopteran homologs including, but not limited to: fiddler crab *Celuca pugilator* RXR homolog ("CpRXR"), beetle *Tenebrio molitor* RXR homolog ("TmRXR"), honeybee *Apis mellifera* RXR homolog ("AmRXR"), and aphid *Myzus persicae* RXR homolog ("MpRXR"), all of which are referred to herein collectively as invertebrate RXRs, can be substituted for vertebrate RXR in ecdysone receptor-based inducible gene expression systems can only be regarded as unexpected and surprising. As described herein, Applicants' novel ecdysone receptor/invertebrate RXR-based inducible gene expression system provides an improved inducible gene expression system in yeast and mammalian cells that is characterized by increased ligand sensitivity and magnitude of transactivation.

In particular, Applicants describe herein a novel two-hybrid system that comprises an invertebrate RXR ligand binding domain. This novel gene expression system demonstrates for the first time that an invertebrate ultraspiracle protein/RXR homolog can function as a component of an inducible EcR-based inducible gene expression system in yeast and mammalian cells. As discussed herein, this finding is both unexpected and surprising.

Specifically, Applicants' invention relates to a gene expression modulation system comprising: a) a first gene expression cassette that is capable of being expressed in a host cell, wherein the first gene expression cassette comprises a polynucleotide that encodes a first hybrid polypeptide comprising i) a DNA-binding domain that recognizes a response element associated with a gene whose expression is to be modulated; and ii) an ecdysone receptor ligand binding domain; and b) a second gene expression cassette that is capable of being expressed in the host cell, wherein the second gene expression cassette comprises a polynucleotide sequence that encodes a second hybrid polypeptide comprising i) a transactivation domain; and an invertebrate retinoid X receptor ligand binding domain.

The present invention also relates to a gene expression modulation system comprising: a) a first gene expression cassette that is capable of being expressed in a host cell, wherein the first gene expression cassette comprises a polynucleotide that encodes a first hybrid polypeptide comprising i) a DNA-binding domain that recognizes a response element associated with a gene whose expression is to be modulated; and ii) an invertebrate retinoid X receptor ligand binding domain; and b) a second gene expression cassette that is capable of being expressed in the host cell, wherein the second gene expression cassette comprises a polynucleotide sequence that encodes a second hybrid polypeptide comprising i) a transactivation domain; and ii) an ecdysone receptor ligand binding domain.

The present invention also relates to a gene expression modulation system according to the present invention further comprising c) a third gene expression cassette comprising: i) a response element to which the DNA-binding domain of the first hybrid polypeptide binds; ii) a promoter that is activated by the transactivation domain of the second hybrid polypeptide; and iii) a gene whose expression is to be modulated.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domains of an EcR and an invertebrate RXR, which in turn are bound to the response element linked to a gene, provide the means for external temporal regulation of expression of the gene. The binding mechanism or the order in which the various components of this invention bind to each other, that is, for example, ligand to receptor, first hybrid polypeptide to response element, second hybrid polypeptide to promoter, etc., is not critical. Binding of the ligand to the ligand binding domains of an EcR and invertebrate RXR enables expression or suppression of the gene. This mechanism does not exclude the potential for ligand binding to EcR or invertebrate RXR, and the resulting formation of active homodimer complexes (e.g. EcR+EcR or invertebrate RXR+invertebrate RXR). Preferably, one or more of the receptor domains is varied producing a chimeric or hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al., (1988) Nature 335: 563-564) or LexA protein from *Escherichia coli* (see Brent and Ptashne, (1985), Cell 43: 729-736), or synthetic response elements specific for targeted interactions with proteins designed, modified, and selected for such specific interactions (see, for example, Kim, et al. (1997), *Proc. Natl. Acad. Sci., USA* 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

Gene Expression Cassettes of the Invention

The novel EcR/invertebrate RXR-based inducible gene expression system of the invention comprises gene expression cassettes that are capable of being expressed in a host cell, wherein the gene expression cassettes each comprise a polynucleotide encoding a hybrid polypeptide. Thus, Applicants' invention also provides novel gene expression cassettes for use in the gene expression system of the invention.

Specifically, the present invention provides a gene expression cassette comprising a polynucleotide encoding a hybrid polypeptide. In particular, the present invention provides a gene expression cassette that is capable of being expressed in a host cell, wherein the gene expression cassette comprises a polynucleotide that encodes a hybrid polypeptide comprising either i) a DNA-binding domain that recognizes a response element, or a transactivation domain; and an ecdysone receptor ligand binding domain or an invertebrate retinoid X receptor ligand binding domain.

In a specific embodiment, the gene expression cassette encodes a hybrid polypeptide comprising a DNA-binding domain that recognizes a response element and an EcR ligand binding domain.

In another specific embodiment, the gene expression cassette encodes a hybrid polypeptide comprising a DNA-binding domain that recognizes a response element and an invertebrate RXR ligand binding domain.

In another specific embodiment, the gene expression cassette encodes a hybrid polypeptide comprising a transactivation domain and an EcR ligand binding domain.

In another specific embodiment, the gene expression cassette encodes a hybrid polypeptide comprising a transactivation domain and an invertebrate RXR ligand binding domain.

In a preferred embodiment, the ligand binding domain (LBD) is an EcR LBD, an invertebrate RXR LBD, or a related steroid/thyroid hormone nuclear receptor family member LBD, or analogs, combinations, or modifications thereof. In a specific embodiment, the LBD is from an EcR or an invertebrate RXR. In another specific embodiment, the LBD is from a truncated EcR LBD or a truncated invertebrate RXR LBD. A truncation mutation may be made by any method used in the art, including but not limited to restriction endonuclease digestion/deletion, PCR-mediated/oligonucleotide-directed deletion, chemical mutagenesis, DNA strand breakage, and the like.

The EcR may be an invertebrate EcR, preferably selected from the class Arthropod. Preferably the EcR is selected from the group consisting of a Lepidopteran EcR, a Dipteran EcR, an Orthopteran EcR, a Homopteran EcR and a Hemipteran EcR. More preferably, the EcR for use is a spruce budworm *Choristoneura fumiferana* EcR ("CfEcR"), a beetle *Tenebrio molitor* EcR ("TmEcR"), a *Manduca sexta* EcR ("MsEcR"), a *Heliothies virescens* EcR ("HvEcR"), a midge *Chironomus tentans* EcR ("CtEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* ("LcEcR"), a blowfly *Lucilia cuprina* EcR ("LucEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Celuca pugilator* EcR ("CpEcR"), an ixodid tick *Amblyomma americanum* EcR ("AmaEcR"), a whitefly *Bamecia argentifoli* EcR ("BaEcR", SEQ ID NO: 57), or a leafhopper *Nephotetix cincticeps* EcR ("NcEcR", SEQ ID NO: 58). Most preferably, the LBD is from spruce budworm (*Choristoneura fumiferana*) EcR ("CfEcR"), fruit fly *Drosophila melanogaster* EcR ("DmEcR"), whitefly *Bamecia argentifoli* EcR ("BaEcR"), leafhopper *Nephotetix cincticeps* EcR ("NcEcR"), beetle *Tenebrio molitor* EcR ("TmEcR"), or ixodid tick *Amblyomma americanum* EcR ("AmaEcR").

In a specific embodiment, the LBD is from a truncated EcR polypeptide. The EcR polypeptide truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. Preferably, the EcR polypeptide truncation results in a deletion of at least a partial polypeptide domain. More preferably, the EcR polypeptide truncation results in a deletion of at least an entire polypeptide domain. In a specific embodiment, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E domain, or a partial F domain. A combination of several complete and/or partial domain deletions may also be performed.

In one embodiment, the ecdysone receptor ligand binding domain is encoded by a polynucleotide comprising a nucleic acid sequence selected from the group consisting of SEQ ID NO: 2 (DmEcR-EF), SEQ ID NO: 3 (CfEcR-DE), and SEQ ID NO: 4 (DmEcR-DE). In a preferred embodiment, the ecdysone receptor ligand binding domain is encoded by a polynucleotide comprising a nucleic acid sequence selected from the group consisting of SEQ ID NO: 1 (CfEcR-EF), SEQ ID NO: 53 (CfEcR-DEF), and SEQ ID NO: 45 (CfEcR-CDEF).

In one embodiment, the ecdysone receptor ligand binding domain comprises an amino acid sequence selected from the group consisting of SEQ ID NO: 6 (DmEcR-EF), SEQ ID NO: 7 (CfEcR-DE), and SEQ ID NO: 8 (DmEcR-DE). In a preferred embodiment, the ecdysone receptor ligand binding domain comprises an amino acid sequence selected from the group consisting of SEQ ID NO: 5 (CfEcR-EF), SEQ ID NO: 43 (CFEcR-DEF), and SEQ ID NO: 59 (CfEcR-CDEF).

Preferably, the invertebrate RXR polypeptide is a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In a specific embodiment, the LBD is from a truncated invertebrate RXR. The invertebrate RXR polypeptide truncation results in a deletion of at least 1, 2, 3, 4, 5, 6, 8, 10, 13, 14, 15, 16, 17, 18, 19, 20, 21, 22, 25, 26, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, or 240 amino acids. Preferably, the invertebrate RXR polypeptide truncation results in a deletion of at least a partial polypeptide domain. More preferably, the invertebrate RXR polypeptide truncation results in a deletion of at least an entire polypeptide domain. In a specific embodiment, the invertebrate RXR polypeptide truncation results in a deletion of at least a partial E-domain, a complete E-domain, a partial F-domain, a complete F-domain, an EF-domain helix 1, an EF-domain helix 2, an EF-domain helix 3, an EF-domain helix 4, an EF-domain helix 5, an EF-domain helix 6, an EF-domain helix 7, an EF-domain helix 8, and EF-domain helix 9, an EF-domain helix 10, an EF-domain helix 11, an EF-domain helix 12, an EF-domain β-pleated sheet, an A/B-domain, a C-domain, a D-domain, A/B/C-domains, A/B/1/2-C-domains, A/B/C/D-domains, A/B/C/D/F-domains, A/B/F-domains, or A/B/C/F-domains. A combination of several complete and/or partial domain deletions may also be performed.

In a preferred embodiment, the invertebrate RXR ligand binding domain is encoded by a polynucleotide comprising a nucleic acid sequence selected from the group consisting of SEQ ID NO: 9 (LmUSP-EF), SEQ ID NO: 10 (AmaRXR1-EF), SEQ ID NO: 11 (AmaRXR2-EF), SEQ ID NO: 12 (CpRXR-EF), SEQ ID NO: 13 (TmRXR-EF), SEQ ID NO: 14 (AmRXR-EF), SEQ ID NO: 15 (LmUSP-EF, BamHI-deleted), SEQ ID NO: 16 (AmaRXR1-EF, BamHI-deleted), SEQ ID NO: 17 (AmaRXR2-EF, BamHI-deleted), SEQ ID NO: 18 (CpRXR-EF, BamHI-deleted), SEQ ID NO: 19 (TmRXR-EF, BamHI-deleted), and SEQ ID NO: 20 (AmRXR-EF, BamHI-deleted).

In another preferred embodiment, the invertebrate RXR ligand binding domain comprises a polypeptide sequence selected from the group consisting of SEQ ID NO: 21 (LmUSP-EF), SEQ ID NO: 22 (AmaRXR1-EF), SEQ ID NO: 23 (AmaRXR2-EF), SEQ ID NO: 24 (CpRXR-EF), SEQ ID NO: 25 (TmRXR-EF), SEQ ID NO: 26 (AmRXR-EF), SEQ ID NO: 27 (LmUSP-EF, BamHI-deleted), SEQ ID NO: 28 (AmaRXR1-EF, BamHI-deleted), SEQ ID NO: 29 (AmaRXR2-EF, BamHI-deleted), SEQ ID NO: 30 (CpRXR-EF, BamHI-deleted), SEQ ID NO: 31 (TmRXR-EF, BamHI-deleted), and SEQ ID NO: 32 (AmRXR-EF, BamHI-deleted).

For purposes of this invention, EcR and invertebrate RXR also include synthetic and chimeric EcR and invertebrate RXR and their homologs.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a steroid/thyroid hormone nuclear receptor superfamily member DBD, a bacterial LacZ DBD, or a yeast put DBD. More preferably, the DBD is a GAL4 DBD [SEQ ID NO: 33 (polynucleotide) or SEQ ID NO: 34 (polypeptide)] or a LexA DBD [(SEQ ID NO: 35 (polynucleotide) or SEQ ID NO: 36 (polypeptide)].

The transactivation domain (abbreviated "AD" or "TA") may be any steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), or an analog, combination, or modification thereof. In a specific embodiment, the AD is a synthetic or chimeric AD, or is obtained from a VP16, GAL4, NF-kB, or B42 acidic activation domain AD. Preferably, the AD is a VP16 AD [SEQ ID NO: 37 (polynucleotide) or SEQ ID NO: 38 (polypeptide)] or a B42 AD [SEQ ID NO: 39 (polynucleotide) or SEQ ID NO: 40 (polypeptide)].

In a preferred embodiment, the gene expression cassette encodes a hybrid polypeptide comprising a DNA-binding domain encoded by a polynucleotide comprising a nucleic acid sequence selected from the group consisting of a GAM DBD (SEQ ID NO: 33) and a LexA DBD (SEQ ID NO: 35), and an EcR ligand binding domain encoded by a polynucleotide comprising a nucleic acid sequence selected from the group consisting of SEQ ID NO: 1, SEQ ID NO: 53, and SEQ ID NO: 45.

In another preferred embodiment, the gene expression cassette encodes a hybrid polypeptide comprising a DNA-binding domain comprising an amino acid sequence selected from the group consisting of a GAL4 DBD (SEQ ID NO: 34) and a LexA DBD (SEQ ID NO: 36), and an EcR ligand binding domain comprising an amino acid sequence selected from the group consisting of SEQ ID NO: 5, SEQ ID NO: 43, and SEQ ID NO: 59.

In another preferred embodiment, the gene expression cassette encodes a hybrid polypeptide comprising a DNA-binding domain encoded by a polynucleotide comprising a nucleic acid sequence selected from the group consisting of a GAL4 DBD (SEQ ID NO: 33) or a LexA DBD (SEQ ID NO: 35) and an invertebrate RXR ligand binding domain encoded by a polynucleotide comprising a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a DNA-binding domain comprising an amino acid sequence selected from the group consisting of a GAL4 DBD (SEQ ID NO: 34) and a LexA DBD (SEQ ID NO: 36), and an invertebrate RXR ligand binding domain comprising an amino acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In another preferred embodiment, the gene expression cassette encodes a hybrid polypeptide comprising a transactivation domain encoded by a polynucleotide comprising a nucleic acid sequence of SEQ ID NO: 37 or SEQ ID NO: 39, and an EcR ligand binding domain encoded by a polynucleotide comprising a nucleic acid sequence selected from the group consisting of SEQ ID NO: 1, SEQ ID NO: 53, and SEQ ID NO: 45.

In another preferred embodiment, the gene expression cassette encodes a hybrid polypeptide comprising a transactivation domain comprising an amino acid sequence of SEQ ID NO: 38 or SEQ ID NO: 40, and an EcR ligand binding domain comprising an amino acid sequence selected from the group consisting of SEQ ID NO: 5, SEQ ID NO: 43, and SEQ ID NO: 59.

In another preferred embodiment, the gene expression cassette encodes a hybrid polypeptide comprising a transactivation domain encoded by a polynucleotide comprising a nucleic acid sequence of SEQ ID NO: 37 or SEQ ID NO: 39, and an invertebrate RXR ligand binding domain encoded by a polynucleotide comprising a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a transactivation domain comprising an amino acid sequence of SEQ ID NO: 38 or SEQ ID NO: 40 and an invertebrate RXR ligand binding domain comprising an amino acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ BD NO: 27, SEQ ID NO: 28, SEQ ID NO: 29, SEQ ID NO: 30, SEQ ID NO: 31, and SEQ ID NO: 32.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a steroid/thyroid hormone nuclear receptor RE, or a synthetic RE that recognizes a synthetic DNA binding domain. Preferably, the RE is a GALORE comprising a polynucleotide sequence of SEQ ID NO: 41 or a LexA RE (operon, "op") comprising a polynucleotide sequence of SEQ ID NO: 42 ("2XLexAopRE"). Preferably, the first hybrid protein is substantially free of a transactivation domain and the second hybrid protein is substantially free of a DNA binding domain. For purposes of this invention, "substantially free" means that the protein in question does not contain a sufficient sequence of the domain in question to provide activation or binding activity.

Thus, the present invention also relates to a gene expression cassette comprising: i) a response element comprising a domain to which a polypeptide comprising a DNA binding domain binds; ii) a promoter that is activated by a polypeptide comprising a transactivation domain; and iii) a gene whose expression is to be modulated.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Polynucleotides of the Invention

The novel ecdysone receptor/invertebrate retinoid X receptor-based inducible gene expression system of the invention comprises a gene expression cassette comprising a polynucleotide that encodes a hybrid polypeptide comprising a) a DNA binding domain or a transactivation domain, and b) an EcR ligand binding domain or an invertebrate RXR ligand binding domain. These gene expression cassettes, the polynucleotides they comprise, and the hybrid polypeptides they encode are useful as components of an EcR-based gene expression system to modulate the expression of a gene within a host cell.

Thus, the present invention provides an isolated polynucleotide that encodes a hybrid polypeptide comprising a) a DNA binding domain or a transactivation domain according to the invention, and b) an EcR ligand binding domain or an invertebrate RXR ligand binding domain according to the invention.

The present invention also relates to an isolated polynucleotide that encodes a truncated EcR or a truncated invertebrate RXR polypeptide comprising a truncation mutation according to the invention. Specifically, the present invention relates to an isolated polynucleotide encoding an EcR or an invertebrate RXR polypeptide comprising a truncation mutation that affects ligand binding activity or ligand sensitivity that is useful in modulating gene expression in a host cell.

In a specific embodiment, the isolated truncated EcR polynucleotide comprises a polynucleotide sequence selected from the group consisting of SEQ ID NO: 1, SEQ ID NO: 53 and SEQ ID NO: 45.

In another specific embodiment, the isolated truncated EcR polynucleotide encodes a truncated ecdysone receptor polypeptide comprising an amino acid sequence selected from the group consisting of SEQ ID NO: 5, SEQ ID NO: 43 and SEQ ID NO: 59.

In another specific embodiment, the isolated truncated invertebrate RXR polynucleotide according to the invention comprises a polynucleotide sequence selected from the group consisting of SEQ ID NO: 15, SEQ ID NO: 16, SEQ ID NO: 17, SEQ ID NO: 18, SEQ ID NO: 19, and SEQ ID NO: 20.

In another specific embodiment, the isolated truncated invertebrate RXR polynucleotide according to the invention encodes a truncated invertebrate RXR polypeptide comprising an amino acid sequence consisting of SEQ ID NO: 27, SEQ ID NO: 28, SEQ ID NO: 29, SEQ ID NO: 30, SEQ ID NO: 31, and SEQ ID NO: 32.

In particular, the present invention relates to an isolated polynucleotide encoding an invertebrate RXR polypeptide comprising a truncation mutation, wherein the mutation reduces ligand binding activity or ligand sensitivity of the invertebrate RXR polypeptide. In a specific embodiment, the present invention relates to an isolated polynucleotide encoding an invertebrate RXR polypeptide comprising a truncation mutation that reduces steroid binding activity or steroid sensitivity of the invertebrate RXR polypeptide.

In another specific embodiment, the present invention relates to an isolated polynucleotide encoding an invertebrate RXR polypeptide comprising a truncation mutation that reduces non-steroid binding activity or non-steroid sensitivity of the invertebrate RXR polypeptide.

The present invention also relates to an isolated polynucleotide encoding an invertebrate RXR polypeptide comprising a truncation mutation, wherein the mutation enhances ligand binding activity or ligand sensitivity of the invertebrate RXR polypeptide. In a specific embodiment, the present invention relates to an isolated polynucleotide encoding an invertebrate RXR polypeptide comprising a truncation mutation that enhances steroid binding activity or steroid sensitivity of the invertebrate RXR polypeptide.

In another specific embodiment, the present invention relates to an isolated polynucleotide encoding an invertebrate RXR polypeptide comprising a truncation mutation that enhances non-steroid binding activity or non-steroid sensitivity of the invertebrate RXR polypeptide.

The present invention also relates to an isolated polynucleotide encoding an invertebrate retinoid X receptor polypeptide comprising a truncation mutation that increases ligand sensitivity of a heterodimer comprising the mutated invertebrate retinoid X receptor polypeptide and a dimerization partner. Preferably, the isolated polynucleotide encoding an invertebrate retinoid X receptor polypeptide comprising a truncation mutation that increases ligand sensitivity of a heterodimer comprises a polynucleotide sequence selected from the group consisting of SEQ ID NO: 9 (LmUSP-EF), SEQ ID NO: 10 (AmaRXR1-EF), SEQ ID NO: 11 (AmaRXR2-EF), SEQ ID NO: 12 (CpRXR-EF), SEQ ID NO: 13 (TmRXR-EF), and SEQ ID NO: 14 (AmRXR-EF). In a specific embodiment, the dimerization partner is an ecdysone receptor polypeptide. Preferably, the dimerization partner is a truncated EcR polypeptide. More preferably, the dimerization partner is an EcR polypeptide in which domain A/B has been deleted. Even more preferably, the dimerization partner is an EcR polypeptide comprising an amino acid sequence of SEQ ID NO: 5 (CfEcR-EF), SEQ ID NO: 43 (CfEcR-DEF) or SEQ ID NO: 59 (CfEcR-CDEF).

Polypeptides of the Invention

The novel ecdysone receptor/invertebrate retinoid X receptor-based inducible gene expression system of the invention comprises a gene expression cassette comprising a polynucleotide that encodes a hybrid polypeptide comprising a) a DNA binding domain or a transactivation domain, and b) an EcR ligand binding domain or an invertebrate RXR ligand binding domain. These gene expression cassettes, the polynucleotides they comprise, and the hybrid polypeptides they encode are useful as components of an EcR-based gene expression system to modulate the expression of a gene within a host cell.

Thus, the present invention also relates to a hybrid polypeptide comprising a) a DNA binding domain or a transactivation domain according to the invention, and b) an EcR ligand binding domain or an invertebrate RXR ligand binding domain according to the invention.

The present invention also relates to an isolated truncated EcR or an isolated truncated invertebrate RXR polypeptide comprising a truncation mutation according to the invention. Specifically, the present invention relates to an isolated truncated EcR or an isolated truncated invertebrate RXR polypeptide comprising a truncation mutation that affects ligand binding activity or ligand sensitivity.

In a specific embodiment, the isolated truncated EcR polypeptide is encoded by a polynucleotide comprising a polynucleotide sequence selected from the group consisting of SEQ ID NO: 1, SEQ ID NO: 53 and SEQ ID NO: 45.

In another specific embodiment, the isolated truncated EcR polypeptide comprises an amino acid sequence selected from the group consisting of SEQ ID NO: 5, SEQ ID NO: 43 and SEQ ID NO: 59.

In another specific embodiment, the isolated truncated invertebrate RXR polypeptide is encoded by a polynucleotide comprising a polynucleotide sequence selected from the group consisting of SEQ ID NO: 15, SEQ ID NO: 16, SEQ ID NO: 17, SEQ ID NO: 18, SEQ ID NO: 19, and SEQ ID NO: 20.

In another specific embodiment, the isolated truncated invertebrate RXR polypeptide comprises an amino acid sequence selected from the group consisting of SEQ ID NO: 27, SEQ ID NO: 28, SEQ ID NO: 29, SEQ ID NO: 30, SEQ ID NO: 31, and SEQ ID NO: 32.

The present invention relates to an isolated invertebrate RXR polypeptide comprising a truncation mutation that reduces ligand binding activity or ligand sensitivity of the invertebrate RXR polypeptide, wherein the polypeptide is encoded by a polynucleotide comprising a polynucleotide sequence selected from the group consisting of SEQ ID NO: 15, SEQ ID NO: 16, SEQ ID NO: 17, SEQ ID NO: 18, SEQ ID NO: 19, and SEQ ID NO: 20.

Thus, the present invention relates to an isolated invertebrate RXR polypeptide comprising a truncation mutation that reduces ligand binding activity or ligand sensitivity of the invertebrate RXR polypeptide, wherein the polypeptide comprises an amino acid sequence selected from the group consisting of SEQ ID NO: 27, SEQ ID NO: 28, SEQ ID NO: 29, SEQ ID NO: 30, SEQ ID NO: 31, and SEQ ID NO: 32.

In a specific embodiment, the present invention relates to an isolated invertebrate RXR polypeptide comprising a truncation mutation that reduces steroid binding activity or steroid sensitivity of the invertebrate RXR polypeptide.

In another specific embodiment, the present invention relates to an isolated invertebrate RXR polypeptide comprising a truncation mutation that reduces non-steroid binding activity or non-steroid sensitivity of the invertebrate RXR polypeptide.

In addition, the present invention relates to an isolated invertebrate RXR polypeptide comprising a truncation mutation that enhances ligand binding activity or ligand sensitivity of the invertebrate RXR polypeptide.

The present invention relates to an isolated invertebrate RXR polypeptide comprising a truncation mutation that enhances ligand binding activity or ligand sensitivity of the invertebrate RXR polypeptide. In a specific embodiment, the present invention relates to an isolated invertebrate RXR polypeptide comprising a truncation mutation that enhances steroid binding activity or steroid sensitivity of the invertebrate RXR polypeptide.

In another specific embodiment, the present invention relates to an isolated invertebrate RXR polypeptide comprising a truncation mutation that enhances non-steroid binding activity or non-steroid sensitivity of the invertebrate RXR polypeptide.

The present invention also relates to an isolated invertebrate retinoid X receptor polypeptide comprising a truncation mutation that increases ligand sensitivity of a heterodimer comprising the mutated invertebrate retinoid X receptor polypeptide and a dimerization partner. Preferably, the isolated invertebrate retinoid X receptor polypeptide comprising a truncation mutation that increases ligand sensitivity of a heterodimer is encoded by a polynucleotide comprising a nucleic acid sequence selected from the group consisting of SEQ ID NO: 9 (LmUSP-EF), SEQ ID NO: 10 (AmaRXR1-EF), SEQ ID NO: 11 (AmaRXR2-EF), SEQ ID NO: 12 (CpRXR-EF), SEQ ID NO: 13 (TmRXR-EF), and SEQ ID NO: 14 (AmRXR-EF). More preferably, the isolated polynucleotide encoding an invertebrate retinoid X receptor polypeptide comprising a truncation mutation that increases ligand sensitivity of a heterodimer comprises an amino acid sequence selected from the group consisting of SEQ ID NO: 21 (LmUSP-EF), SEQ ID NO: 22 (AmaRXR1-EF), SEQ ID NO: 23 (AmaRXR2-EF), SEQ ID NO: 24 (CpRXR-EF), SEQ ID NO: 25 (TmRXR-EF), and SEQ ID NO: 26 (AmRXR-EF).

In a specific embodiment, the dimerization partner is an ecdysone receptor polypeptide. Preferably, the dimerization partner is a truncated EcR polypeptide. More preferably, the dimerization partner is an EcR polypeptide in which domain A/B has been deleted. Even more preferably, the dimerization partner is an EcR polypeptide comprising an amino acid sequence of SEQ ID NO: 5 (CfEcR-EF), SEQ ID NO: 43 (CfEcR-DEF) or SEQ ID NO: 59 (CfEcR-CDEF).

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the first hybrid polypeptide; a promoter that is activated by the transactivation domain of the second hybrid polypeptide; and a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette comprising i) a response element comprising a domain recognized by the DNA binding domain from the first hybrid polypeptide; ii) a promoter that is activated by the transactivation domain of the second hybrid polypeptide; and a gene whose expression is to be modulated; and c) introducing into the host cell a ligand; whereby upon introduction of the ligand into the host cell, expression of the gene is modulated.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the two-hybrid system to the response element in the presence of the ligand results in activation or suppression of expression of the genes. Preferred ligands include ponasterone, muristerone A, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N, N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, and the like.

In a preferred embodiment, the ligand for use in Applicants' method of modulating expression of gene is a compound of the formula:

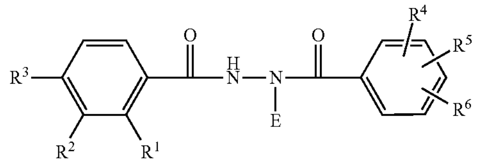

wherein:

E is a ($C_4$-$C_6$)alkyl containing a tertiary carbon or a cyano($C_3$-$C_5$)alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH═CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH═CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt.

In another preferred embodiment, a second ligand may be used in addition to the first ligand discussed above in Applicants' method of modulating expression of a gene, wherein the second ligand is 9-cis-retinoic acid or a synthetic analog of retinoic acid.

Applicants' invention provides for modulation of gene expression in prokaryotic and eukaryotic host cells. Thus, the present invention also relates to a method for modulating gene expression in a host cell selected from the group consisting of a bacterial cell, a fungal cell, a yeast cell, an animal cell, and a mammalian cell. Preferably, the host cell is a yeast cell, a hamster cell, a mouse cell, a monkey cell, or a human cell.

Expression in transgenic host cells may be useful for the expression of various polypeptides of interest including but not limited to therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Host Cells and Non-Human Organisms of the Invention

As described above, the gene expression modulation system of the present invention may be used to modulate gene expression in a host cell. Expression in transgenic host cells may be useful for the expression of various genes of interest. Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. The isolated host cell may be either a prokaryotic or a eukaryotic host cell.

Preferably, the host cell is selected from the group consisting of a bacterial cell, a fungal cell, a yeast cell, an animal cell, and a mammalian cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*, animal, and mammalian host cells.

In a specific embodiment, the host cell is a yeast cell selected from the group consisting of a *Saccharomyces*, a *Pichia*, and a *Candida* host cell.

In another specific embodiment, the host cell is a hamster cell.

In another specific embodiment, the host cell is a murine cell.

In another specific embodiment, the host cell is a monkey cell.

In another specific embodiment, the host cell is a human cell.

Host cell transformation is well known in the art and may be achieved by a variety of methods including but not limited to electroporation, viral infection, plasmid/vector transfection, non-viral vector mediated transfection, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. Preferably, the non-human organism is selected from the group consisting of a bacterium, a fungus, a yeast, an animal, and a mammal. More preferably, the non-human organism is a yeast, a mouse, a rat, a rabbit, a cat, a dog, a bovine, a goat, a pig, a horse, a sheep, a monkey, or a chimpanzee.

In a specific embodiment, the non-human organism is a yeast selected from the group consisting of *Saccharomyces, Pichia*, and *Candida*.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full- or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "μl" means microliter(s), "ml" means milliliter(s), "L" means liter(s), "μM" means micromolar, "mM" means millimolar, "μg" means microgram(s), "mg" means milligram(s), "A" means adenine or adenosine, "T" means thymine or thymidine, "G" means guanine or guanosine, "C" means cytidine or cytosine, "×g" means times gravity, "nt" means nucleotide(s), "aa" means amino acid(s), "bp" means base pair(s), "kb" means kilobase(s), "k" means kilo, "μ" means micro, and "° C." means degrees Celsius.

Example 1

Applicants' EcR/invertebrate RXR-based inducible gene modulation system is useful in various applications including gene therapy, expression of proteins of interest in host cells, production of transgenic organisms, and cell-based assays. In various cellular backgrounds, including mammalian cells, invertebrate EcR heterodimerizes with vertebrate RXR and, upon binding of ligand, transactivates genes under the control of ecdysone response elements. Applicants have made the surprising discovery that invertebrate RXR can substitute for vertebrate RXR and provide a novel inducible gene expression system for yeast and animal cell applications. This Example describes the construction of several gene expression cassettes for use in the EcR-based inducible gene expression system of the invention.

Applicants constructed several EcR-based gene expression cassettes based on the spruce budworm *Choristoneura fumiferana* EcR ("CfEcR"), *C. fumiferana* ultraspiracle ("CfUSP"), *Drosophila melanogaster* USP ("DmUSP"), mouse *Mus musculus* retinoid X receptor α ("MmRXRα"), locust *Locusta migratoria* USP ("LmUSP"), an invertebrate homolog of vertebrate RXR, *Amblyomma americanum* RXR homolog 1 ("AmaRXR1"), an invertebrate homolog of vertebrate RXR, and *Amblyomma americanum* RXR homolog 2 ("AmaRXR2"), an invertebrate homolog of vertebrate RXR. The prepared receptor constructs comprise a ligand binding domain of either an EcR, a vertebrate RXR, an invertebrate USP, or an invertebrate RXR; and a GAL4 or LexA DNA binding domain (DBD) or a VP16 or B42 acidic activator transactivation domain (AD). The reporter constructs include a reporter gene, luciferase or LacZ, operably linked to a synthetic promoter construct that comprises either a GAL4 response element or a LexA response element to which the Gal4 DBD or LexA DBD binds, respectively. Various combinations of these receptor and reporter constructs were cotransfected into mammalian cells as described in Examples 2-9 infra.

Gene Expression Cassettes: Ecdysone receptor-based gene expression cassettes (switches) were constructed as followed, using standard cloning methods available in the art. The following is brief description of preparation and composition of each switch used in the Examples described herein.

1.1—GAL4CfEcR-CDEF/VP16MmRXRα-DEF: The C, D, E, and F domains from spruce budworm *Choristoneura fumiferana* EcR ("CfEcR-CDEF"; SEQ ID NO: 45) were fused to a GAL4 DNA binding domain ("Gal4DNABD" or "Gal4 DBD"; SEQ ID NO: 33) and placed under the control of an SV40e promoter (SEQ ID NO: 46). The DEF domains from mouse (*Mus musculus*) RXRα ("MmRXRα-DEF"; SEQ ID NO: 47) were fused to the transactivation domain from VP16 ("VP16AD"; SEQ ID NO: 37) and placed under the control of an SV40e promoter (SEQ ID NO: 46). Five consensus GAL4 response element binding sites ("5XGAL4RE"; comprising 5 copies of a GAL4RE comprising SEQ ID NO: 41) were fused to a synthetic E1b minimal promoter (SEQ ID NO: 48) and placed upstream of the luciferase gene (SEQ ID NO: 49).

1.2—GAL4CfEcR-CDEF/VP16MmRXRα-EF: This construct was prepared in the same way as in switch 1.1 above except MmRXRα-DEF was replaced with MmRXRα-EF (SEQ ID NO: 50).

1.3—GAL4CfEcR-CDEF/VP16CfUSP-DEF: This construct was prepared in the same way as in switch 1.1 above except MmRXRα-DEF was replaced with the D, E and F domains from spruce budworm USP ("CfUSP-DEF"; SEQ ID NO: 51). The constructs used in this example are similar to those disclosed in U.S. Pat. No. 5,880,333 except that *Choristoneura fumiferana* USP rather than *Drosophila melanogaster* USP was utilized.

1.4—GAL4CfEcR-CDEF/VP16LmUSP-DEF: This construct was prepared in the same way as in switch 1.1 above except MmRXRα-DEF was replaced with the D, E and F domains of *Locusta migratoria* ultraspiracle ("LmUSP-DEF"; SEQ ID NO: 52).

1.5—GAL4CfEcR-DEF/VP16MmRXRα-DEF: This construct was prepared in the same way as switch 1.1 except CfEcR-CDEF was replaced with CfEcR-DEF (SEQ ID NO: 53).

1.6—GAL4CfEcR-DEF/VP16MmRXRα-EF: This construct was prepared in the same way as switch 1.5 except MmRXRα-DEF was replaced with MmRXRα-EF (SEQ ID NO: 50).

1.7—GAL4CfEcR-DEF/VP16CfUSP-DEF: This construct was prepared in the same way as in switch 1.5 above except MmRXRα-DEF was replaced with the D, E and F domains from spruce budworm *C. fumiferana* USP ("CfUSP-DEF"; SEQ ID NO: 51).

1.8—GAL4CfEcR-DEF/VP16LmUSP-DEF: This construct was prepared in the same way as in switch 1.5 above except MmRXRα-DEF was replaced with the D, E, and F domains of *Locusta migratoria* ultraspiracle ("LmUSP-DEF"; SEQ ID NO: 52).

1.9—Gal4CfEcR-A/BCDEF/VP16LmUSP-DEF: The full-length spruce budworm *Choristoneura fumiferana* EcR ("CfEcR-A/BCDEF"; SEQ ID NO: 54) was fused to a GAL4 DNA binding domain ("Gal4DNABD" or "Gal4 DBD"; SEQ ID NO: 33) and placed under the control of an SV40e promoter (SEQ ID NO: 46). The DEF domains from *Locusta migratoria* ultraspiracle ("LmUSP-DEF"; SEQ ID NO: 52) were fused to the transactivation domain from VP16 ("VP16AD"; SEQ ID NO: 37) and placed under the control of an SV40e promoter (SEQ ID NO: 46). Five consensus GAL4 response element binding sites ("5XGAL4RE"; comprising 5 copies of a GAL4RE comprising SEQ ID NO: 41) were fused to a synthetic E1b minimal promoter (SEQ ID NO: 48) and placed upstream of the luciferase gene (SEQ ID NO: 49).

1.10—Gal4CfEcR-1/2CDEF/VP16LmUSP-DEF: This construct was prepared in the same way as switch 1.9 except CfEcR-A/BCDEF was replaced with CfEcR-1/2CDEF (SEQ ID NO: 55).

1.11—Gal4CfEcR-CDEF/VP16LmUSP-DEF: This construct was prepared in the same way as switch 1.9 except CfEcR-A/BCDEF was replaced with CfEcR-CDEF (SEQ ID NO: 45).

1.12—Gal4CfEcR-DEF/VP16LmUSP-DEF: This construct was prepared in the same way as switch 1.9 except CfEcR-A/BCDEF was replaced with CfEcR-DEF (SEQ ID NO: 53).

1.13—Gal4CfEcR-EF/VP16LmUSP-DEF: This construct was prepared in the same way as switch 1.9 except CfEcR-A/BCDEF was replaced with CfEcR-EF (SEQ ID NO: 1).

1.14—Gal4CfEcR-DE/VP16LmUSP-DEF: This construct was prepared in the same way as switch 1.9 except CfEcR-CDEF was replaced with CfEcR-DE (SEQ ID NO: 3).

1.15—Gal4CfEcR-A/BCDEF/VP16LmUSP-EF: The full-length spruce budworm *Choristoneura fumiferana* EcR ("CfEcR-A/BCDEF"; SEQ ID NO: 54) was fused to a GAL4 DNA binding domain ("Gal4DNABD" or "Gal4 DBD"; SEQ ID NO: 33) and placed under the control of an SV40e promoter (SEQ ID NO: 46). The EF domains from *Locusta migratoria* ultraspiracle ("LmUSP-EF"; SEQ ID NO: 9) were fused to the transactivation domain from VP16 ("VP16AD"; SEQ ID NO: 37) and placed under the control of an SV40e promoter (SEQ ID NO: 46). Five consensus GAL4 response element binding sites ("5XGAL4RE"; comprising 5 copies of a GAL4RE comprising SEQ ID NO: 41) were fused to a synthetic E1b minimal promoter (SEQ ID NO: 48) and placed upstream of the luciferase gene (SEQ ID NO: 49).

1.16—Gal4CfEcR-1/2CDEF/VP16LmUSP-EF: This construct was prepared in the same way as switch 1.15 except CfEcR-A/BCDEF was replaced with CfEcR-1/2CDEF (SEQ ID NO: 55).

1.17—Gal4CfEcR-CDEF/VP16LmUSP-EF: This construct was prepared in the same way as switch 1.15 except CfEcR-A/BCDEF was replaced with CfEcR-CDEF (SEQ ID NO: 45).

1.18—Gal4CfEcR-DEF/VP16LmUSP-EF: This construct was prepared in the same way as switch 1.15 except CfEcR-A/BCDEF was replaced with CfEcR-DEF (SEQ ID NO: 53).

1.19—Gal4CfEcR-EF/VP16LmUSP-EF: This construct was prepared in the same way as switch 1.15 except CfEcR-A/BCDEF was replaced with CfEcR-EF (SEQ ID NO: 1).

1.20—Gal4CfEcR-DE/VP16LmUSP-EF: This construct was prepared in the same way as switch 1.15 except CfEcR-CDEF was replaced with CfEcR-DE (SEQ ID NO: 3).

1.21—Gal4CfEcR-DEF/VP16AmaRXR1-EF: This construct was prepared in the same way as switch 1.18 except LmUSP-EF was replaced with the E and F domains of ixodid tick *Amblyomma americanum* RXR homolog 1 ("AmaRXR1-EF"; SEQ ID NO: 10).

1.22—Gal4CfEcR-DEF/VP16AmaRXR2-EF: This construct was prepared in the same way as switch 1.21 except AmaRXR1-EF was replaced with the E and F domains of ixodid tick *Amblyomma americanum* RXR homolog 2 ("AmaRXR2-EF"; SEQ ID NO: 11).

1.23—LexACfEcR-CDEF/VP16CfUSP-EF: The C, D, E, and F domains from spruce budworm *Choristoneura fumiferana* EcR ("CfEcR-CDEF"; SEQ ID NO: 45) were fused to a LexA DNA binding domain ("LexADNABD" or "LexADBD"; SEQ ID NO: 35) and placed under the control of an SV40e promoter (SEQ ID NO: 46). The E and F domains from spruce budworm *C. fumiferana* USP ("CfUSP-EF"; SEQ ID NO: 56) were fused to the transactivation domain from VP16 ("VP16AD"; SEQ ID NO: 37) and placed under the control of an SV40e promoter (SEQ ID NO: 46). Eight consensus LexA response element binding sites ("8XLexAop"; comprising 4 copies of a LexA response element binding site comprising SEQ ID NO: 42) were fused to a synthetic E1b minimal promoter (SEQ ID NO: 48) and placed upstream of the luciferase gene (SEQ ID NO: 49).

1.24—LexACfEcR-CDEF/VP16LmUSP-EF: This construct was prepared in the same way as switch 1.23 except CfUSP-EF was replaced with LmUSP-EF (SEQ ID NO: 9).

1.25—LexACfEcR-CDEF/VP16MmRXRα-EF: This construct was prepared in the same way as switch 1.23 except CfUSP-EF was replaced with MmRXRα-EF (SEQ ID NO: 50).

1.26—LexACfEcR-CDEF/VP16DmUSP-EF: This construct was prepared in the same way as switch 1.23 except CfUSP-EF was replaced with the corresponding EF domains of DmUSP-EF (SEQ ID NO: 60).

1.27—Gal4CfEcR-CDEF/B42LmUSP-EF: The C, D, E, and F domains from spruce budworm *Choristoneura fumiferana* EcR ("CfEcR-CDEF"; SEQ ID NO: 45) were fused to a GAL4 DNA binding domain ("GAL4DNABD" or "GAL4 DBD"; SEQ ID NO: 33) and placed under the control of an SV40e promoter (SEQ ID NO: 46). The E and F domains from locust *Locusta migratoria* USP ("LmUSP-EF"; SEQ ID NO: 9) were fused to the transactivation domain from B42 ("B42AD"; SEQ ID NO: 39) and placed under the control of an SV40e promoter (SEQ ID NO: 46). Five consensus GAL4 response element binding sites ("5XGAL4RE"; comprising 5 copies of a GAL4RE comprising SEQ ID NO: 41) were fused to a synthetic E1b minimal promoter (SEQ ID NO: 48) and placed upstream of the luciferase gene (SEQ ID NO: 49).

1.28—LexACfEcR-CDEF/B42LmUSP-EF: This construct was prepared in the same way as switch 1.27 except the GAL4 DNA binding domain was replaced with a LexA DNA binding domain (SEQ ID NO: 35).

1.29—GAL4CfEcR-DEF/VP16DmUSP-EF: This construct was prepared in the same way as switch 1.7 except CfUSP-DEF was replaced with the corresponding EF domains of DmUSP-EF (SEQ ID NO: 60).

1.30—GAL4CfEcR-DEF/VP16CfUSP-EF: This construct was prepared in the same way as switch 1.7 except CfUSP-DEF was replaced with CfUSP-EF (SEQ ID NO: 56).

Example 2

In a two-hybrid switch format, CfUSP and DmUSP in partnership with CfEcR are constitutively active in both yeast and mammalian cells. On the other hand, vertebrate RXR in partnership with CfEcR is a ligand dependent transactivator in mammalian cells. Applicants tested an invertebrate RXR, LmUSP in a two-hybrid format in mouse NIH3T3 cells to determine if it would function as a USP (constitutively) or as a vertebrate RXR (inducibly) in mammalian cells. Gal4:CfEcR-CDEF (FIG. 1) or Gal4:CfEcR-DEF (FIG. 2) were paired with VP16:MmRXR-DEF; VP16:MmRXR-EF; VP16:LmUSP-DEF; or VP16:CfUSP-EF and analyzed in mammalian cells. Briefly, gene induction potential (magnitude of induction) and ligand specificity and sensitivity were examined using two different ligands: a steroidal ligand (Ponasterone A, "PonA") and a non-steroidal ligand [N-(2-ethyl-3-methoxybenzoyl)-N'-(3,5-dimethylbenzoyl)-N-tert-butylhydrazine] in a dose-dependent induction of reporter gene expression in the transfected NIH3T3 cells. Reporter gene expression activities were assayed at 48 hours after ligand addition. Standard methods for culture and maintenance of the cells were followed.

Transfections: DNAs corresponding to the various switch constructs outlined in Example 1, specifically switches 1.1 through 1.8, were transfected into mouse NIH3T3 cells (ATCC) as follows. Cells were harvested when they reached 50% confluency and plated in 6-, 12- or 24-well plates at 125,000, 50,000, or 25,000 cells, respectively, in 2.5, 1.0, or 0.5 ml of growth medium containing 10% fetal bovine serum (PBS), respectively. The next day, the cells were rinsed with growth medium and transfected for four hours. Superfect™ (Qiagen Inc.) was found to be the best transfection reagent for 3T3 cells. For 12-well plates, 4 μl of Superfect™ was mixed with 100 μl of growth medium. 1.0 μg of reporter construct and 0.25 μg of each receptor construct of the receptor pair to be analyzed were added to the transfection mix. A second reporter construct was added [pTKRL (Promega), 0.1 μg/transfection mix] that comprises a *Renilla* luciferase gene operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 400 μl growth medium. The cells were maintained at 37° C. and 5% $CO_2$ for four hours. At the end of incubation, 500 μl of growth medium containing 20% FBS and either dimethylsulfoxide (DMSO; control) or a DMSO solution of 0.1, 1, 5, 10, and 50 μM PonA steroidal ligand or N-(2-ethyl-3-methoxybenzoyl)N'-(3,5-dimethylbenzoyl)-N'-tert-butylhydrazine non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and reduced to half for 24-well plates.

Ligands: The steroidal ligand Ponasterone A (PonA) was purchased from Sigma Chemical Company. The non-steroidal ligand N-(2-ethyl-3-methoxybenzoyl)-N'-(3,5-dimethylbenzoyl)-N'-t-butylhydrazine (GS™-E non-steroidal ligand) is a synthetic stable ecdysteroid ligand synthesized at Rohm and Haas Company. All ligands were dissolved in DMSO and the final concentration of DMSO was maintained at 0.1% in both controls and treatments.

Reporter Assays: Cells were harvested 48 hours after adding ligands. 125, 250, or 500 μl of passive lysis buffer (part of Dual-luciferase™ reporter assay system from Promega Corporation) were added to each well of 24- or 12- or 6-well plates respectively. The plates were placed on a rotary shaker for 15 minutes. Twenty μl of lysate were assayed. Luciferase activity was measured using Dual-luciferase™ reporter assay system from Promega Corporation following the manufacturer's instructions. 13-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control).

Figure 2:
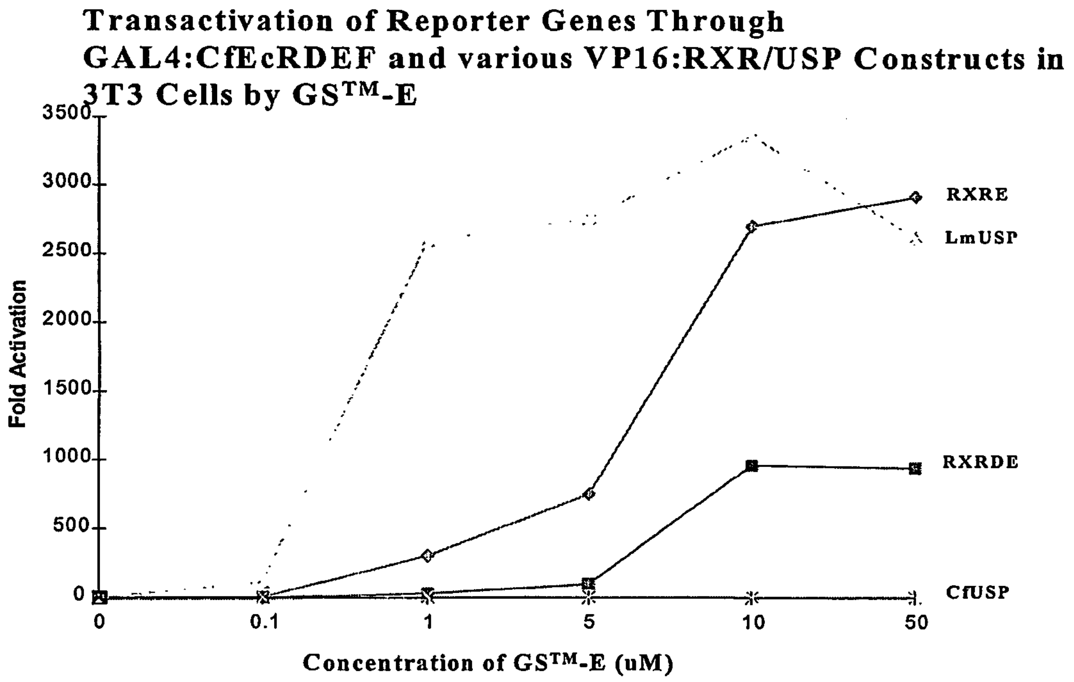
FIG. 2: Transactivation of reporter genes through VP16MmRXRDEF, VP16MmRXREF, VP16LmUSP, and VP16CfUSP constructs transfected into NIH3T3 cells along with GAL4CfEcRDEF, pFRLuc and pTKRL plasmid DNAs by a non-steroidal ligand.
Figure 4:
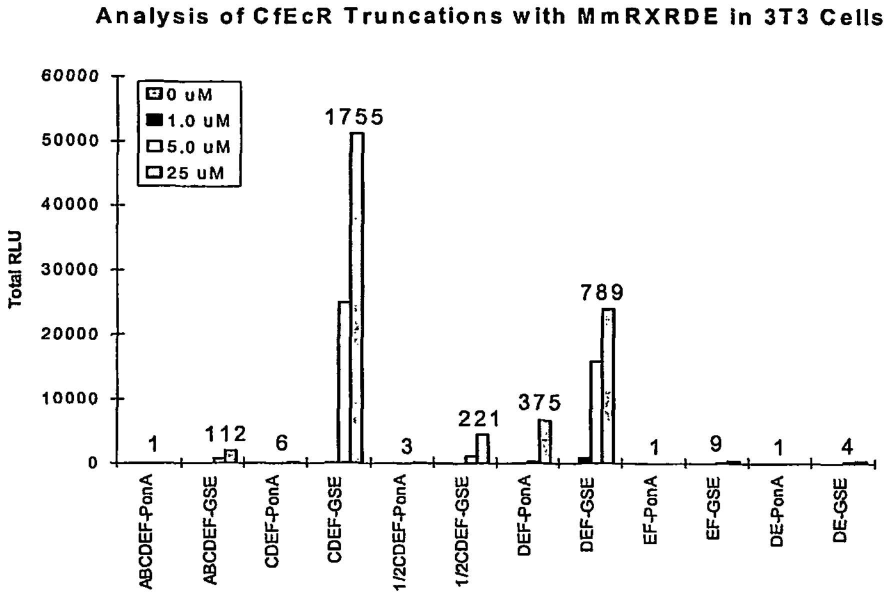
FIG. 4: Expression data of various truncations of CfEcR, GAL4CfEcRA/BCDEF, GAL4CfEcRCDEF, GAL4CfEcR1/2CDEF, GAL4CfEcRDEF, GAL4CfEcREF, GAL4CfEcRDE transfected into NIH3T3 cells along with VP16MmRXRDEF, pFRLUc and pTKRL plasmid DNAs in the presence of non-steroidal ligand or PonA ligand.
Figure 5:
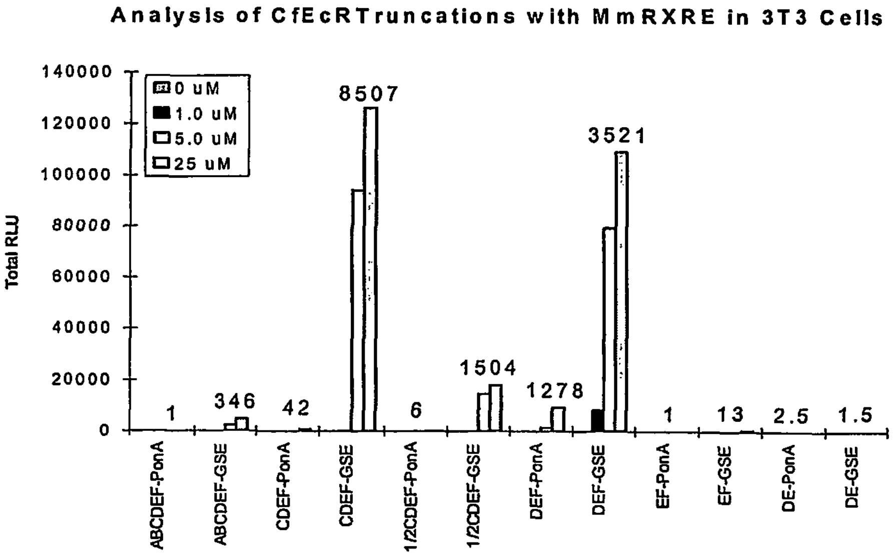
FIG. 5: Expression data of various truncations of CfEcR, GAL4CfEcRA/BCDEF, GAL4CfEcRCDEF, GAL4CfEcR1/2CDEF, GAL4CfEcRDEF, GAL4CfEcREF, GAL4CfEcRDE transfected into NIH3T3 cells along with VP16MmRXREF, pFRLUc and pTKRL plasmid DNAs in the presence of non-steroidal ligand or PonA ligand.

Results: As shown in FIGS. 1 and 2, LmUSP in partnership with CfEcR functions as a ligand-inducible gene expression system in mammalian cells. This result is surprising since Applicants' previous experiments with CfUSP and DmUSP in partnership with CfEcR demonstrated constitutive expression activity (see PCT/US01/09050 application and FIGS. 1 and 2 for CfUSP results; DmUSP results are not shown). In addition, LmUSP worked better than vertebrate RXR as a CfEcR partner. In particular, both the sensitivity, i.e. the concentration of ligand required for transactivation, and the magnitude of transactivation were increased with LmUSP compared to vertebrate RXR. Thus, Applicants have demonstrated for the first time that invertebrate RXRs can function effectively in partnership with an ecdysone receptor in an inducible gene expression system in mammalian cells.

This EcR/invertebrate RXR inducible gene expression system is an improvement over the EcR/vertebrate RXR gene expression system since less ligand is required for transactivation and increased levels of transactivation can be achieved.

Based upon Applicant's discovery described herein, one of ordinary skill in the art is able to predict that other invertebrate RXRs and their homologs, with the exception of Dipteran RXR homologs (example DmUSP) and Lepidopteran RXR homologs (example CfUSP), will also function in Applicants' EcR/invertebrate RXR-based inducible gene expression system. In addition, one of ordinary skill in the art is also able to predict that Applicants' novel inducible gene expression system will also work to modulate gene expression in yeast cells. Since the Dipteran RXR homolog/ and Lepidopteran RXR homolog/EcR gene expression systems function constitutively in yeast cells (data not shown), similar to how they function in mammalian cells, and Applicants have shown herein that non-Dipteran and non-Lepidopteran invertebrate RXRs function inducibly in partnership with an EcR in mammalian cells, the EcR/invertebrate RXR-based gene expression system is also predicted to function inducibly in yeast cells. Thus, the EcR/invertebrate RXR inducible gene expression system of the present invention is useful in applications where modulation of gene expression levels is desired in both yeast and mammalian cells. Further, there is no reason not to expect that the present invention would also work in other cells.

Example 3

This Example describes the comparison of vertebrate RXR and invertebrate RXR-based two-hybrid gene expression systems comprising full length or truncated EcR, vertebrate RXR, and invertebrate RXR polypeptides. An amino acid sequence alignment, comparing the EF domains of twelve different vertebrate and invertebrate RXRs is shown in FIGS. 3A and B. As described below, Applicants compared different GAL4/CfEcR-based switches comprising MmRXRα-EF (a vertebrate RXR), LmUSP-EF (an invertebrate RXR), AmaRXR1-EF (an invertebrate RXR), and AmaRXR2-EF (an invertebrate RXR) fused to a VP16 activation domain to identify the receptors that give a switch with a) maximum induction in the presence of ligand; b) minimum background in the absence of ligand; c) highly sensitive to ligand concentration; and/or d) minimum cross-talk among ligands and receptors in mammalian cells.

Briefly, full-length EcR and truncated EcRs, created by a truncation mutation at the junctions of A/B, C, D, E and F domains and fused to a GAL4 DNA binding domain encoding polynucleotide (SEQ ID NO: 33) as described in Example 1 above. A VP16 activation domain encoding polynucleotide (SEQ ID NO: 37) was fused to the E and F domains of MmRXRα, LmUSP, AmaRXR1, and AmaRXR2 as described in Example 1. The resulting hybrid EcR/vertebrate or invertebrate RXR-encoding gene expression cassettes were assayed in NIH3T3 cells in pairwise comparisons. Plasmid pFRLUC (Stratagene) encoding a luciferase polypeptide was used as a reporter gene construct and pTKRL (Promega) encoding a *Renilla* luciferase polypeptide under the control of the constitutive TK promoter was used to normalize the transfections as described above. The transfected cells were grown in the presence 0, 1, 5 or 25 μM of the non-steroid N-(2-ethyl-3-methoxybenzoyl)-N'-(3,5-dimethylbenzoyl)-N'-tert-butylhydrazine or the steroid PonA for 48 hours. The cells were harvested, lysed and luciferase reporter activity was measured in the cell lysates. Total fly luciferase relative light units are presented. The number on the top of each bar is the maximum fold induction for that treatment. The analysis was performed in triplicate and mean luciferase counts [total relative light units (RLU)] were determined as described above.

As shown in the FIGS. 4-7, CfEcR-CDEF performs better than any other CfEcR truncation. In particular, Gal4CfEcR-CDEF showed better induction than Gal4CfEcR-DEF using VP16LmUSP-EF. The EF domain of CfEcR in combination with LmUSP-DEF showed fairly good induced levels with very low uninduced levels. Most of EcR-EF domains described in patents and publications include D, E, and F domains (about 300 amino acids). This particular truncation includes only 230 amino acids and may rely on the D domain of LmUSP for heterodimerization.

Figure 6:
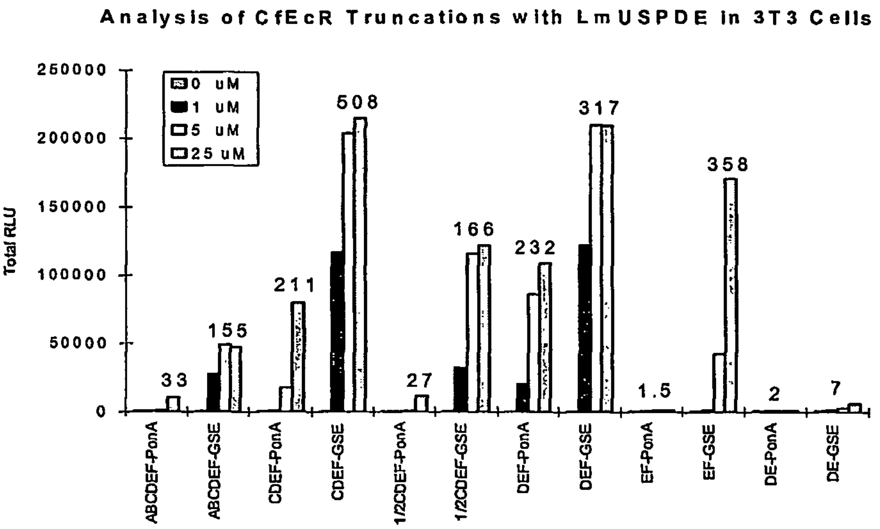
FIG. 6: Expression data of various truncations of CfEcR, GAL4CfEcRA/BCDEF, GAL4CfEcRCDEF, GAL4CfEcR1/2CDEF, GAL4CfEcRDEF, GAL4CfEcREF, GAL4CfEcRDE transfected into NIH3T3 cells along with VP16LmUSPDEF, pFRLUc and pTKRL plasmid DNAs in the presence of non-steroidal ligand or PonA ligand.
Figure 7:
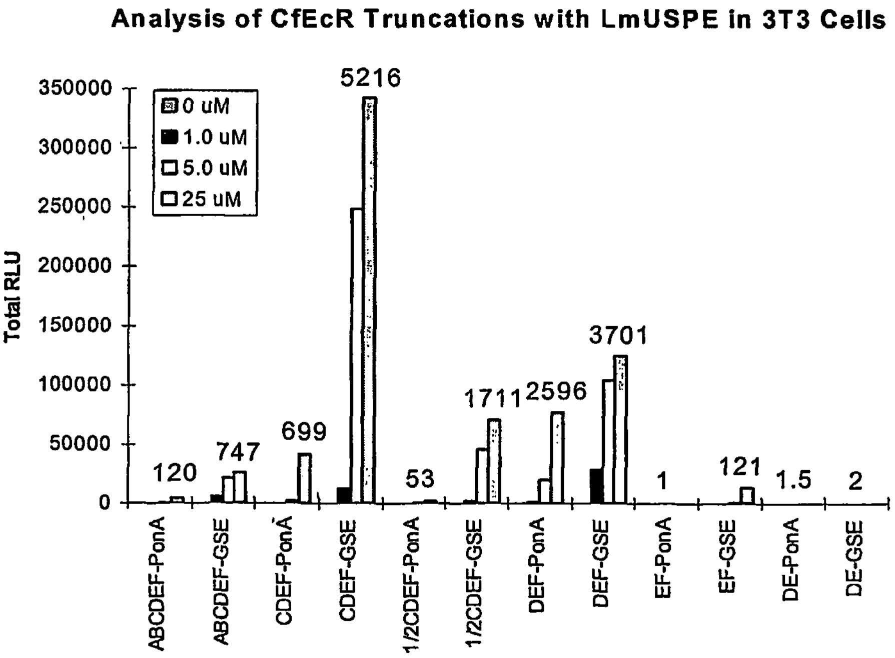
FIG. 7: Expression data of various truncations of CfEcR, GAL4CfEcRA/BCDEF, GAL4CfEcRCDEF, GAL4CfEcR1/2CDEF, GAL4CfEcRDEF, GAL4CfEcREF, GAL4CfEcRDE transfected into NIH3T3 cells along with VP16LmUSPEF, pFRLUc and pTKRL plasmid DNAs in the presence of non-steroidal ligand or PonA ligand.

Of all the truncations of LmUSP tested, Applicants' results show that the VP16LmUSP-EF hybrid receptor polypeptide was the best partner for Gal4CfEcR-based hybrid polypeptides, with GAL4CfEcRCDEF/VP16LmUSP-EF (switch 1.17) performing better than any other receptor combination and more sensitive to non-steroids than steroids (FIGS. 6 and 7). In general, the CfEcR/LmUSP-based switch was more sensitive to the non-steroid N-(2-ethyl-3-methoxybenzoyl)-N'-(3,5-dimethylbenzoyl)-N'-tert-butylhydrazine than to the steroid PonA. Thus, the EF domain of LmUSP is sufficient and performs better than DEF domains of this receptor in partnership with CfEcR constructs.

Applicants' results show that the magnitude and fold induction of MmRXRα and LmUSP are similar but LmUSP improves sensitivity to ligand by at least 10 fold. Thus, the EcR/invertebrate system is an improvement over the EcR/vertebrate system.

Example 4

This Example describes Applicants' further analysis of gene expression cassettes encoding truncated EcR or RXR receptor polypeptides that affect either ligand binding activity or ligand sensitivity, or both. Briefly, eleven different combinations of two-hybrid receptor pairs, constructed as described in Example 1, were further analyzed in a single experiment in NIH3T3 cells. These eleven receptor pair combinations and their corresponding sample numbers are depicted in Table 1.

TABLE 1

CfEcR + MmRXRα/LmUSP Truncation Receptor Combinations in NIH3T3 Cells

Figure 8:
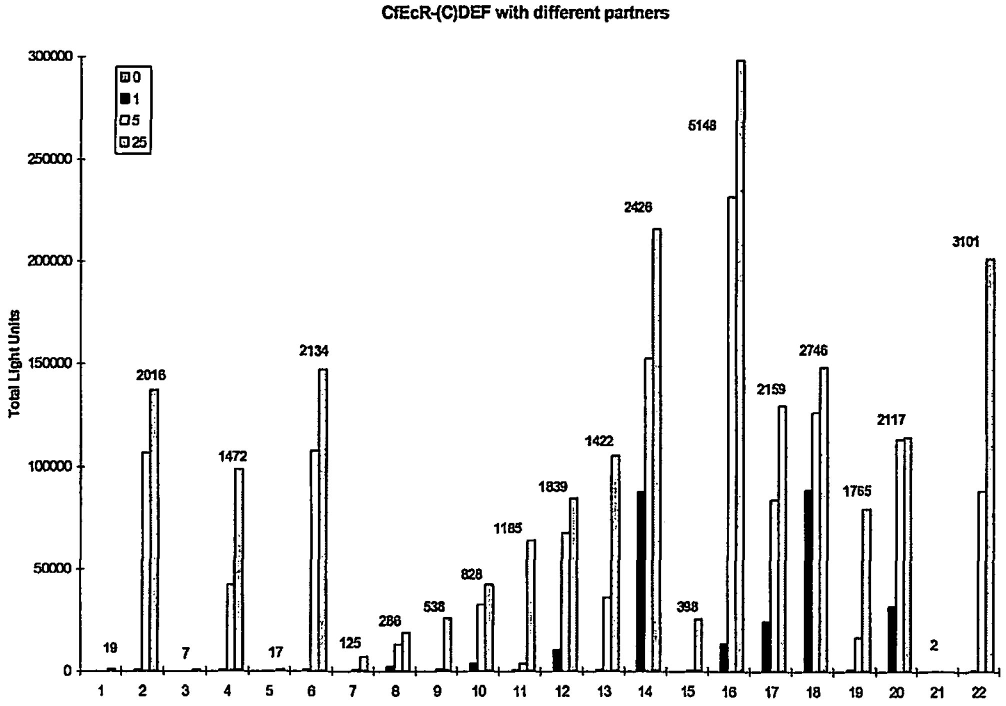
FIG. 8: Expression data of various truncated MmRXR/LmUSP receptor constructs transfected into NIH3T3 cells along with GAL4CfEcRDEF, pFRLUc and pTKRL plasmid DNAs in the presence of non-steroidal ligand or PonA ligand.

| FIG. 8 X-Axis Sample No. | CfEcR Polypeptide Construct | MmRXRα or LmUSP Polypeptide Construct |
|---|---|---|
| Samples 1 and 2 | GAL4CfEcR-CDEF | VP16MmRXRα-A/BCDEF |
| Samples 3 and 4 | GAL4CfEcR-CDEF | VP16MmRXRα-DEF |
| Samples 5 and 6 | GAL4CfEcR-CDEF | VP16MmRXRα-EF |
| Samples 7 and 8 | GAL4CfEcR-DEF | VP16MmRXRα-A/BCDEF |
| Samples 9 and 10 | GAL4CfEcR-DEF | VP16MmRXRα-DEF |
| Samples 11 and 12 | GAL4CfEcR-DEF | VP16MmRXRα-EF |
| Samples 13 and 14 | GAL4:CfEcR-CDEF | VP16:LmUSP-DEF |
| Samples 15 and 16 | GAL4:CfEcR-CDEF | VP16:LmUSP-EF |
| Samples 17 and 18 | GAL4:CfEcR-DEF | VP16:LmUSP-DEF |
| Samples 19 and 20 | GAL4:CfEcR-DEF | VP16:LmUSP-EF |
| Samples 21 and 22 | GAL4:CfEcR-EF | VP16:LmUSP-DEF |

The above receptor construct pairs, along with the reporter plasmid pFRLuc were constructed as described above and transfected into NIH3T3 cells as described above. The eleven CfEcR truncation receptor combinations were duplicated into two groups and treated with either steroid (odd numbers on x-axis of FIG. 8) or non-steroid (even numbers on x-axis of FIG. 8). In particular, the cells were cultured in media containing 0, 1, 5 or 25 uM PonA (steroid) or N-(2-ethyl-3-methoxybenzoyl)-N'-(3,5-dimethylbenzoyl)-N'-tert-butylhydrazine (non-steroid) ligand. The reporter gene activity was measured and total RLU are shown. The number on top of each bar is the maximum fold induction for that treatment and is the mean of three replicates.

As shown in FIG. 8, the CfEcR-CDEF/LmUSP-EF receptor combination (columns 15 and 16) was the best format both in terms of total RLU and fold induction. This result is consistent with Applicants' results presented above in Example 3. These eleven receptor pair combinations were also assayed in a human lung carcinoma cell line A549 (ATCC) and similar results were observed (data not shown).

Example 5

This Example describes Applicants' analysis of additional invertebrate retinoid X receptor homologs for use within the EcR/invertebrate RXR-based inducible gene expression system of the present invention. Briefly, two-hybrid receptor gene switches were constructed as described in Example 1 comprising a GAL4/CfEcR-DEF gene expression cassette and VP16AmaRXR1-EF or a VP16AmaRXR2-EF. These AmaRXR1- and AmaRXR2-based gene switches (switches 1.21 and 1.22 of Example 1) were compared to GAL4/CfEcR-DEF gene switches comprising VP16MmRXRα-EF (switch 1.6), VP16LmUSP-EF (switch 1.18), VP16DmUSP-EF (switch 1.29), and VP16CfUSP-EF (switch 1.30) along with pFRLuc in NIH3T3 cells.

The above receptor construct pairs, along with the reporter plasmid pFRLuc were constructed as described above and transfected into NIH3T3' cells as described above. The transactivation potential of these six CfEcR-DEF receptor-based gene switches were determined in the transfected cells in the presence of 0, 0.2, 1, or 10 μM PonA (steroid) or 0, 0.4, 0.2, 1, or 10 μM non-steroid ligand N-(2-ethyl-3-methoxybenzoyl)-N'-(3,5-dimethylbenzoyl)-N'-tert-butylhydrazine. The reporter gene activity was measured and total RLU are shown. The number on top of each bar is the maximum fold induction for that treatment and is the mean of three replicates.

Figure 9:
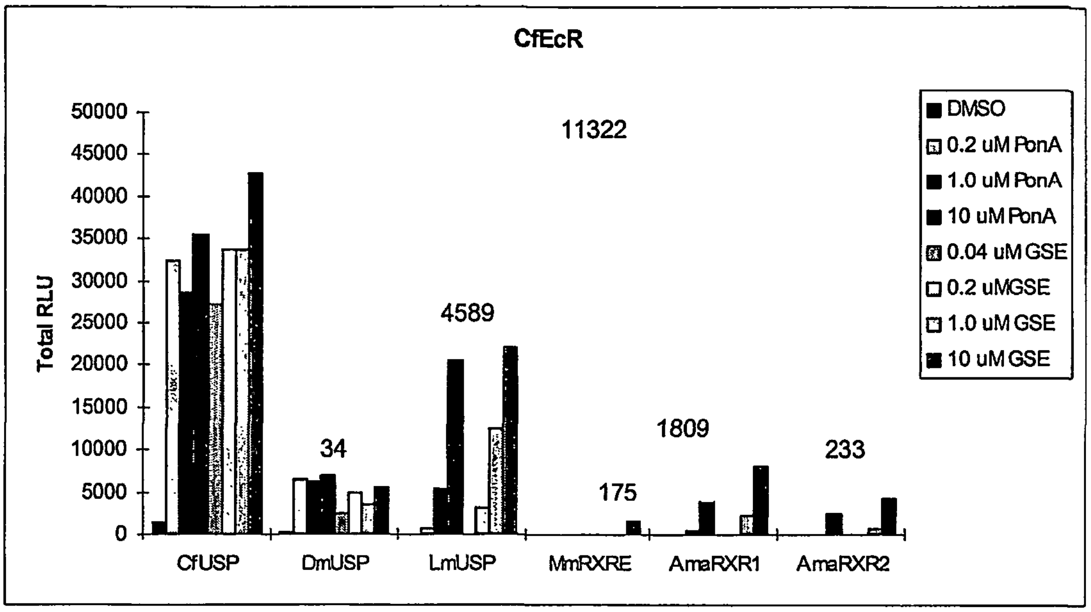
FIG. 9: Expression data of CfUSP-EF, DmUSP-EF, LmUSP-EF, MmRXRα-EF, AmaRXR1-EF and AmaRXR2-EF ligand binding domains fused to VP16 along with GAL4/CfEcR-DEF and pFRLuc in NIH3T3 cells in the presence of non-steroidal (GSE) ligand or PonA ligand.

As shown in FIG. 9, both AmaRXR1-EF and AmaRXR2-EF based switches performed better than the vertebrate MmRXRα-EF based switch, demonstrating that these non-dipteran, non-lepidopteran invertebrate RXR homologs can also function in the EcR/invertebrate RXR-based inducible gene expression system of the present invention. Thus, based upon Applicants' surprising discovery that an invertebrate RXR (LmUSP) can substitute for a vertebrate RXR and the findings borne out in this Example regarding additional invertebrate species RXRs, one of ordinary skill in the art is able to predict that other invertebrate species, non-dipteran and non-lepidopteran RXR homologs will work in Applicant's gene expression system.

Example 6

This Example describes the construction of host cells comprising the EcR/invertebrate RXR-based gene expression modulation system according to the invention. To make stable cells expressing GAL4:CfEcR-DEF/VP16:LmUSP-EF (switch 1.18, prepared as described in Example 1), Applicants transfected the gene expression cassettes encoding the hybrid GAL4:CfEcR-DEF and VP16:LmUSP-EF polypeptides into Chinese hamster ovary CHO cells comprising a stably transfected reporter plasmid pFRLuc. Briefly, CHO cells were harvested when they reach 60-80% confluency and plated in 6- or 12- or 24-well plates at 250,000, 100,000, or 50,000 cells in 2.5, 1.0, or 0.5 ml of growth medium containing 10% Fetal bovine serum respectively. The next day, the cells were rinsed with growth medium and transfected for four hours. LipofectAMINE™ 2000 (Life Technologies Inc,) was found to be the best transfection reagent for these cells. For 12-well plates, 4 μl of LipofectAMINE™ 2000 was mixed with 100 μl of growth medium. 1.0 μg of reporter construct and 0.25 μg of each receptor construct GAL4:CfEcR-DEF and VP16:LmUSP-EF were added to the transfection mix. A second reporter construct was added (0.1 μg/transfection mix) and comprised a *Renilla* luciferase gene operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 400 μl growth medium. The cells were maintained at 37° C. and 5% $CO_2$ for four hours. At the end of incubation, 500 μl of growth medium containing 20% FBS and either DMSO (control) or a DMSO solution of appropriate ligands were added and the cells were maintained at 37° C. and 5% $CO_2$ for 24-48 hr. The cells were harvested and reporter activity was assayed. The same procedure was followed for 6 and 24 well plates as well except all the reagents were doubled for 6 well plates and reduced to half for 24-well plates.

The transfected CHO cells were grown in the presence of 0, 1, 5, or 25 μM PonA steroid ligand or GS™-E non-steroid ligand for 48 hours. The cells were harvested, lysed and the reporter activity was measured. Total fly luciferase relative light units (RLU) are presented. The numbers on the top of the bars correspond to the maximum fold induction for each treatment. Bulk populations of cells were selected for resistance to the antibiotic neomycin (VP16:LmUSP/VP16:RXR constructs have the neomycin resistance gene incorporated). Several clones from each population were isolated by end point dilution. Three clones of stably transfected GAL4:CfEcR-DEF/VP16:LmUSP-EF cells were analyzed (see FIG. 10, clone 1A2; the data related to the two other clones are not shown).

Figure 10:
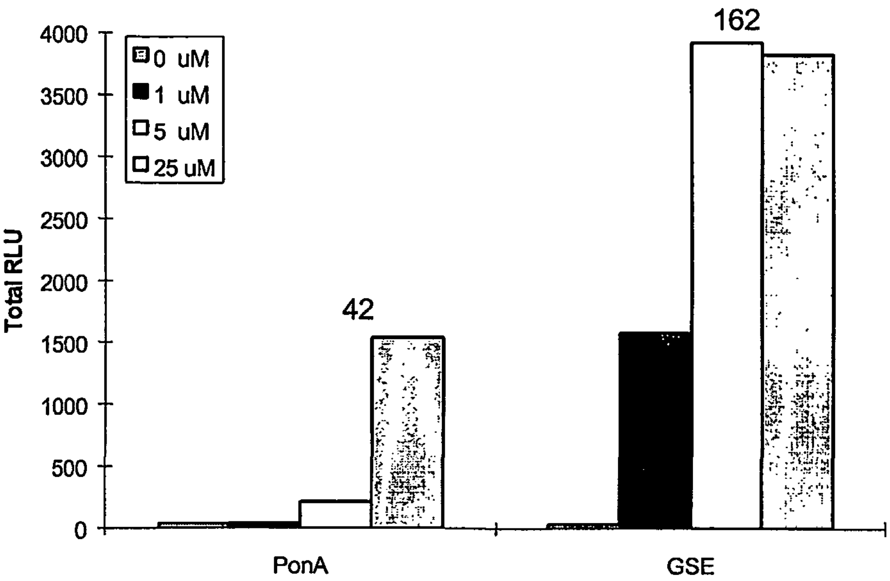
FIG. 10: Expression data of GAL4:CfEcR-DEF/VP16:LmUSP-EF in stably transfected CHO cells comprising a reporter plasmid pFRLuc in the presence of non-steroidal ligand or PonA ligand.

Of the three clones analyzed, the GAL4:CfEcR-DEF/VP16:LmUSP-EF stable clone 1A2 exhibited the highest fold induction, 162 fold, in the presence of non-steroidal ligand and 42 fold induction in the presence of steroid PonA (see FIG. 10).

Example 7

This Example describes the development of another embodiment of the EcR/invertebrate RXR gene expression modulation system of the invention. Specifically, Applicants have constructed LexA DNA binding domain (DBD) based-EcR/invertebrate RXR gene switches for use in the gene expression modulation system of the invention. This embodiment can be useful as an alternate switch for a GAL4 DBD-based switch and can also be used in multiple switch formats. While the LexA DBD has been used in yeast and plant expression systems, Applicants are not aware of its use in mammalian applications.

Briefly, a gene expression cassette comprising the LexA DNA binding domain (SEQ ID NO: 35) fused to CfEcR-CDEF domains (SEQ ID NO: 45) was prepared as described in Example 1. The LexA:CfEcR-CDEF gene expression cassette, along with a VP16:MmRXRα-EF, a VP16:CfUSP-EF, a VP16:DmUSP-EF, or a VP16:LmUSP-EF gene expression cassette, and a reporter construct (8opFRLuc) comprising an 8XLexA operator (4 copies of LexA response element; SEQ ID NO: 42), a minimal promoter (synthetic E1b minimal promoter SEQ ID NO: 48), and a luciferase gene (SEQ ID NO: 49) were transfected into mouse NIH3T3 cells. The transfected cells were cultured in the presence of 0, 0.1, 1, 5, 10, and 50 μM GS™-E non-steroidal ligand or PonA steroid ligand for 48 hours as described above. The cells were harvested, lysed and reporter activity was measured and total relative light units (RLU) are presented in FIG. 11. The number on the top of each bar corresponds to the maximum fold induction of each treatment.

Figure 11:
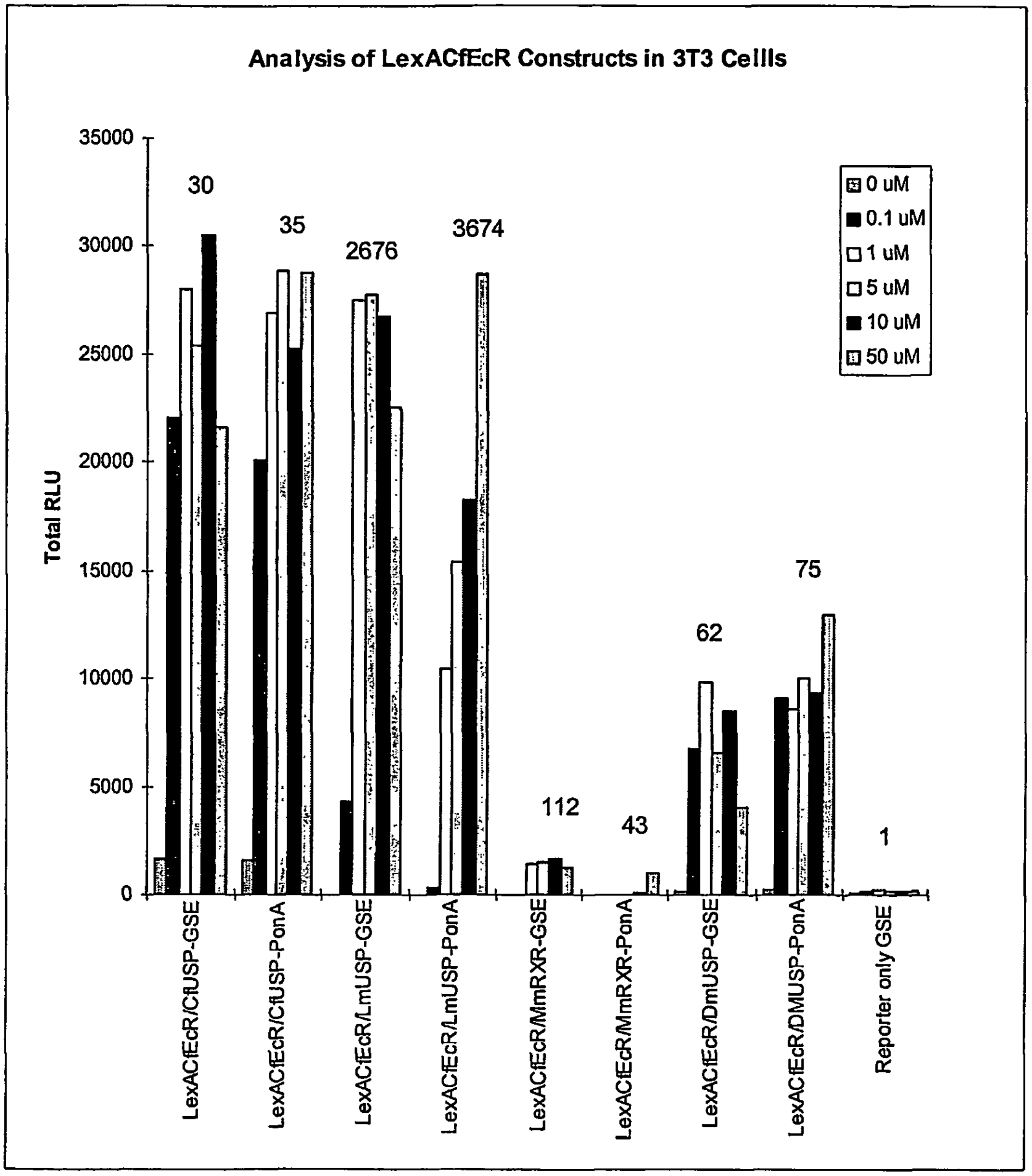
FIG. 11: Expression data of a LexA:CfEcR-CDEF receptor construct transfected into NIH3T3 cells along with 8XLexAopFRLuc and VP16:CfUSP-EF, VP16:LmUSP-EF, VP16:MmRXRα-EF or VP16:DmUSP-EF in the presence of non-steroidal ligand or PonA ligand.

The LexA:CfEcR-DEF construct functioned well in these mammalian cells with all partners examined (see FIG. 11). The fold induction is comparable to what was observed with Applicants' GAL4 system (see FIG. 4). The 8opFRLuc reporter (control) showed very little activity in these cells. The results presented in FIG. 11 show that the LexA DNA binding domain functions well in Applicants' two-hybrid system, demonstrating that the DNA binding domain is portable in these gene expression cassettes.

Example 8

This Example describes the development of another embodiment of the EcR/invertebrate RXR gene expression modulation system of the invention. Specifically, Applicants have constructed gene expression cassettes for use in the gene modulation system of the invention comprising a B42 acidic activator domain as a transactivation domain. The B42 acidic activator domain ("B42AD"; see Gyuris et al., (1993) Cell 75: 791-803) works well as a transactivator in yeast and as Applicants have now shown, works well in mammalian cells. The B42 acidic activator domain may be used in the gene expression cassettes of the present invention as an alternative to VP16 transactivation domain.

Figure 12:
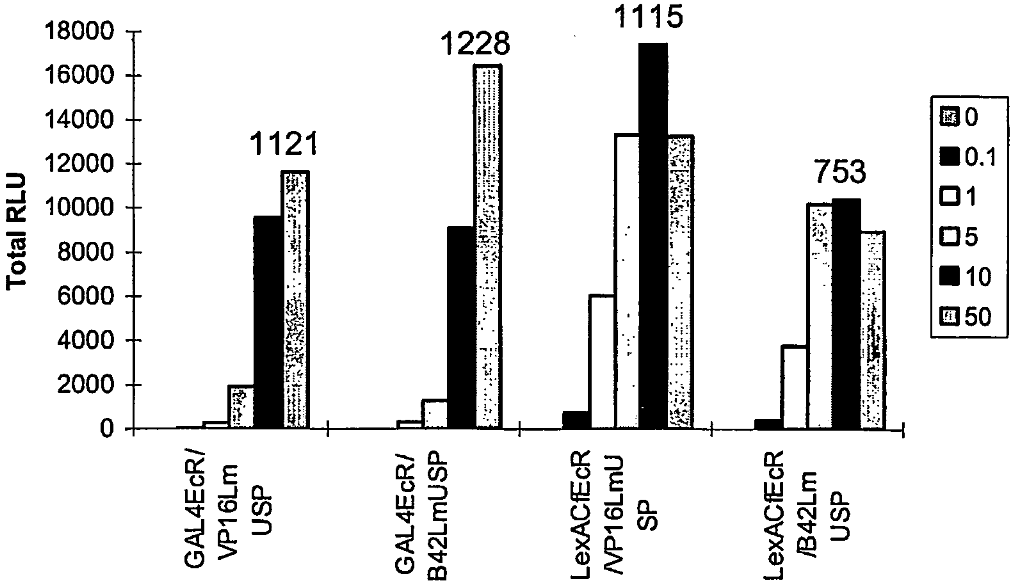
FIG. 12: NIH3T3 cells were transfected with different combinations of GAL4:CfEcR-CDEF or LexA:CfEcR-CDEF, 8XLexAopFRLuc and VP16:LmUSP-EF or B42:LmUSP-EF in the presence of non-steroidal ligand.

Briefly, Applicants have constructed a gene expression cassette comprising a polynucleotide encoding a B42AD (SEQ ID NO: 39) fused to a polynucleotide encoding LmUSP-EF domains (SEQ ID NO: 9) as described in Example 1. This B42AD:LmUSP-EF gene expression cassette was evaluated in mouse NIH3T3 cells in partnership with either a GAL4:CfEcR-CDEF or a LexA:CfEcR-CDEF gene expression cassette and compared to a VP16:LmUSP-EF-based switch. All gene expression cassettes were prepared as described in Example 1. The appropriate reporter constructs were transfected into NIH3T3 cells. The transfected cells were cultured in the presence of 0, 0.1, 1, 5, 10, and 50 μM GS™-E non-steroidal ligand for 48 hours as described above. Reporter activity is plotted as total RLU (see FIG. 12). The numbers on the top of the bars correspond to the maximum fold induction observed for that combination.

The results show that the B42 acidic activation domain works as well as the VP16 transactivation domain in Applicants' two-hybrid system, demonstrating that the transactivation domain is also portable in these gene expression cassettes.

Example 9

This Example demonstrates the effect of introduction of a second ligand into the host cell comprising an EcR/invertebrate RXR-based inducible gene expression modulation system of the invention. In particular, Applicants have determined the effect of 9-cis-retinoic acid on the transactivation potential of the GAL4CfEcR-DEF/VP16LmUSP-EF (switch 1.18) gene switch along with pFRLuc in NIH3T3 cells in the presence of non-steroid (GSE) for 48 hours.

Briefly, GAL4CfEcR-DEF, pFRLuc and VP16LmUSP-EF were transfected into NIH3T3 cells and the transfected cells were treated with 0, 0.04, 0.2, 1, 5 and 25 μM non-steroidal ligand (GSE) and 0, 1, 5 and 25 μM 9-Cis-retinoic acid (Sigma Chemical Company). The reporter activity was measured at 48 hours after adding ligands.

Figure 13:
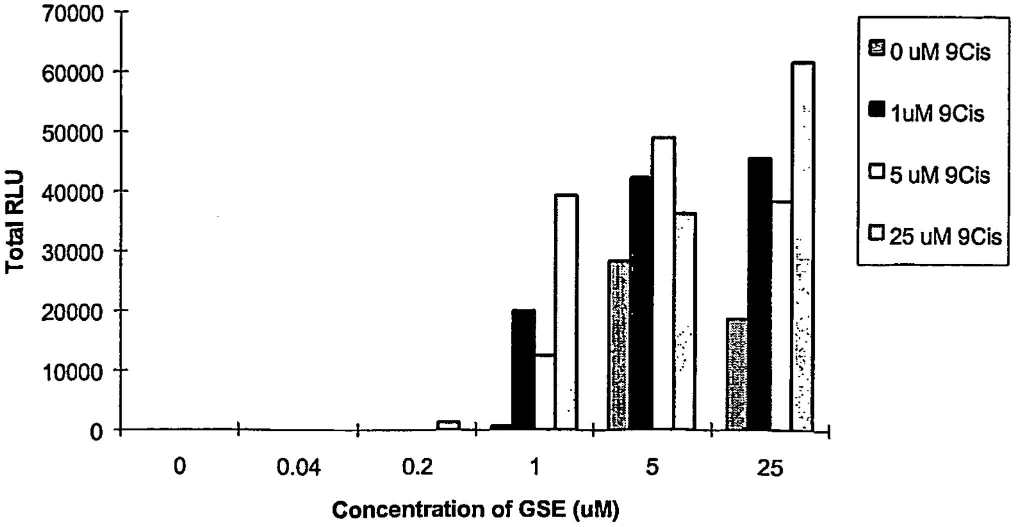
FIG. 13: Effect of 9-cis-retinoic acid on transactivation potential of the GAL4CfEcR-DEF/VP16LmUSP-EF gene switch along with pFRLuc in NIH 3T3 cells in the presence of non-steroid (GSE) and 9-cis-retinoic acid (9Cis) for 48 hours.

As shown in FIG. 13, the presence of retinoic acid increased the sensitivity of CfEcR-DEF to non-steroidal ligand. At a non-steroid ligand concentration of 1 μM or less, there is very little induction in the absence of 9-Cis-retinoic acid, but when 1 μM 9-Cis-retinoic acid is added in addition to non-steroid, induction is greatly increased.

We claim:

1. A viral vector comprising a gene expression modulation system comprising:

a) a first gene expression cassette that is capable of being expressed in a host cell, comprising a polynucleotide that encodes a first hybrid polypeptide comprising a DNA-binding domain that recognizes a response element associated with a gene whose expression is to be modulated; and b) a second gene expression cassette that is capable of being expressed in the host cell comprising a polynucleotide that encodes a second hybrid polypeptide comprising a transactivation domain, wherein said first hybrid polypeptide or said second hybrid polypeptide further comprises an ecdysone receptor ligand binding domain comprising an amino acid sequence selected from the group consisting of SEQ ID NO: 5, SEQ ID NO: 43, and SEQ ID NO: 59, and wherein said first hybrid polypeptide or said second hybrid polypeptide that does not comprise said ecdysone receptor ligand binding domain further comprises a retinoid X receptor ligand binding domain comprising an amino acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

2. The viral vector according to claim 1, said gene expression modulation system further comprising a third gene expression cassette comprising:

i) a response element recognized by the DNA-binding domain of the first hybrid polypeptide;

ii) a promoter that is activated by the transactivation domain of the second hybrid polypeptide; and iii) a gene whose expression is to be modulated.

3. The viral vector according to claim 1, wherein the ecdysone receptor ligand binding domain is encoded by a nucleic acid sequence selected from the group consisting of SEQ ID NO: 1, SEQ ID NO: 53, and SEQ ID NO: 45.

4. The viral vector according to claim 1, wherein the retinoid X receptor ligand binding domain is encoded by a polynucleotide comprising a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

5. The viral vector according to claim 1, wherein the DNA-binding domain is selected from the group consisting of a GAL4 DNA-binding domain, a LexA DNA-binding domain, and an ecdysone receptor ligand binding domain.

6. The viral vector according to claim 1, wherein the transactivation domain is selected from the group consisting of a VP16 transactivation domain, a B42 acidic activator transactivation domain, and a retinoid X receptor ligand binding domain from an invertebrate species.

7. The viral vector according to claim 1, wherein:

a) said first hybrid polypeptide comprises:
  i) said DNA-binding domain; and
  ii) said ecdysone receptor ligand binding domain; and
b) said second hybrid polypeptide comprises:
  i) said transactivation domain; and
  ii) said retinoid X receptor ligand binding domain.

8. The viral vector according to claim 7, further comprising, a third gene expression cassette comprising:

i) a response element recognized by said DNA-binding domain;
ii) a promoter that is activated by said transactivation domain; and
iii) a gene whose expression is to be modulated.

9. The viral vector according to claim 7, wherein the retinoid X receptor ligand binding domain is encoded by a polynucleotide comprising a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

10. The viral vector according to claim 7, wherein the ecdysone receptor ligand binding domain is encoded by a polynucleotide comprising a nucleic acid sequence selected from the group consisting of SEQ ID NO: 1, SEQ ID NO: 53 and SEQ ID NO: 45.

11. The viral vector according to claim 7, wherein the DNA-binding domain is selected from the group consisting of a GAL4 DNA-binding domain, a LexA DNA-binding domain, and a retinoid X receptor ligand binding domain from an invertebrate species.

12. The viral vector according to claim 7, wherein the transactivation domain is selected from the group consisting of a VP16 transactivation domain, a B42 acidic activator transactivation domain, and an ecdysone receptor ligand binding domain.

13. An isolated host cell comprising the viral vector according to claim 1.

14. The isolated host cell according to claim 13, wherein the host cell is selected from the group consisting of a bacterial cell, a fungal cell, a yeast cell, an animal cell, and a mammalian cell.

15. The isolated host cell according to claim 14, wherein the mammalian cell is a murine cell or a human cell.

16. An isolated host cell comprising the viral vector according to claim 7.

17. The isolated host cell according to claim 16, wherein the host cell is selected from the group consisting of a bacterial cell, a fungal cell, a yeast cell, an animal cell, and a mammalian cell.

18. The isolated host cell according to claim 17, wherein the mammalian cell is a murine cell or a human cell.

19. The viral vector of claim 1, wherein said gene expression modulation system exhibits increased ligand sensitivity, relative to the ligand sensitivity of a gene expression modulation system that contains a retinoid X receptor ligand binding domain from a vertebrate species.

20. The viral vector of claim 19, wherein said gene expression modulation system exhibits increased sensitivity to non-steroidal ligands.

21. The viral vector of claim 20, wherein said gene expression modulation system exhibits increased sensitivity to non-steroidal ligands in mammalian cells.

22. The viral vector of claim 7, wherein said gene expression modulation system exhibits increased ligand sensitivity, relative to the ligand sensitivity of a gene expression modulation system that contains a retinoid X receptor ligand binding domain from a vertebrate species.

23. The viral vector of claim 22, wherein said system exhibits increased sensitivity to non-steroidal ligands.

24. The viral vector of claim 23, wherein said system exhibits increased sensitivity to non-steroidal ligands in mammalian cells.

25. The vital vector of claim 1, wherein said vector is an adenovirus vector.

26. The viral vector of claim 7, wherein said viral vector is an adenovirus vector.

27. The viral vector of claim 1, wherein said gene expression, modulation system is isolated.

* * * * *

SEQUENCE LISTING

```
<160> NUMBER OF SEQ ID NOS: 60

<210> SEQ ID NO 1
<211> LENGTH: 735
<212> TYPE: DNA
<213> ORGANISM: Choristoneura fumiferana

<400> SEQUENCE: 1

taccaggacg ggtacgagca gccttctgat gaagatttga agaggattac gcagacgtgg     60

cagcaagcgg acgatgaaaa cgaagagtct gacactccct tccgccagat cacagagatg    120

actatcctca cggtccaact tatcgtggag ttcgcgaagg gattgccagg gttcgccaag    180

atctcgcagc ctgatcaaat tacgctgctt aaggcttgct caagtgaggt aatgatgctc    240

cgagtcgcgc gacgatacga tgcggcctca gacagtgttc tgttcgcgaa caaccaagcg    300

tacactcgcg acaactaccg caaggctggc atggcctacg tcatcgagga tctactgcac    360

ttctgccggt gcatgtactc tatggcgttg gacaacatcc attacgcgct gctcacggct    420

gtcgtcatct tttctgaccg gccagggttg gagcagccgc aactggtgga agaaatccag    480
```

-continued cggtactacc tgaatacgct ccgcatctat atcctgaacc agctgagcgg gtcggcgcgt 540
tcgtccgtca tatacggcaa gatcctctca atcctctctg agctacgcac gctcggcatg 600
caaaactcca acatgtgcat ctccctcaag ctcaagaaca gaaagctgcc gcctttcctc 660
gaggagatct gggatgtggc ggacatgtcg cacacccaac cgccgcctat cctcgagtcc 720
cccacgaatc tctag 735

<210> SEQ ID NO 2
<211> LENGTH: 1338
<212> TYPE: DNA
<213> ORGANISM: Drosophila melanogaster

<400> SEQUENCE: 2
tatgagcagc catctgaaga ggatctcagg cgtataatga gtcaacccga tgagaacgag 60
agccaaacgg acgtcagctt tcggcatata accgagataa ccatactcac ggtccagttg 120
attgttgagt ttgctaaagg tctaccagcg tttacaaaga taccccagga ggaccagatc 180
acgttactaa aggcctgctc gtcggaggtg atgatgctgc gtatggcacg acgctatgac 240
cacagctcgg actcaatatt cttcgcgaat aatagatcat atacgcggga ttcttacaaa 300
atggccggaa tggctgataa cattgaagac ctgctgcatt tctgccgcca aatgttctcg 360
atgaaggtgg acaacgtcga atacgcgctt ctcactgcca ttgtgatctt ctcggaccgg 420
ccgggcctgg agaaggccca actagtcgaa gcgatccaga gctactacat cgacacgcta 480
cgcatttata tactcaaccg ccactgcggc gactcaatga gcctcgtctt ctacgcaaag 540
ctgctctcga tcctcaccga gctgcgtacg ctgggcaacc agaacgccga gatgtgtttc 600
tcactaaagc tcaaaaaccg caaactgccc aagttcctcg aggagatctg ggacgttcat 660
gccatcccgc catcggtcca gtcgcacctt cagattaccc aggaggagaa cgagcgtctc 720
gagcgggctg agcgtatgcg ggcatcggtt gggggcgcca ttaccgccgg cattgattgc 780
gactctgcct ccacttcggc ggcggcagcc gcggcccagc atcagcctca gcctcagccc 840
cagccccaac cctcctccct gacccagaac gattcccagc accagacaca gccgcagcta 900
caacctcagc taccacctca gctgcaaggt caactgcaac cccagctcca accacagctt 960
cagacgcaac tccagccaca gattcaacca cagccacagc tccttcccgt ctccgctccc 1020
gtgcccgcct ccgtaaccgc acctggttcc ttgtccgcgg tcagtacgag cagcgaatac 1080
atgggcggaa gtgcggccat aggacccatc acgccggcaa ccaccagcag tatcacggct 1140
gccgttaccg ctagctccac cacatcagcg gtaccgatgg gcaacggagt tggagtcggt 1200
gttggggtgg gcggcaacgt cagcatgtat gcgaacgccc agacggcgat ggccttgatg 1260
ggtgtagccc tgcattcgca ccaagagcag cttatcgggg gagtggcggt taagtcggag 1320
cactcgacga ctgcatag 1338

<210> SEQ ID NO 3
<211> LENGTH: 960
<212> TYPE: DNA
<213> ORGANISM: Choristoneura fumiferana

<400> SEQUENCE: 3
cctgagtgcg tagtacccga gactcagtgc gccatgaagc ggaaagagaa gaaagcacag 60
aaggagaagg acaaactgcc tgtcagcacg acgacggtgg acgaccacat gccgcccatt 120
atgcagtgtg aacctccacc tcctgaagca gcaaggattc acgaagtggt cccaaggttt 180
ctctccgaca agctgttgga gacaaaccgg cagaaaaaca tcccccagtt gacagccaac 240
cagcagttcc ttatcgccag gctcatctgg taccaggacg ggtacgagca gccttctgat 300
gaagatttga agaggattac gcagacgtgg cagcaagcgg acgatgaaaa cgaagagtct 360
gacactccct tccgccagat cacagagatg actatcctca cggtccaact tatcgtggag 420
ttcgcgaagg gattgccagg gttcgccaag atctcgcagc ctgatcaaat tacgctgctt 480
aaggcttgct caagtgaggt aatgatgctc cgagtcgcgc gacgatacga tgcggcctca 540
gacagtgttc tgttcgcgaa caaccaagcg tacactcgcg acaactaccg caaggctggc 600
atggcctacg tcatcgagga tctactgcac ttctgccggt gcatgtactc tatggcgttg 660
gacaacatcc attacgcgct gctcacggct gtcgtcatct ttctgaccg gccagggttg 720 gagcagccgc aactggtgga agaaatccag cggtactacc tgaatacgct ccgcatctat 780
atcctgaacc agctgagcgg gtcggcgcgt tcgtccgtca tatacggcaa gatcctctca 840
atcctctctg agctacgcac gctcggcatg caaaactcca acatgtgcat ctccctcaag 900
ctcaagaaca gaaagctgcc gcctttcctc gaggagatct gggatgtggc ggacatgtcg 960

<210> SEQ ID NO 4
<211> LENGTH: 969
<212> TYPE: DNA
<213> ORGANISM: Drosophila melanogaster

<400> SEQUENCE: 4
cggccggaat gcgtcgtccc ggagaaccaa tgtgcgatga agcggcgcga aaagaaggcc 60
cagaaggaga aggacaaaat gaccacttcg ccgagctctc agcatggcgg caatggcagc 120
ttggcctctg gtggcggcca agactttgtt aagaaggaga ttcttgacct tatgacatgc 180
gagccgcccc agcatgccac tattccgcta ctacctgatg aaatattggc caagtgtcaa 240
gcgcgcaata taccttcctt aacgtacaat cagttggccg ttatatacaa gttaatttgg 300
taccaggatg gctatgagca gccatctgaa gaggatctca ggcgtataat gagtcaaccc 360
gatgagaacg agagccaaac ggacgtcagc tttcggcata taaccgagat aaccatactc 420
acggtccagt tgattgttga gtttgctaaa ggtctaccag cgtttacaaa gataccccag 480
gaggaccaga tcacgttact aaaggcctgc tcgtcggagg tgatgatgct gcgtatggca 540
cgacgctatg accacagctc ggactcaata ttcttcgcga ataatagatc atatacgcgg 600
gattcttaca aaatggccgg aatggctgat aacattgaag acctgctgca tttctgccgc 660
caaatgttct cgatgaaggt ggacaacgtc gaatacgcgc ttctcactgc cattgtgatc 720
ttctcggacc ggccgggcct ggagaaggcc caactagtcg aagcgatcca gagctactac 780
atcgacacgc tacgcattta tatactcaac cgccactgcg gcgactcaat gagcctcgtc 840
ttctacgcaa agctgctctc gatcctcacc gagctgcgta cgctgggcaa ccagaacgcc 900
gagatgtgtt tctcactaaa gctcaaaaac cgcaaactgc ccaagttcct cgaggagatc 960
tgggacgtt 969

<210> SEQ ID NO 5
<211> LENGTH: 244
<212> TYPE: PRT
<213> ORGANISM: Choristoneura fumiferana

<400> SEQUENCE: 5

Tyr Gln Asp Gly Tyr Glu Gln Pro Ser Asp Glu Asp Leu Lys Arg Ile
1 5 10 15

Thr Gln Thr Trp Gln Gln Ala Asp Asp Glu Asn Glu Glu Ser Asp Thr

```
            20                  25                  30

Pro Phe Arg Gln Ile Thr Glu Met Thr Ile Leu Thr Val Gln Leu Ile
        35                  40                  45

Val Glu Phe Ala Lys Gly Leu Pro Gly Phe Ala Lys Ile Ser Gln Pro
    50                  55                  60

Asp Gln Ile Thr Leu Leu Lys Ala Cys Ser Ser Glu Val Met Met Leu
65                  70                  75                  80

Arg Val Ala Arg Arg Tyr Asp Ala Ala Ser Asp Ser Val Leu Phe Ala
                85                  90                  95

Asn Asn Gln Ala Tyr Thr Arg Asp Asn Tyr Arg Lys Ala Gly Met Ala
            100                 105                 110

Tyr Val Ile Glu Asp Leu Leu His Phe Cys Arg Cys Met Tyr Ser Met
        115                 120                 125

Ala Leu Asp Asn Ile His Tyr Ala Leu Leu Thr Ala Val Val Ile Phe
    130                 135                 140

Ser Asp Arg Pro Gly Leu Glu Gln Pro Gln Leu Val Glu Glu Ile Gln
145                 150                 155                 160

Arg Tyr Tyr Leu Asn Thr Leu Arg Ile Tyr Ile Leu Asn Gln Leu Ser
                165                 170                 175

Gly Ser Ala Arg Ser Ser Val Ile Tyr Gly Lys Ile Leu Ser Ile Leu
            180                 185                 190

Ser Glu Leu Arg Thr Leu Gly Met Gln Asn Ser Asn Met Cys Ile Ser
        195                 200                 205

Leu Lys Leu Lys Asn Arg Lys Leu Pro Pro Phe Leu Glu Glu Ile Trp
    210                 215                 220

Asp Val Ala Asp Met Ser His Thr Gln Pro Pro Pro Ile Leu Glu Ser
225                 230                 235                 240

Pro Thr Asn Leu


<210> SEQ ID NO 6
<211> LENGTH: 445
<212> TYPE: PRT
<213> ORGANISM: Drosophila melanogaster

<400> SEQUENCE: 6

Tyr Glu Gln Pro Ser Glu Glu Asp Leu Arg Arg Ile Met Ser Gln Pro
1               5                   10                  15

Asp Glu Asn Glu Ser Gln Thr Asp Val Ser Phe Arg His Ile Thr Glu
            20                  25                  30

Ile Thr Ile Leu Thr Val Gln Leu Ile Val Glu Phe Ala Lys Gly Leu
        35                  40                  45

Pro Ala Phe Thr Lys Ile Pro Gln Glu Asp Gln Ile Thr Leu Leu Lys
    50                  55                  60

Ala Cys Ser Ser Glu Val Met Met Leu Arg Met Ala Arg Arg Tyr Asp
65                  70                  75                  80

His Ser Ser Asp Ser Ile Phe Phe Ala Asn Asn Arg Ser Tyr Thr Arg
                85                  90                  95

Asp Ser Tyr Lys Met Ala Gly Met Ala Asp Asn Ile Glu Asp Leu Leu
            100                 105                 110

His Phe Cys Arg Gln Met Phe Ser Met Lys Val Asp Asn Val Glu Tyr
        115                 120                 125

Ala Leu Leu Thr Ala Ile Val Ile Phe Ser Asp Arg Pro Gly Leu Glu
    130                 135                 140

Lys Ala Gln Leu Val Glu Ala Ile Gln Ser Tyr Tyr Ile Asp Thr Leu
```

145 150 155 160

Arg Ile Tyr Ile Leu Asn Arg His Cys Gly Asp Ser Met Ser Leu Val
165 170 175

Phe Tyr Ala Lys Leu Leu Ser Ile Leu Thr Glu Leu Arg Thr Leu Gly
180 185 190

Asn Gln Asn Ala Glu Met Cys Phe Ser Leu Lys Leu Lys Asn Arg Lys
195 200 205

Leu Pro Lys Phe Leu Glu Glu Ile Trp Asp Val His Ala Ile Pro Pro
210 215 220

Ser Val Gln Ser His Leu Gln Ile Thr Gln Glu Glu Asn Glu Arg Leu
225 230 235 240

Glu Arg Ala Glu Arg Met Arg Ala Ser Val Gly Gly Ala Ile Thr Ala
245 250 255

Gly Ile Asp Cys Asp Ser Ala Ser Thr Ser Ala Ala Ala Ala Ala Ala
260 265 270

Gln His Gln Pro Gln Pro Gln Pro Gln Pro Gln Pro Ser Ser Leu Thr
275 280 285

Gln Asn Asp Ser Gln His Gln Thr Gln Pro Gln Leu Gln Pro Gln Leu
290 295 300

Pro Pro Gln Leu Gln Gly Gln Leu Gln Pro Gln Leu Gln Pro Gln Leu
305 310 315 320

Gln Thr Gln Leu Gln Pro Gln Ile Gln Pro Gln Pro Gln Leu Leu Pro
325 330 335

Val Ser Ala Pro Val Pro Ala Ser Val Thr Ala Pro Gly Ser Leu Ser
340 345 350

Ala Val Ser Thr Ser Ser Glu Tyr Met Gly Gly Ser Ala Ala Ile Gly
355 360 365

Pro Ile Thr Pro Ala Thr Thr Ser Ser Ile Thr Ala Ala Val Thr Ala
370 375 380

Ser Ser Thr Thr Ser Ala Val Pro Met Gly Asn Gly Val Gly Val Gly
385 390 395 400

Val Gly Val Gly Gly Asn Val Ser Met Tyr Ala Asn Ala Gln Thr Ala
405 410 415

Met Ala Leu Met Gly Val Ala Leu His Ser His Gln Glu Gln Leu Ile
420 425 430

Gly Gly Val Ala Val Lys Ser Glu His Ser Thr Thr Ala
435 440 445

<210> SEQ ID NO 7
<211> LENGTH: 320
<212> TYPE: PRT
<213> ORGANISM: Choristoneura fumiferana

<400> SEQUENCE: 7

Pro Glu Cys Val Val Pro Glu Thr Gln Cys Ala Met Lys Arg Lys Glu
1 5 10 15

Lys Lys Ala Gln Lys Glu Lys Asp Lys Leu Pro Val Ser Thr Thr Thr
20 25 30

Val Asp Asp His Met Pro Pro Ile Met Gln Cys Glu Pro Pro Pro Pro
35 40 45

Glu Ala Ala Arg Ile His Glu Val Val Pro Arg Phe Leu Ser Asp Lys
50 55 60

Leu Leu Glu Thr Asn Arg Gln Lys Asn Ile Pro Gln Leu Thr Ala Asn
65 70 75 80

-continued

```
Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
    290                 295                 300

Lys Leu Pro Pro Phe Leu Glu Glu Ile Trp Asp Val Ala Asp Met Ser
305                 310                 315                 320


<210> SEQ ID NO 8
<211> LENGTH: 323
<212> TYPE: PRT
<213> ORGANISM: Drosophila melanogaster

<400> SEQUENCE: 8

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95

Lys Leu Ile Trp Tyr Gln Asp Gly Tyr Glu Gln Pro Ser Glu Glu Asp
            100                 105                 110

Leu Arg Arg Ile Met Ser Gln Pro Asp Glu Asn Glu Ser Gln Thr Asp
        115                 120                 125

Val Ser Phe Arg His Ile Thr Glu Ile Thr Ile Leu Thr Val Gln Leu
    130                 135                 140
```

```
Ile Val Glu Phe Ala Lys Gly Leu Pro Ala Phe Thr Lys Ile Pro Gln
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
        195                 200                 205

Ala Asp Asn Ile Glu Asp Leu Leu His Phe Cys Arg Gln Met Phe Ser
    210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270

Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val
```

<210> SEQ ID NO 9
<211> LENGTH: 635
<212> TYPE: DNA
<213> ORGANISM: Locusta migratoria

<400> SEQUENCE: 9

```
tgcatacaga catgcctgtt gaacgcatac ttgaagctga aaaacgagtg gagtgcaaag     60

cagaaaacca agtggaatat gagctggtgg agtgggctaa acacatcccg cacttcacat    120

ccctacctct ggaggaccag gttctcctcc tcagagcagg ttggaatgaa ctgctaattg    180

cagcattttc acatcgatct gtagatgtta aagatggcat agtacttgcc actggtctca    240

cagtgcatcg aaattctgcc catcaagctg gagtcggcac aatatttgac agagttttga    300

cagaactggt agcaaagatg agagaaatga aaatggataa aactgaactt ggctgcttgc    360

gatctgttat tcttttcaat ccagaggtga ggggtttgaa atccgcccag gaagttgaac    420

ttctacgtga aaaagtatat gccgctttgg aagaatatac tagaacaaca catcccgatg    480

aaccaggaag atttgcaaaa cttttgcttc gtctgccttc tttacgttcc ataggcctta    540

agtgtttgga gcatttgttt ttctttcgcc ttattggaga tgttccaatt gatacgttcc    600

tgatggagat gcttgaatca ccttctgatt cataa                              635
```

<210> SEQ ID NO 10
<211> LENGTH: 687
<212> TYPE: DNA
<213> ORGANISM: Amblyomma americanum

<400> SEQUENCE: 10

```
cctcctgaga tgcctctgga gcgcatactg gaggcagagc tgcgggttga gtcacagacg     60

gggaccctct cggaaagcgc acagcagcag gatccagtga gcagcatctg ccaagctgca    120

gaccgacagc tgcaccagct agttcaatgg gccaagcaca ttccacattt tgaagagctt    180
```

-continued

```
ccccttgagg accgcatggt gttgctcaag gctggctgga acgagctgct cattgctgct    240

ttctcccacc gttctgttga cgtgcgtgat ggcattgtgc tcgctacagg tcttgtggtg    300

cagcggcata gtgctcatgg ggctggcgtt ggggccatat ttgatagggt tctcactgaa    360

ctggtagcaa agatgcgtga gatgaagatg gaccgcactg agcttggatg cctgcttgct    420

gtggtacttt ttaatcctga ggccaagggg ctgcggacct gcccaagtgg aggccctgag    480

ggagaaagtg tatctgcctt ggaagagcac tgccggcagc agtacccaga ccagcctggg    540

cgctttgcca agctgctgct gcggttgcca gctctgcgca gtattggcct caagtgcctc    600

gaacatctct ttttcttcaa gctcatcggg gacacgccca tcgacaactt tcttctttcc    660

atgctggagg ccccctctga cccctaa                                        687
```

<210> SEQ ID NO 11
<211> LENGTH: 693
<212> TYPE: DNA
<213> ORGANISM: Amblyomma americanum

<400> SEQUENCE: 11

```
tctccggaca tgccactcga acgcattctc gaagccgaga tgcgcgtcga gcagccggca     60

ccgtccgttt tggcgcagac ggccgcatcg ggccgcgacc ccgtcaacag catgtgccag    120

gctgccccgc cacttcacga gctcgtacag tgggcccggc gaattccgca cttcgaagag    180

cttcccatcg aggatcgcac cgcgctgctc aaagccggct ggaacgaact gcttattgcc    240

gccttttcgc accgttctgt ggcggtgcgc gacggcatcg ttctggccac cgggctggtg    300

gtgcagcggc acagcgcaca cggcgcaggc gttggcgaca tcttcgaccg cgtactagcc    360

gagctggtgg ccaagatgcg cgacatgaag atggacaaaa cggagctcgg ctgcctgcgc    420

gccgtggtgc tcttcaatcc agacgccaag ggtctccgaa acgccaccag agtagaggcg    480

ctccgcgaga aggtgtatgc ggcgctggag gagcactgcc gtcggcacca cccggaccaa    540

ccgggtcgct tcggcaagct gctgctgcgg ctgcctgcct tgcgcagcat cgggctcaaa    600

tgcctcgagc atctgttctt cttcaagctc atcggagaca ctcccataga cagcttcctg    660

ctcaacatgc tggaggcacc ggcagacccc tag                                 693
```

<210> SEQ ID NO 12
<211> LENGTH: 801
<212> TYPE: DNA
<213> ORGANISM: Celuca pugilator

<400> SEQUENCE: 12

```
tcagacatgc caattgccag catacgggag gcagagctca gcgtggatcc catagatgag     60

cagccgctgg accaaggggt gaggcttcag gttccactcg cacctcctga tagtgaaaag    120

tgtagcttta ctttaccttt tcatcccgtc agtgaagtat cctgtgctaa ccctctgcag    180

gatgtggtga gcaacatatg ccaggcagct gacagacatc tggtgcagct ggtggagtgg    240

gccaagcaca tcccacactt cacagacctt cccatagagg accaagtggt attactcaaa    300

gccgggtgga acgagttgct tattgcctca ttctcacacc gtagcatggg cgtggaggat    360

ggcatcgtgc tggccacagg gctcgtgatc cacagaagta gtgctcacca ggctggagtg    420

ggtgccatat ttgatcgtgt cctctctgag ctggtggcca agatgaagga gatgaagatt    480

gacaagacag agctgggctg ccttcgctcc atcgtcctgt tcaacccaga tgccaaagga    540

ctaaactgcg tcaatgatgt ggagatcttg cgtgagaagg tgtatgctgc cctggaggag    600
```

-continued tacacacgaa ccacttaccc tgatgaacct ggacgctttg ccaagttgct tctgcgactt 660
cctgcactca ggtctatagg cctgaagtgt cttgagtacc tcttcctgtt taagctgatt 720
ggagacactc ccctggacag ctacttgatg aagatgctcg tagacaaccc aaatacaagc 780
gtcactcccc ccaccagcta g 801

<210> SEQ ID NO 13
<211> LENGTH: 690
<212> TYPE: DNA
<213> ORGANISM: Tenebrio molitor

<400> SEQUENCE: 13
gccgagatgc ccctcgacag gataatcgag gcggagaaac ggatagaatg cacacccgct 60
ggtggctctg gtggtgtcgg agagcaacac gacggggtga acaacatctg tcaagccact 120
aacaagcagc tgttccaact ggtgcaatgg gctaagctca tacctcactt tacctcgttg 180
ccgatgtcgg accaggtgct tttattgagg gcaggatgga atgaattgct catcgccgca 240
ttctcgcaca gatctataca ggcgcaggat gccatcgttc tagccacggg gttgacagtt 300
aacaaaacgt cggcgcacgc cgtgggcgtg ggcaacatct acgaccgcgt cctctccgag 360
ctggtgaaca agatgaaaga gatgaagatg gacaagacgg agctgggctg cttgagagcc 420
atcatcctct acaaccccac gtgtcgcggc atcaagtccg tgcaggaagt ggagatgctg 480
cgtgagaaaa tttacggcgt gctggaagag tacaccagga ccacccaccc gaacgagccc 540
ggcaggttcg ccaaactgct tctgcgcctc ccggccctca ggtccatcgg gttgaaatgt 600
tccgaacacc tctttttctt caagctgatc ggtgatgttc caatagacac gttcctgatg 660
gagatgctgg agtctccggc ggacgcttag 690

<210> SEQ ID NO 14
<211> LENGTH: 681
<212> TYPE: DNA
<213> ORGANISM: Apis mellifera

<400> SEQUENCE: 14
cattcggaca tgccgatcga gcgtatcctg gaggccgaga agagagtcga atgtaagatg 60
gagcaacagg gaaattacga gaatgcagtg tcgcacattt gcaacgccac gaacaaacag 120
ctgttccagc tggtagcatg ggcgaaacac atcccgcatt ttacctcgtt gccactggag 180
gatcaggtac ttctgctcag ggccggttgg aacgagttgc tgatagcctc cttttcccac 240
cgttccatcg acgtgaagga cggtatcgtg ctggcgacgg ggatcaccgt gcatcggaac 300
tcggcgcagc aggccggcgt gggcacgata ttcgaccgtg tcctctcgga gcttgtctcg 360
aaaatgcgtg aaatgaagat ggacaggaca gagcttggct gtctcagatc tataatactc 420
ttcaatcccg aggttcgagg actgaaatcc atccaggaag tgaccctgct ccgtgagaag 480
atctacggcg ccctggaggg ttattgccgc gtagcttggc ccgacgacgc tggaagattc 540
gcgaaattac ttctacgcct gcccgccatc cgctcgatcg gattaaagtg cctcgagtac 600
ctgttcttct tcaaaatgat cggtgacgta ccgatcgacg attttctcgt ggagatgtta 660
gaatcgcgat cagatcctta g 681

<210> SEQ ID NO 15
<211> LENGTH: 516
<212> TYPE: DNA
<213> ORGANISM: Locusta migratoria

<400> SEQUENCE: 15

```
atccctacct ctggaggacc aggttctcct cctcagagca ggttggaatg aactgctaat     60

tgcagcattt tcacatcgat ctgtagatgt taaagatggc atagtacttg ccactggtct    120

cacagtgcat cgaaattctg cccatcaagc tggagtcggc acaatatttg acagagtttt    180

gacagaactg gtagcaaaga tgagagaaat gaaaatggat aaaactgaac ttggctgctt    240

gcgatctgtt attcttttca atccagaggt gaggggtttg aaatccgccc aggaagttga    300

acttctacgt gaaaaagtat atgccgcttt ggaagaatat actagaacaa cacatcccga    360

tgaaccagga agatttgcaa aacttttgct tcgtctgcct tctttacgtt ccataggcct    420

taagtgtttg gagcatttgt tttctttcgc cttattggag atgttccaat tgatacgttc    480

ctgatggaga tgcttgaatc accttctgat tcataa                              516


<210> SEQ ID NO 16
<211> LENGTH: 528
<212> TYPE: DNA
<213> ORGANISM: Amblyomma americanum

<400> SEQUENCE: 16

attccacatt ttgaagagct tccccttgag gaccgcatgg tgttgctcaa ggctggctgg     60

aacgagctgc tcattgctgc tttctcccac cgttctgttg acgtgcgtga tggcattgtg    120

ctcgctacag gtcttgtggt gcagcggcat agtgctcatg ggctggcgt tggggccata    180

tttgataggg ttctcactga actggtagca aagatgcgtg agatgaagat ggaccgcact    240

gagcttggat gcctgcttgc tgtggtactt tttaatcctg aggccaaggg gctgcggacc    300

tgcccaagtg gaggccctga gggagaaagt gtatctgcct tggaagagca ctgccggcag    360

cagtacccag accagcctgg gcgctttgcc aagctgctgc tgcggttgcc agctctgcgc    420

agtattggcc tcaagtgcct cgaacatctc tttttcttca agctcatcgg ggacacgccc    480

atcgacaact ttcttctttc catgctggag gccccctctg acccctaa                 528


<210> SEQ ID NO 17
<211> LENGTH: 531
<212> TYPE: DNA
<213> ORGANISM: Amblyomma americanum

<400> SEQUENCE: 17

attccgcact tcgaagagct tcccatcgag gatcgcaccg cgctgctcaa agccggctgg     60

aacgaactgc ttattgccgc cttttcgcac cgttctgtgg cggtgcgcga cggcatcgtt    120

ctggccaccg ggctggtggt gcagcggcac agcgcacacg gcgcaggcgt tggcgacatc    180

ttcgaccgcg tactagccga gctggtggcc aagatgcgcg acatgaagat ggacaaaacg    240

gagctcggct gcctgcgcgc cgtggtgctc ttcaatccag acgccaaggg tctccgaaac    300

gccaccagag tagaggcgct ccgcgagaag gtgtatgcgg cgctggagga gcactgccgt    360

cggcaccacc cggaccaacc gggtcgcttc ggcaagctgc tgctgcggct gcctgccttg    420

cgcagcatcg ggctcaaatg cctcgagcat ctgttcttct tcaagctcat cggagacact    480

cccatagaca gcttcctgct caacatgctg gaggcaccgg cagaccccta g             531


<210> SEQ ID NO 18
<211> LENGTH: 552
<212> TYPE: DNA
<213> ORGANISM: Celuca pugilator

<400> SEQUENCE: 18
```

-continued

```
atcccacact tcacagacct tcccatagag gaccaagtgg tattactcaa agccgggtgg      60

aacgagttgc ttattgcctc attctcacac cgtagcatgg gcgtggagga tggcatcgtg     120

ctggccacag ggctcgtgat ccacagaagt agtgctcacc aggctggagt gggtgccata     180

tttgatcgtg tcctctctga gctggtggcc aagatgaagg agatgaagat tgacaagaca     240

gagctgggct gccttcgctc catcgtcctg ttcaacccag atgccaaagg actaaactgc     300

gtcaatgatg tggagatctt gcgtgagaag gtgtatgctg ccctggagga gtacacacga     360

accacttacc ctgatgaacc tggacgcttt gccaagttgc ttctgcgact tcctgcactc     420

aggtctatag gcctgaagtg tcttgagtac ctcttcctgt ttaagctgat tggagacact     480

cccctggaca gctacttgat gaagatgctc gtagacaacc caaatacaag cgtcactccc     540

cccaccagct ag                                                         552
```

<210> SEQ ID NO 19
<211> LENGTH: 531
<212> TYPE: DNA
<213> ORGANISM: Tenebrio molitor

<400> SEQUENCE: 19

```
atacctcact ttacctcgtt gccgatgtcg gaccaggtgc ttttattgag ggcaggatgg      60

aatgaattgc tcatcgccgc attctcgcac agatctatac aggcgcagga tgccatcgtt     120

ctagccacgg ggttgacagt taacaaaacg tcggcgcacg ccgtgggcgt gggcaacatc     180

tacgaccgcg tcctctccga gctggtgaac aagatgaaag agatgaagat ggacaagacg     240

gagctgggct gcttgagagc catcatcctc tacaacccca cgtgtcgcgg catcaagtcc     300

gtgcaggaag tggagatgct gcgtgagaaa atttacggcg tgctggaaga gtacaccagg     360

accacccacc cgaacgagcc cggcaggttc gccaaactgc ttctgcgcct cccggccctc     420

aggtccatcg ggttgaaatg ttccgaacac ctctttttct tcaagctgat cggtgatgtt     480

ccaatagaca cgttcctgat ggagatgctg gagtctccgg cggacgctta g              531
```

<210> SEQ ID NO 20
<211> LENGTH: 531
<212> TYPE: DNA
<213> ORGANISM: Apis mellifera

<400> SEQUENCE: 20

```
atcccgcatt ttacctcgtt gccactggag gatcaggtac ttctgctcag ggccggttgg      60

aacgagttgc tgatagcctc cttttcccac cgttccatcg acgtgaagga cggtatcgtg     120

ctggcgacgg ggatcaccgt gcatcggaac tcggcgcagc aggccggcgt gggcacgata     180

ttcgaccgtg tcctctcgga gcttgtctcg aaaatgcgtg aaatgaagat ggacaggaca     240

gagcttggct gtctcagatc tataatactc ttcaatcccg aggttcgagg actgaaatcc     300

atccaggaag tgaccctgct ccgtgagaag atctacggcg ccctggaggg ttattgccgc     360

gtagcttggc ccgacgacgc tggaagattc gcgaaattac ttctacgcct gcccgccatc     420

cgctcgatcg gattaaagtg cctcgagtac ctgttcttct tcaaaatgat cggtgacgta     480

ccgatcgacg attttctcgt ggagatgtta gaatcgcgat cagatcctta g              531
```

<210> SEQ ID NO 21
<211> LENGTH: 210
<212> TYPE: PRT
<213> ORGANISM: Locusta migratoria

<400> SEQUENCE: 21

```
His Thr Asp Met Pro Val Glu Arg Ile Leu Glu Ala Glu Lys Arg Val
1               5                   10                  15

Glu Cys Lys Ala Glu Asn Gln Val Glu Tyr Glu Leu Val Glu Trp Ala
            20                  25                  30

Lys His Ile Pro His Phe Thr Ser Leu Pro Leu Glu Asp Gln Val Leu
        35                  40                  45

Leu Leu Arg Ala Gly Trp Asn Glu Leu Leu Ile Ala Ala Phe Ser His
    50                  55                  60

Arg Ser Val Asp Val Lys Asp Gly Ile Val Leu Ala Thr Gly Leu Thr
65                  70                  75                  80

Val His Arg Asn Ser Ala His Gln Ala Gly Val Gly Thr Ile Phe Asp
                85                  90                  95

Arg Val Leu Thr Glu Leu Val Ala Lys Met Arg Glu Met Lys Met Asp
            100                 105                 110

Lys Thr Glu Leu Gly Cys Leu Arg Ser Val Ile Leu Phe Asn Pro Glu
        115                 120                 125

Val Arg Gly Leu Lys Ser Ala Gln Glu Val Glu Leu Leu Arg Glu Lys
    130                 135                 140

Val Tyr Ala Ala Leu Glu Glu Tyr Thr Arg Thr Thr His Pro Asp Glu
145                 150                 155                 160

Pro Gly Arg Phe Ala Lys Leu Leu Leu Arg Leu Pro Ser Leu Arg Ser
                165                 170                 175

Ile Gly Leu Lys Cys Leu Glu His Leu Phe Phe Phe Arg Leu Ile Gly
            180                 185                 190

Asp Val Pro Ile Asp Thr Phe Leu Met Glu Met Leu Glu Ser Pro Ser
        195                 200                 205

Asp Ser
    210


<210> SEQ ID NO 22
<211> LENGTH: 228
<212> TYPE: PRT
<213> ORGANISM: Amblyomma americanum

<400> SEQUENCE: 22

Pro Pro Glu Met Pro Leu Glu Arg Ile Leu Glu Ala Glu Leu Arg Val
1               5                   10                  15

Glu Ser Gln Thr Gly Thr Leu Ser Glu Ser Ala Gln Gln Gln Asp Pro
            20                  25                  30

Val Ser Ser Ile Cys Gln Ala Ala Asp Arg Gln Leu His Gln Leu Val
        35                  40                  45

Gln Trp Ala Lys His Ile Pro His Phe Glu Glu Leu Pro Leu Glu Asp
    50                  55                  60

Arg Met Val Leu Leu Lys Ala Gly Trp Asn Glu Leu Leu Ile Ala Ala
65                  70                  75                  80

Phe Ser His Arg Ser Val Asp Val Arg Asp Gly Ile Val Leu Ala Thr
                85                  90                  95

Gly Leu Val Val Gln Arg His Ser Ala His Gly Ala Gly Val Gly Ala
            100                 105                 110

Ile Phe Asp Arg Val Leu Thr Glu Leu Val Ala Lys Met Arg Glu Met
        115                 120                 125

Lys Met Asp Arg Thr Glu Leu Gly Cys Leu Leu Ala Val Val Leu Phe
    130                 135                 140

Asn Pro Glu Ala Lys Gly Leu Arg Thr Cys Pro Ser Gly Gly Pro Glu
```

```
145                 150                 155                 160

Gly Glu Ser Val Ser Ala Leu Glu Glu His Cys Arg Gln Gln Tyr Pro
                165                 170                 175

Asp Gln Pro Gly Arg Phe Ala Lys Leu Leu Leu Arg Leu Pro Ala Leu
            180                 185                 190

Arg Ser Ile Gly Leu Lys Cys Leu Glu His Leu Phe Phe Phe Lys Leu
        195                 200                 205

Ile Gly Asp Thr Pro Ile Asp Asn Phe Leu Leu Ser Met Leu Glu Ala
    210                 215                 220

Pro Ser Asp Pro
225


<210> SEQ ID NO 23
<211> LENGTH: 230
<212> TYPE: PRT
<213> ORGANISM: Amblyomma americanum

<400> SEQUENCE: 23

Ser Pro Asp Met Pro Leu Glu Arg Ile Leu Glu Ala Glu Met Arg Val
1               5                   10                  15

Glu Gln Pro Ala Pro Ser Val Leu Ala Gln Thr Ala Ala Ser Gly Arg
            20                  25                  30

Asp Pro Val Asn Ser Met Cys Gln Ala Ala Pro Pro Leu His Glu Leu
        35                  40                  45

Val Gln Trp Ala Arg Arg Ile Pro His Phe Glu Glu Leu Pro Ile Glu
    50                  55                  60

Asp Arg Thr Ala Leu Leu Lys Ala Gly Trp Asn Glu Leu Leu Ile Ala
65                  70                  75                  80

Ala Phe Ser His Arg Ser Val Ala Val Arg Asp Gly Ile Val Leu Ala
                85                  90                  95

Thr Gly Leu Val Val Gln Arg His Ser Ala His Gly Ala Gly Val Gly
            100                 105                 110

Asp Ile Phe Asp Arg Val Leu Ala Glu Leu Val Ala Lys Met Arg Asp
        115                 120                 125

Met Lys Met Asp Lys Thr Glu Leu Gly Cys Leu Arg Ala Val Val Leu
    130                 135                 140

Phe Asn Pro Asp Ala Lys Gly Leu Arg Asn Ala Thr Arg Val Glu Ala
145                 150                 155                 160

Leu Arg Glu Lys Val Tyr Ala Ala Leu Glu Glu His Cys Arg Arg His
                165                 170                 175

His Pro Asp Gln Pro Gly Arg Phe Gly Lys Leu Leu Leu Arg Leu Pro
            180                 185                 190

Ala Leu Arg Ser Ile Gly Leu Lys Cys Leu Glu His Leu Phe Phe Phe
        195                 200                 205

Lys Leu Ile Gly Asp Thr Pro Ile Asp Ser Phe Leu Leu Asn Met Leu
    210                 215                 220

Glu Ala Pro Ala Asp Pro
225                 230


<210> SEQ ID NO 24
<211> LENGTH: 266
<212> TYPE: PRT
<213> ORGANISM: Celuca pugilator

<400> SEQUENCE: 24

Ser Asp Met Pro Ile Ala Ser Ile Arg Glu Ala Glu Leu Ser Val Asp
```

```
1               5                   10                  15

Pro Ile Asp Glu Gln Pro Leu Asp Gln Gly Val Arg Leu Gln Val Pro
            20                  25                  30

Leu Ala Pro Pro Asp Ser Glu Lys Cys Ser Phe Thr Leu Pro Phe His
        35                  40                  45

Pro Val Ser Glu Val Ser Cys Ala Asn Pro Leu Gln Asp Val Val Ser
    50                  55                  60

Asn Ile Cys Gln Ala Ala Asp Arg His Leu Val Gln Leu Val Glu Trp
65                  70                  75                  80

Ala Lys His Ile Pro His Phe Thr Asp Leu Pro Ile Glu Asp Gln Val
                85                  90                  95

Val Leu Leu Lys Ala Gly Trp Asn Glu Leu Leu Ile Ala Ser Phe Ser
            100                 105                 110

His Arg Ser Met Gly Val Glu Asp Gly Ile Val Leu Ala Thr Gly Leu
        115                 120                 125

Val Ile His Arg Ser Ser Ala His Gln Ala Gly Val Gly Ala Ile Phe
    130                 135                 140

Asp Arg Val Leu Ser Glu Leu Val Ala Lys Met Lys Glu Met Lys Ile
145                 150                 155                 160

Asp Lys Thr Glu Leu Gly Cys Leu Arg Ser Ile Val Leu Phe Asn Pro
                165                 170                 175

Asp Ala Lys Gly Leu Asn Cys Val Asn Asp Val Glu Ile Leu Arg Glu
            180                 185                 190

Lys Val Tyr Ala Ala Leu Glu Glu Tyr Thr Arg Thr Thr Tyr Pro Asp
        195                 200                 205

Glu Pro Gly Arg Phe Ala Lys Leu Leu Leu Arg Leu Pro Ala Leu Arg
    210                 215                 220

Ser Ile Gly Leu Lys Cys Leu Glu Tyr Leu Phe Leu Phe Lys Leu Ile
225                 230                 235                 240

Gly Asp Thr Pro Leu Asp Ser Tyr Leu Met Lys Met Leu Val Asp Asn
                245                 250                 255

Pro Asn Thr Ser Val Thr Pro Pro Thr Ser
            260                 265
```

<210> SEQ ID NO 25
<211> LENGTH: 229
<212> TYPE: PRT
<213> ORGANISM: Tenebrio molitor

<400> SEQUENCE: 25

```
Ala Glu Met Pro Leu Asp Arg Ile Ile Glu Ala Glu Lys Arg Ile Glu
1               5                   10                  15

Cys Thr Pro Ala Gly Gly Ser Gly Gly Val Gly Glu Gln His Asp Gly
            20                  25                  30

Val Asn Asn Ile Cys Gln Ala Thr Asn Lys Gln Leu Phe Gln Leu Val
        35                  40                  45

Gln Trp Ala Lys Leu Ile Pro His Phe Thr Ser Leu Pro Met Ser Asp
    50                  55                  60

Gln Val Leu Leu Leu Arg Ala Gly Trp Asn Glu Leu Leu Ile Ala Ala
65                  70                  75                  80

Phe Ser His Arg Ser Ile Gln Ala Gln Asp Ala Ile Val Leu Ala Thr
                85                  90                  95

Gly Leu Thr Val Asn Lys Thr Ser Ala His Ala Val Gly Val Gly Asn
            100                 105                 110
```

```
Ile Tyr Asp Arg Val Leu Ser Glu Leu Val Asn Lys Met Lys Glu Met
        115                 120                 125

Lys Met Asp Lys Thr Glu Leu Gly Cys Leu Arg Ala Ile Ile Leu Tyr
    130                 135                 140

Asn Pro Thr Cys Arg Gly Ile Lys Ser Val Gln Glu Val Glu Met Leu
145                 150                 155                 160

Arg Glu Lys Ile Tyr Gly Val Leu Glu Glu Tyr Thr Arg Thr Thr His
                165                 170                 175

Pro Asn Glu Pro Gly Arg Phe Ala Lys Leu Leu Leu Arg Leu Pro Ala
            180                 185                 190

Leu Arg Ser Ile Gly Leu Lys Cys Ser Glu His Leu Phe Phe Phe Lys
        195                 200                 205

Leu Ile Gly Asp Val Pro Ile Asp Thr Phe Leu Met Glu Met Leu Glu
    210                 215                 220

Ser Pro Ala Asp Ala
225


<210> SEQ ID NO 26
<211> LENGTH: 226
<212> TYPE: PRT
<213> ORGANISM: Apis mellifera

<400> SEQUENCE: 26

His Ser Asp Met Pro Ile Glu Arg Ile Leu Glu Ala Glu Lys Arg Val
1               5                   10                  15

Glu Cys Lys Met Glu Gln Gln Gly Asn Tyr Glu Asn Ala Val Ser His
            20                  25                  30

Ile Cys Asn Ala Thr Asn Lys Gln Leu Phe Gln Leu Val Ala Trp Ala
        35                  40                  45

Lys His Ile Pro His Phe Thr Ser Leu Pro Leu Glu Asp Gln Val Leu
    50                  55                  60

Leu Leu Arg Ala Gly Trp Asn Glu Leu Leu Ile Ala Ser Phe Ser His
65                  70                  75                  80

Arg Ser Ile Asp Val Lys Asp Gly Ile Val Leu Ala Thr Gly Ile Thr
                85                  90                  95

Val His Arg Asn Ser Ala Gln Gln Ala Gly Val Gly Thr Ile Phe Asp
            100                 105                 110

Arg Val Leu Ser Glu Leu Val Ser Lys Met Arg Glu Met Lys Met Asp
        115                 120                 125

Arg Thr Glu Leu Gly Cys Leu Arg Ser Ile Ile Leu Phe Asn Pro Glu
    130                 135                 140

Val Arg Gly Leu Lys Ser Ile Gln Glu Val Thr Leu Leu Arg Glu Lys
145                 150                 155                 160

Ile Tyr Gly Ala Leu Glu Gly Tyr Cys Arg Val Ala Trp Pro Asp Asp
                165                 170                 175

Ala Gly Arg Phe Ala Lys Leu Leu Leu Arg Leu Pro Ala Ile Arg Ser
            180                 185                 190

Ile Gly Leu Lys Cys Leu Glu Tyr Leu Phe Phe Phe Lys Met Ile Gly
        195                 200                 205

Asp Val Pro Ile Asp Asp Phe Leu Val Glu Met Leu Glu Ser Arg Ser
    210                 215                 220

Asp Pro
225


<210> SEQ ID NO 27
```

<211> LENGTH: 176
<212> TYPE: PRT
<213> ORGANISM: Locusta migratoria

<400> SEQUENCE: 27

```
Ile Pro His Phe Thr Ser Leu Pro Leu Glu Asp Gln Val Leu Leu Leu
1               5                   10                  15

Arg Ala Gly Trp Asn Glu Leu Leu Ile Ala Ala Phe Ser His Arg Ser
            20                  25                  30

Val Asp Val Lys Asp Gly Ile Val Leu Ala Thr Gly Leu Thr Val His
        35                  40                  45

Arg Asn Ser Ala His Gln Ala Gly Val Gly Thr Ile Phe Asp Arg Val
    50                  55                  60

Leu Thr Glu Leu Val Ala Lys Met Arg Glu Met Lys Met Asp Lys Thr
65                  70                  75                  80

Glu Leu Gly Cys Leu Arg Ser Val Ile Leu Phe Asn Pro Glu Val Arg
                85                  90                  95

Gly Leu Lys Ser Ala Gln Glu Val Glu Leu Leu Arg Glu Lys Val Tyr
            100                 105                 110

Ala Ala Leu Glu Glu Tyr Thr Arg Thr Thr His Pro Asp Glu Pro Gly
        115                 120                 125

Arg Phe Ala Lys Leu Leu Leu Arg Leu Pro Ser Leu Arg Ser Ile Gly
    130                 135                 140

Leu Lys Cys Leu Glu His Leu Phe Phe Phe Arg Leu Ile Gly Asp Val
145                 150                 155                 160

Pro Ile Asp Thr Phe Leu Met Glu Met Leu Glu Ser Pro Ser Asp Ser
                165                 170                 175
```

<210> SEQ ID NO 28
<211> LENGTH: 175
<212> TYPE: PRT
<213> ORGANISM: Amblyomma americanum

<400> SEQUENCE: 28

```
Ile Pro His Phe Glu Glu Leu Pro Leu Glu Asp Arg Met Val Leu Leu
1               5                   10                  15

Lys Ala Gly Trp Asn Glu Leu Leu Ile Ala Ala Phe Ser His Arg Ser
            20                  25                  30

Val Asp Val Arg Asp Gly Ile Val Leu Ala Thr Gly Leu Val Val Gln
        35                  40                  45

Arg His Ser Ala His Gly Ala Gly Val Gly Ala Ile Phe Asp Arg Val
    50                  55                  60

Leu Thr Glu Leu Val Ala Lys Met Arg Glu Met Lys Met Asp Arg Thr
65                  70                  75                  80

Glu Leu Gly Cys Leu Leu Ala Val Val Leu Phe Asn Pro Glu Ala Lys
                85                  90                  95

Gly Leu Arg Thr Cys Pro Ser Gly Gly Pro Glu Gly Glu Ser Val Ser
            100                 105                 110

Ala Leu Glu Glu His Cys Arg Gln Gln Tyr Pro Asp Gln Pro Gly Arg
        115                 120                 125

Phe Ala Lys Leu Leu Leu Arg Leu Pro Ala Leu Arg Ser Ile Gly Leu
    130                 135                 140

Lys Cys Leu Glu His Leu Phe Phe Phe Lys Leu Ile Gly Asp Thr Pro
145                 150                 155                 160

Ile Asp Asn Phe Leu Leu Ser Met Leu Glu Ala Pro Ser Asp Pro
                165                 170                 175
```

<210> SEQ ID NO 29
<211> LENGTH: 176
<212> TYPE: PRT
<213> ORGANISM: Amblyomma americanum

<400> SEQUENCE: 29

Ile Pro His Phe Glu Glu Leu Pro Ile Glu Asp Arg Thr Ala Leu Leu
1 5 10 15

Lys Ala Gly Trp Asn Glu Leu Leu Ile Ala Ala Phe Ser His Arg Ser
20 25 30

Val Ala Val Arg Asp Gly Ile Val Leu Ala Thr Gly Leu Val Val Gln
35 40 45

Arg His Ser Ala His Gly Ala Gly Val Gly Asp Ile Phe Asp Arg Val
50 55 60

Leu Ala Glu Leu Val Ala Lys Met Arg Asp Met Lys Met Asp Lys Thr
65 70 75 80

Glu Leu Gly Cys Leu Arg Ala Val Val Leu Phe Asn Pro Asp Ala Lys
85 90 95

Gly Leu Arg Asn Ala Thr Arg Val Glu Ala Leu Arg Glu Lys Val Tyr
100 105 110

Ala Ala Leu Glu Glu His Cys Arg Arg His His Pro Asp Gln Pro Gly
115 120 125

Arg Phe Gly Lys Leu Leu Leu Arg Leu Pro Ala Leu Arg Ser Ile Gly
130 135 140

Leu Lys Cys Leu Glu His Leu Phe Phe Phe Lys Leu Ile Gly Asp Thr
145 150 155 160

Pro Ile Asp Ser Phe Leu Leu Asn Met Leu Glu Ala Pro Ala Asp Pro
165 170 175

<210> SEQ ID NO 30
<211> LENGTH: 183
<212> TYPE: PRT
<213> ORGANISM: Celuca pugilator

<400> SEQUENCE: 30

Ile Pro His Phe Thr Asp Leu Pro Ile Glu Asp Gln Val Val Leu Leu
1 5 10 15

Lys Ala Gly Trp Asn Glu Leu Leu Ile Ala Ser Phe Ser His Arg Ser
20 25 30

Met Gly Val Glu Asp Gly Ile Val Leu Ala Thr Gly Leu Val Ile His
35 40 45

Arg Ser Ser Ala His Gln Ala Gly Val Gly Ala Ile Phe Asp Arg Val
50 55 60

Leu Ser Glu Leu Val Ala Lys Met Lys Glu Met Lys Ile Asp Lys Thr
65 70 75 80

Glu Leu Gly Cys Leu Arg Ser Ile Val Leu Phe Asn Pro Asp Ala Lys
85 90 95

Gly Leu Asn Cys Val Asn Asp Val Glu Ile Leu Arg Glu Lys Val Tyr
100 105 110

Ala Ala Leu Glu Glu Tyr Thr Arg Thr Thr Tyr Pro Asp Glu Pro Gly
115 120 125

Arg Phe Ala Lys Leu Leu Leu Arg Leu Pro Ala Leu Arg Ser Ile Gly
130 135 140

Leu Lys Cys Leu Glu Tyr Leu Phe Leu Phe Lys Leu Ile Gly Asp Thr
145 150 155 160

Pro Leu Asp Ser Tyr Leu Met Lys Met Leu Val Asp Asn Pro Asn Thr
165 170 175

Ser Val Thr Pro Pro Thr Ser
180

<210> SEQ ID NO 31
<211> LENGTH: 176
<212> TYPE: PRT
<213> ORGANISM: Tenebrio molitor

<400> SEQUENCE: 31

Ile Pro His Phe Thr Ser Leu Pro Met Ser Asp Gln Val Leu Leu Leu
1 5 10 15

Arg Ala Gly Trp Asn Glu Leu Leu Ile Ala Ala Phe Ser His Arg Ser
20 25 30

Ile Gln Ala Gln Asp Ala Ile Val Leu Ala Thr Gly Leu Thr Val Asn
35 40 45

Lys Thr Ser Ala His Ala Val Gly Val Gly Asn Ile Tyr Asp Arg Val
50 55 60

Leu Ser Glu Leu Val Asn Lys Met Lys Glu Met Lys Met Asp Lys Thr
65 70 75 80

Glu Leu Gly Cys Leu Arg Ala Ile Ile Leu Tyr Asn Pro Thr Cys Arg
85 90 95

Gly Ile Lys Ser Val Gln Glu Val Glu Met Leu Arg Glu Lys Ile Tyr
100 105 110

Gly Val Leu Glu Glu Tyr Thr Arg Thr Thr His Pro Asn Glu Pro Gly
115 120 125

Arg Phe Ala Lys Leu Leu Leu Arg Leu Pro Ala Leu Arg Ser Ile Gly
130 135 140

Leu Lys Cys Ser Glu His Leu Phe Phe Phe Lys Leu Ile Gly Asp Val
145 150 155 160

Pro Ile Asp Thr Phe Leu Met Glu Met Leu Glu Ser Pro Ala Asp Ala
165 170 175

<210> SEQ ID NO 32
<211> LENGTH: 176
<212> TYPE: PRT
<213> ORGANISM: Apis mellifera

<400> SEQUENCE: 32

Ile Pro His Phe Thr Ser Leu Pro Leu Glu Asp Gln Val Leu Leu Leu
1 5 10 15

Arg Ala Gly Trp Asn Glu Leu Leu Ile Ala Ser Phe Ser His Arg Ser
20 25 30

Ile Asp Val Lys Asp Gly Ile Val Leu Ala Thr Gly Ile Thr Val His
35 40 45

Arg Asn Ser Ala Gln Gln Ala Gly Val Gly Thr Ile Phe Asp Arg Val
50 55 60

Leu Ser Glu Leu Val Ser Lys Met Arg Glu Met Lys Met Asp Arg Thr
65 70 75 80

Glu Leu Gly Cys Leu Arg Ser Ile Ile Leu Phe Asn Pro Glu Val Arg
85 90 95

Gly Leu Lys Ser Ile Gln Glu Val Thr Leu Leu Arg Glu Lys Ile Tyr
100 105 110

Gly Ala Leu Glu Gly Tyr Cys Arg Val Ala Trp Pro Asp Asp Ala Gly
115 120 125

```
Arg Phe Ala Lys Leu Leu Leu Arg Leu Pro Ala Ile Arg Ser Ile Gly
    130                 135                 140

Leu Lys Cys Leu Glu Tyr Leu Phe Phe Phe Lys Met Ile Gly Asp Val
145                 150                 155                 160

Pro Ile Asp Asp Phe Leu Val Glu Met Leu Glu Ser Arg Ser Asp Pro
                165                 170                 175
```

<210> SEQ ID NO 33
<211> LENGTH: 441
<212> TYPE: DNA
<213> ORGANISM: Saccharomyces cerevisiae

<400> SEQUENCE: 33

```
atgaagctac tgtcttctat cgaacaagca tgcgatattt gccgacttaa aaagctcaag      60

tgctccaaag aaaaaccgaa gtgcgccaag tgtctgaaga acaactggga gtgtcgctac     120

tctcccaaaa ccaaaaggtc tccgctgact agggcacatc tgacagaagt ggaatcaagg     180

ctagaaagac tggaacagct atttctactg atttttcctc gagaagacct tgacatgatt     240

ttgaaaatgg attctttaca ggatataaaa gcattgttaa caggattatt tgtacaagat     300

aatgtgaata aagatgccgt cacagataga ttggcttcag tggagactga tatgcctcta     360

acattgagac agcatagaat aagtgcgaca tcatcatcgg aagagagtag taacaaaggt     420

caaagacagt tgactgtatc g                                              441
```

<210> SEQ ID NO 34
<211> LENGTH: 147
<212> TYPE: PRT
<213> ORGANISM: Saccharomyces cerevisiae

<400> SEQUENCE: 34

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145
```

<210> SEQ ID NO 35
<211> LENGTH: 606
<212> TYPE: DNA
<213> ORGANISM: Escherichia coli

<400> SEQUENCE: 35

```
atgaaagcgt taacggccag gcaacaagag gtgtttgatc tcatccgtga tcacatcagc     60

cagacaggta tgccgccgac gcgtgcggaa atcgcgcagc gtttggggtt ccgttcccca    120

aacgcggctg aagaacatct gaaggcgctg gcacgcaaag gcgttattga aattgtttcc    180

ggcgcatcac gcgggattcg tctgttgcag gaagaggaag aagggttgcc gctggtaggt    240

cgtgtggctg ccggtgaacc acttctggcg caacagcata ttgaaggtca ttatcaggtc    300

gatccttcct tattcaagcc gaatgctgat ttcctgctgc gcgtcagcgg gatgtcgatg    360

aaagatatcg gcattatgga tggtgacttg ctggcagtgc ataaaactca ggatgtacgt    420

aacggtcagg tcgttgtcgc acgtattgat gacgaagtta ccgttaagcg cctgaaaaaa    480

cagggcaata aagtcgaact gttgccagaa aatagcgagt ttaaaccaat tgtcgtagat    540

cttcgtcagc agagcttcac cattgaaggg ctggcggttg ggttattcg caacggcgac     600

tggctg                                                               606
```

<210> SEQ ID NO 36
<211> LENGTH: 202
<212> TYPE: PRT
<213> ORGANISM: Escherichia coli

<400> SEQUENCE: 36

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 37
<211> LENGTH: 271
<212> TYPE: DNA
<213> ORGANISM: herpes simplex virus 7

<400> SEQUENCE: 37

```
atgggcccta aaaagaagcg taaagtcgcc cccccgaccg atgtcagcct gggggacgag     60
```

```
ctccacttag acggcgagga cgtggcgatg gcgcatgccg acgcgctaga cgatttcgat    120

ctggacatgt tgggggacgg ggattccccg gggccgggat ttacccccca cgactccgcc    180

ccctacggcg ctctggatat ggccgacttc gagtttgagc agatgtttac cgatgccctt    240

ggaattgacg agtacggtgg ggaattcccg g                                   271


<210> SEQ ID NO 38
<211> LENGTH: 90
<212> TYPE: PRT
<213> ORGANISM: herpes simplex virus 7

<400> SEQUENCE: 38

Met Gly Pro Lys Lys Lys Arg Lys Val Ala Pro Pro Thr Asp Val Ser
1               5                   10                  15

Leu Gly Asp Glu Leu His Leu Asp Gly Glu Asp Val Ala Met Ala His
            20                  25                  30

Ala Asp Ala Leu Asp Asp Phe Asp Leu Asp Met Leu Gly Asp Gly Asp
        35                  40                  45

Ser Pro Gly Pro Gly Phe Thr Pro His Asp Ser Ala Pro Tyr Gly Ala
    50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90


<210> SEQ ID NO 39
<211> LENGTH: 307
<212> TYPE: DNA
<213> ORGANISM: Saccharomyces cerevisiae

<400> SEQUENCE: 39

atgggtgctc ctccaaaaaa gaagagaaag gtagctggta tcaataaaga tatcgaggag     60

tgcaatgcca tcattgagca gtttatcgac tacctgcgca ccggacagga gatgccgatg    120

gaaatggcgg atcaggcgat taacgtggtg ccgggcatga cgccgaaaac cattcttcac    180

gccgggccgc cgatccagcc tgactggctg aaatcgaatg gttttcatga aattgaagcg    240

gatgttaacg ataccagcct cttgctgagt ggagatgcct cctaccctta tgatgtgcca    300

gattatg                                                              307


<210> SEQ ID NO 40
<211> LENGTH: 102
<212> TYPE: PRT
<213> ORGANISM: Saccharomyces cerevisiae

<400> SEQUENCE: 40

Met Gly Ala Pro Pro Lys Lys Lys Arg Lys Val Ala Gly Ile Asn Lys
1               5                   10                  15

Asp Ile Glu Glu Cys Asn Ala Ile Ile Glu Gln Phe Ile Asp Tyr Leu
            20                  25                  30

Arg Thr Gly Gln Glu Met Pro Met Glu Met Ala Asp Gln Ala Ile Asn
        35                  40                  45

Val Val Pro Gly Met Thr Pro Lys Thr Ile Leu His Ala Gly Pro Pro
    50                  55                  60

Ile Gln Pro Asp Trp Leu Lys Ser Asn Gly Phe His Glu Ile Glu Ala
65                  70                  75                  80

Asp Val Asn Asp Thr Ser Leu Leu Leu Ser Gly Asp Ala Ser Tyr Pro
```

```
                85                  90                  95

Tyr Asp Val Pro Asp Tyr
            100


<210> SEQ ID NO 41
<211> LENGTH: 19
<212> TYPE: DNA
<213> ORGANISM: Artificial Sequence
<220> FEATURE:
<223> OTHER INFORMATION: GAL4 response element

<400> SEQUENCE: 41

ggagtactgt cctccgagc                                               19


<210> SEQ ID NO 42
<211> LENGTH: 36
<212> TYPE: DNA
<213> ORGANISM: Artificial Sequence
<220> FEATURE:
<223> OTHER INFORMATION: 2xLexAop response element

<400> SEQUENCE: 42

ctgctgtata taaaaccagt ggttatatgt acagta                            36


<210> SEQ ID NO 43
<211> LENGTH: 334
<212> TYPE: PRT
<213> ORGANISM: Choristoneura fumiferana

<400> SEQUENCE: 43

Pro Glu Cys Val Val Pro Glu Thr Gln Cys Ala Met Lys Arg Lys Glu
1               5                   10                  15

Lys Lys Ala Gln Lys Glu Lys Asp Lys Leu Pro Val Ser Thr Thr Thr
            20                  25                  30

Val Asp Asp His Met Pro Pro Ile Met Gln Cys Glu Pro Pro Pro Pro
        35                  40                  45

Glu Ala Ala Arg Ile His Glu Val Val Pro Arg Phe Leu Ser Asp Lys
    50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220
```

```
Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
    290                 295                 300

Lys Leu Pro Pro Phe Leu Glu Glu Ile Trp Asp Val Ala Asp Met Ser
305                 310                 315                 320

His Thr Gln Pro Pro Pro Ile Leu Glu Ser Pro Thr Asn Leu
                325                 330


<210> SEQ ID NO 44
<211> LENGTH: 549
<212> TYPE: PRT
<213> ORGANISM: Drosophila melanogaster

<400> SEQUENCE: 44

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95

Lys Leu Ile Trp Tyr Gln Asp Gly Tyr Glu Gln Pro Ser Glu Glu Asp
            100                 105                 110

Leu Arg Arg Ile Met Ser Gln Pro Asp Glu Asn Glu Ser Gln Thr Asp
        115                 120                 125

Val Ser Phe Arg His Ile Thr Glu Ile Thr Ile Leu Thr Val Gln Leu
    130                 135                 140

Ile Val Glu Phe Ala Lys Gly Leu Pro Ala Phe Thr Lys Ile Pro Gln
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
        195                 200                 205

Ala Asp Asn Ile Glu Asp Leu Leu His Phe Cys Arg Gln Met Phe Ser
    210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270
```

```
Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val His Ala Ile Pro Pro Ser Val Gln Ser His Leu Gln Ile
                325                 330                 335

Thr Gln Glu Glu Asn Glu Arg Leu Glu Arg Ala Glu Arg Met Arg Ala
            340                 345                 350

Ser Val Gly Gly Ala Ile Thr Ala Gly Ile Asp Cys Asp Ser Ala Ser
        355                 360                 365

Thr Ser Ala Ala Ala Ala Ala Ala Gln His Gln Pro Gln Pro Gln Pro
    370                 375                 380

Gln Pro Gln Pro Ser Ser Leu Thr Gln Asn Asp Ser Gln His Gln Thr
385                 390                 395                 400

Gln Pro Gln Leu Gln Pro Gln Leu Pro Pro Gln Leu Gln Gly Gln Leu
                405                 410                 415

Gln Pro Gln Leu Gln Pro Gln Leu Gln Thr Gln Leu Gln Pro Gln Ile
            420                 425                 430

Gln Pro Gln Pro Gln Leu Leu Pro Val Ser Ala Pro Val Pro Ala Ser
        435                 440                 445

Val Thr Ala Pro Gly Ser Leu Ser Ala Val Ser Thr Ser Ser Glu Tyr
    450                 455                 460

Met Gly Gly Ser Ala Ala Ile Gly Pro Ile Thr Pro Ala Thr Thr Ser
465                 470                 475                 480

Ser Ile Thr Ala Ala Val Thr Ala Ser Ser Thr Thr Ser Ala Val Pro
                485                 490                 495

Met Gly Asn Gly Val Gly Val Gly Val Gly Val Gly Gly Asn Val Ser
            500                 505                 510

Met Tyr Ala Asn Ala Gln Thr Ala Met Ala Leu Met Gly Val Ala Leu
        515                 520                 525

His Ser His Gln Glu Gln Leu Ile Gly Gly Val Ala Val Lys Ser Glu
    530                 535                 540

His Ser Thr Thr Ala
545
```

<210> SEQ ID NO 45
<211> LENGTH: 1288
<212> TYPE: DNA
<213> ORGANISM: Choristoneura fumiferana

<400> SEQUENCE: 45

```
aagggccctg cgccccgtca gcaagaggaa ctgtgtctgg tatgcgggga cagagcctcc      60

ggataccact acaatgcgct cacgtgtgaa gggtgtaaag ggttcttcag acggagtgtt     120

accaaaaatg cggtttatat ttgtaaattc ggtcacgctt gcgaaatgga catgtacatg     180

cgacggaaat gccaggagtg ccgcctgaag aagtgcttag ctgtaggcat gaggcctgag     240

tgcgtagtac ccgagactca gtgcgccatg aagcggaaag agaagaaagc acagaaggag     300

aaggacaaac tgcctgtcag cacgacgacg gtggacgacc acatgccgcc cattatgcag     360

tgtgaacctc cacctcctga agcagcaagg attcacgaag tggtcccaag gtttctctcc     420

gacaagctgt tggagacaaa ccggcagaaa aacatccccc agttgacagc caaccagcag     480
```

```
ttccttatcg ccaggctcat ctggtaccag gacgggtacg agcagccttc tgatgaagat    540

ttgaagagga ttacgcagac gtggcagcaa gcggacgatg aaaacgaaga gtctgacact    600

cccttccgcc agatcacaga gatgactatc ctcacggtcc aacttatcgt ggagttcgcg    660

aagggattgc cagggttcgc caagatctcg cagcctgatc aaattacgct gcttaaggct    720

tgctcaagtg aggtaatgat gctccgagtc gcgcgacgat acgatgcggc ctcagacagt    780

gttctgttcg cgaacaacca agcgtacact cgcgacaact accgcaaggc tggcatggcc    840

tacgtcatcg aggatctact gcacttctgc cggtgcatgt actctatggc gttggacaac    900

atccattacg cgctgctcac ggctgtcgtc atcttttctg accggccagg gttggagcag    960

ccgcaactgg tggaagaaat ccagcggtac tacctgaata cgctccgcat ctatatcctg   1020

aaccagctga gcgggtcggc gcgttcgtcc gtcatatacg gcaagatcct ctcaatcctc   1080

tctgagctac gcacgctcgg catgcaaaac tccaacatgt gcatctccct caagctcaag   1140

aacagaaagc tgccgccttt cctcgaggag atctgggatg tggcggacat gtcgcacacc   1200

caaccgccgc ctatcctcga gtcccccacg aatctctagc cctgcgcgc acgcatcgcc   1260

gatgccgcgt ccggccgcgc tgctctga                                      1288
```

<210> SEQ ID NO 46
<211> LENGTH: 309
<212> TYPE: DNA
<213> ORGANISM: Simian virus 40

<400> SEQUENCE: 46

```
ggtgtggaaa gtccccaggc tccccagcag gcagaagtat gcaaagcatg catctcaatt     60

agtcagcaac caggtgtgga aagtccccag gctccccagc aggcagaagt atgcaaagca    120

tgcatctcaa ttagtcagca accatagtcc cgcccctaac tccgcccatc ccgcccctaa    180

ctccgcccag ttccgcccat tctccgcccc atggctgact aatttttttt atttatgcag    240

aggccgaggc cgcctcggcc tctgagctat tccagaagta gtgaggaggc ttttttggag    300

gcctaggct                                                            309
```

<210> SEQ ID NO 47
<211> LENGTH: 789
<212> TYPE: DNA
<213> ORGANISM: Mus musculus

<400> SEQUENCE: 47

```
aagcgggaag ctgtgcagga ggagcggcag cggggcaagg accggaatga gaacgaggtg     60

gagtccacca gcagtgccaa cgaggacatg cctgtagaga agattctgga agccgagctt    120

gctgtcgagc ccaagactga gacatacgtg gaggcaaaca tggggctgaa ccccagctca    180

ccaaatgacc ctgttaccaa catctgtcaa gcagcagaca agcagctctt cactcttgtg    240

gagtgggcca agaggatccc acacttttct gagctgcccc tagacgacca ggtcatcctg    300

ctacgggcag gctggaacga gctgctgatc gcctccttct cccaccgctc catagctgtg    360

aaagatggga ttctcctggc caccggcctg cacgtacacc ggaacagcgc tcacagtgct    420

ggggtgggcg ccatctttga cagggtgcta acagagctgg tgtctaagat gcgtgacatg    480

cagatggaca agacggagct gggctgcctg cgagccattg tcctgttcaa ccctgactct    540

aaggggctct caaaccctgc tgaggtggag gcgttgaggg agaaggtgta tgcgtcacta    600

gaagcgtact gcaaacacaa gtaccctgag cagccgggca ggtttgccaa gctgctgctc    660

cgcctgcctg cactgcgttc catcgggctc aagtgcctgg agcacctgtt cttcttcaag    720
```

ctcatcgggg acacgcccat cgacaccttc ctcatggaga tgctggaggc accacatcaa 780
gccacctag 789

<210> SEQ ID NO 48
<211> LENGTH: 24
<212> TYPE: DNA
<213> ORGANISM: Artificial Sequence
<220> FEATURE:
<223> OTHER INFORMATION: synthetic E1b minimal promoter

<400> SEQUENCE: 48
tatataatgg atccccgggt accg 24

<210> SEQ ID NO 49
<211> LENGTH: 1653
<212> TYPE: DNA
<213> ORGANISM: Artificial Sequence
<220> FEATURE:
<223> OTHER INFORMATION: luciferase gene

<400> SEQUENCE: 49
atggaagacg ccaaaaacat aaagaaaggc ccggcgccat tctatcctct agaggatgga 60
accgctggag agcaactgca taaggctatg aagagatacg ccctggttcc tggaacaatt 120
gcttttacag atgcacatat cgaggtgaac atcacgtacg cggaatactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtt 300
gcagttgcgc ccgcgaacga catttataat gaacgtgaat tgctcaacag tatgaacatt 360
tcgcagccta ccgtagtgtt tgtttccaaa aaggggttgc aaaaaatttt gaacgtgcaa 420
aaaaaattac caataatcca gaaaattatt atcatggatt ctaaaacgga ttaccaggga 480
tttcagtcga tgtacacgtt cgtcacatct catctacctc ccggttttaa tgaatacgat 540
tttgtaccag agtcctttga tcgtgacaaa acaattgcac tgataatgaa ttcctctgga 600
tctactgggt tacctaaggg tgtggccctt ccgcatagaa ctgcctgcgt cagattctcg 660
catgccagag atcctatttt tggcaatcaa atcattccgg atactgcgat tttaagtgtt 720
gttccattcc atcacggttt tggaatgttt actacactcg gatatttgat atgtggattt 780
cgagtcgtct taatgtatag atttgaagaa gagctgtttt tacgatccct tcaggattac 840
aaaattcaaa gtgcgttgct agtaccaacc ctattttcat tcttcgccaa aagcactctg 900
attgacaaat acgatttatc taatttacac gaaattgctt ctgggggcgc acctctttcg 960
aaagaagtcg gggaagcggt tgcaaaacgc ttccatcttc cagggatacg acaaggatat 1020
gggctcactg agactacatc agctattctg attacacccg agggggatga taaaccgggc 1080
gcggtcggta aagttgttcc attttttgaa gcgaaggttg tggatctgga taccgggaaa 1140
acgctgggcg ttaatcagag aggcgaatta tgtgtcagag gacctatgat tatgtccggt 1200
tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 50
<211> LENGTH: 714
<212> TYPE: DNA
<213> ORGANISM: Mus musculus

<400> SEQUENCE: 50
gccaacgagg acatgcctgt agagaagatt ctggaagccg agcttgctgt cgagcccaag 60
actgagacat acgtggaggc aaacatgggg ctgaacccca gctcaccaaa tgaccctgtt 120
accaacatct gtcaagcagc agacaagcag ctcttcactc ttgtggagtg ggccaagagg 180
atcccacact tttctgagct gcccctagac gaccaggtca tcctgctacg ggcaggctgg 240
aacgagctgc tgatcgcctc cttctcccac cgctccatag ctgtgaaaga tgggattctc 300
ctggccaccg gcctgcacgt acaccggaac agcgctcaca gtgctggggt gggcgccatc 360
tttgacaggg tgctaacaga gctggtgtct aagatgcgtg acatgcagat ggacaagacg 420
gagctgggct gcctgcgagc cattgtcctg ttcaaccctg actctaaggg gctctcaaac 480
cctgctgagg tggaggcgtt gagggagaag gtgtatgcgt cactagaagc gtactgcaaa 540
cacaagtacc ctgagcagcc gggcaggttt gccaagctgc tgctccgcct gcctgcactg 600
cgttccatcg ggctcaagtg cctggagcac ctgttcttct tcaagctcat cggggacacg 660
cccatcgaca ccttcctcat ggagatgctg gaggcaccac atcaagccac ctag 714

<210> SEQ ID NO 51
<211> LENGTH: 867
<212> TYPE: DNA
<213> ORGANISM: Choristoneura fumiferana

<400> SEQUENCE: 51
aagcgagagg cggtgcaaga ggagcgccag aggaatgctc gcggcgcgga ggatgcgcac 60
ccgagtagct cggtgcaggt aagcgatgag ctgtcaatcg agcgcctaac ggagatggag 120
tctttggtgg cagatcccag cgaggagttc cagttcctcc gcgtggggcc tgacagcaac 180
gtgcctccac gttaccgcgc gcccgtctcc tccctctgcc aaataggcaa caagcaaata 240
gcggcgttgg tggtatgggc gcgcgacatc cctcatttcg ggcagctgga gctggacgat 300
caagtggtac tcatcaaggc ctcctggaat gagctgctac tcttcgccat cgcctggcgc 360
tctatggagt atttggaaga tgagagggag aacggggacg gaacgcggag caccactcag 420
ccacaactga tgtgtctcat gcctggcatg acgttgcacc gcaactcggc gcagcaggcg 480
ggcgtgggcg ccatcttcga ccgcgtgctg tccgagctca gtctgaagat gcgcaccttg 540
cgcatggacc aggccgagta cgtcgcgctc aaagccatcg tgctgctcaa ccctgatgtg 600
aaaggactga agaatcggca agaagttgac gttttgcgag aaaaaatgtt ctcttgcctg 660
gacgactact gccggcggtc gcgaagcaac gaggaaggcc ggtttgcgtc cttgctgctg 720
cggctgccag ctctccgctc catctcgctc aagagcttcg aacacctcta cttcttccac 780
ctcgtggccg aaggctccat cagcggatac atacgagagg cgctccgaaa ccacgcgcct 840
ccgatcgacg tcaatgccat gatgtaa 867

<210> SEQ ID NO 52
<211> LENGTH: 711
<212> TYPE: DNA
<213> ORGANISM: Locusta migratoria

<400> SEQUENCE: 52
aagagagaag cagttcagga ggaaaggcag cgaacaaagg agcgtgatca gaatgaagtt 60
gaatcaacaa gcagcctgca tacagacatg cctgttgaac gcatacttga agctgaaaaa 120
cgagtggagt gcaaagcaga aaaccaagtg gaatatgagc tggtggagtg ggctaaacac 180
atcccgcact tcacatccct acctctggag gaccaggttc tcctcctcag agcaggttgg 240
aatgaactgc taattgcagc attttcacat cgatctgtag atgttaaaga tggcatagta 300
cttgccactg gtctcacagt gcatcgaaat tctgcccatc aagctggagt cggcacaata 360
tttgacagag ttttgacaga actggtagca aagatgagag aaatgaaaat ggataaaact 420
gaacttggct gcttgcgatc tgttattctt ttcaatccag aggtgagggg tttgaaatcc 480
gcccaggaag ttgaacttct acgtgaaaaa gtatatgccg ctttggaaga atatactaga 540
acaacacatc ccgatgaacc aggaagattt gcaaaacttt tgcttcgtct gccttcttta 600
cgttccatag gccttaagtg tttggagcat ttgtttttct ttcgccttat tggagatgtt 660
ccaattgata cgttcctgat ggagatgctt gaatcacctt ctgattcata a 711

<210> SEQ ID NO 53
<211> LENGTH: 1054
<212> TYPE: DNA
<213> ORGANISM: Choristoneura fumiferana

<400> SEQUENCE: 53
cctgagtgcg tagtacccga gactcagtgc gccatgaagc ggaaagagaa gaaagcacag 60
aaggagaagg acaaactgcc tgtcagcacg acgacggtgg acgaccacat gccgcccatt 120
atgcagtgtg aacctccacc tcctgaagca gcaaggattc acgaagtggt cccaaggttt 180
ctctccgaca agctgttgga gacaaaccgg cagaaaaaca tcccccagtt gacagccaac 240
cagcagttcc ttatcgccag gctcatctgg taccaggacg ggtacgagca gccttctgat 300
gaagatttga agaggattac gcagacgtgg cagcaagcgg acgatgaaaa cgaagagtct 360
gacactccct tccgccagat cacagagatg actatcctca cggtccaact tatcgtggag 420
ttcgcgaagg gattgccagg gttcgccaag atctcgcagc ctgatcaaat tacgctgctt 480
aaggcttgct caagtgaggt aatgatgctc cgagtcgcgc gacgatacga tgcggcctca 540
gacagtgttc tgttcgcgaa caaccaagcg tacactcgcg acaactaccg caaggctggc 600
atggcctacg tcatcgagga tctactgcac ttctgccggt gcatgtactc tatggcgttg 660
gacaacatcc attacgcgct gctcacggct gtcgtcatct tttctgaccg gccagggttg 720
gagcagccgc aactggtgga agaaatccag cggtactacc tgaatacgct ccgcatctat 780
atcctgaacc agctgagcgg gtcggcgcgt tcgtccgtca tatacggcaa gatcctctca 840
atcctctctg agctacgcac gctcggcatg caaaactcca acatgtgcat ctccctcaag 900
ctcaagaaca gaaagctgcc gcctttcctc gaggagatct gggatgtggc ggacatgtcg 960
cacacccaac cgccgcctat cctcgagtcc cccacgaatc tctagcccct gcgcgcacgc 1020
atcgccgatg ccgcgtccgg ccgcgctgct ctga 1054

<210> SEQ ID NO 54
<211> LENGTH: 1542
<212> TYPE: DNA
<213> ORGANISM: Choristoneura fumiferana

<400> SEQUENCE: 54

-continued

```
ctggacctga aacacgaagt ggcttaccga ggggtgctcc caggccaggt gaaggccgaa      60
ccgggggtcc acaacggcca ggtcaacggc cacgtgaggg actggatggc aggcggcgct     120
ggtgccaatt cgccgtctcc gggagcggtg gctcaacccc agcctaacaa tgggtattcg     180
tcgccactct cctcgggaag ctacgggccc tacagtccaa atgggaaaat aggccgtgag     240
gaactgtcgc cagcttcaag tataaatggg tgcagtacag atggcgaggc acgacgtcag     300
aagaagggcc ctgcgccccg tcagcaagag gaactgtgtc tggtatgcgg ggacagagcc     360
tccggatacc actacaatgc gctcacgtgt gaagggtgta aagggttctt cagacggagt     420
gttaccaaaa atgcggttta tatttgtaaa ttcggtcacg cttgcgaaat ggacatgtac     480
atgcgacgga aatgccagga gtgccgcctg aagaagtgct tagctgtagg catgaggcct     540
gagtgcgtag tacccgagac tcagtgcgcc atgaagcgga aagagaagaa agcacagaag     600
gagaaggaca aactgcctgt cagcacgacg acggtggacg accacatgcc gcccattatg     660
cagtgtgaac ctccacctcc tgaagcagca aggattcacg aagtggtccc aaggtttctc     720
tccgacaagc tgttggagac aaaccggcag aaaaacatcc cccagttgac agccaaccag     780
cagttcctta tcgccaggct catctggtac caggacgggt acgagcagcc ttctgatgaa     840
gatttgaaga ggattacgca gacgtggcag caagcggacg atgaaaacga agagtctgac     900
actcccttcc gccagatcac agagatgact atcctcacgg tccaacttat cgtggagttc     960
gcgaagggat tgccagggtt cgccaagatc tcgcagcctg atcaaattac gctgcttaag    1020
gcttgctcaa gtgaggtaat gatgctccga gtcgcgcgac gatacgatgc ggcctcagac    1080
agtgttctgt tcgcgaacaa ccaagcgtac actcgcgaca actaccgcaa ggctggcatg    1140
gcctacgtca tcgaggatct actgcacttc tgccggtgca tgtactctat ggcgttggac    1200
aacatccatt acgcgctgct cacggctgtc gtcatctttt ctgaccggcc agggttggag    1260
cagccgcaac tggtggaaga aatccagcgg tactacctga atacgctccg catctatatc    1320
ctgaaccagc tgagcgggtc ggcgcgttcg tccgtcatat acggcaagat cctctcaatc    1380
ctctctgagc tacgcacgct cggcatgcaa aactccaaca tgtgcatctc cctcaagctc    1440
aagaacagaa agctgccgcc tttcctcgag gagatctggg atgtggcgga catgtcgcac    1500
acccaaccgc cgcctatcct cgagtccccc acgaatctct ag                       1542
```

<210> SEQ ID NO 55
<211> LENGTH: 1110
<212> TYPE: DNA
<213> ORGANISM: Choristoneura fumiferana

<400> SEQUENCE: 55

```
gcggtttata tttgtaaatt cggtcacgct tgcgaaatgg acatgtacat gcgacggaaa      60
tgccaggagt gccgcctgaa gaagtgctta gctgtaggca tgaggcctga gtgcgtagta     120
cccgagactc agtgcgccat gaagcggaaa gagaagaaag cacagaagga gaaggacaaa     180
ctgcctgtca gcacgacgac ggtggacgac cacatgccgc ccattatgca gtgtgaacct     240
ccacctcctg aagcagcaag gattcacgaa gtggtcccaa ggtttctctc cgacaagctg     300
ttggagacaa accggcagaa aaacatcccc cagttgacag ccaaccagca gttccttatc     360
gccaggctca tctggtacca ggacgggtac gagcagcctt ctgatgaaga tttgaagagg     420
attacgcaga cgtggcagca agcggacgat gaaaacgaag agtctgacac tcccttccgc     480
cagatcacag agatgactat cctcacggtc caacttatcg tggagttcgc gaagggattg     540
ccagggttcg ccaagatctc gcagcctgat caaattacgc tgcttaaggc ttgctcaagt     600
```

gaggtaatga tgctccgagt cgcgcgacga tacgatgcgg cctcagacag tgttctgttc 660
gcgaacaacc aagcgtacac tcgcgacaac taccgcaagg ctggcatggc ctacgtcatc 720
gaggatctac tgcacttctg ccggtgcatg tactctatgg cgttggacaa catccattac 780
gcgctgctca cggctgtcgt catcttttct gaccggccag ggttggagca gccgcaactg 840
gtggaagaaa tccagcggta ctacctgaat acgctccgca tctatatcct gaaccagctg 900
agcgggtcgg cgcgttcgtc cgtcatatac ggcaagatcc tctcaatcct ctctgagcta 960
cgcacgctcg gcatgcaaaa ctccaacatg tgcatctccc tcaagctcaa gaacagaaag 1020
ctgccgcctt tcctcgagga gatctgggat gtggcggaca tgtcgcacac ccaaccgccg 1080
cctatcctcg agtcccccac gaatctctag 1110

<210> SEQ ID NO 56
<211> LENGTH: 798
<212> TYPE: DNA
<213> ORGANISM: Choristoneura fumiferana

<400> SEQUENCE: 56
tcggtgcagg taagcgatga gctgtcaatc gagcgcctaa cggagatgga gtctttggtg 60
gcagatccca gcgaggagtt ccagttcctc cgcgtggggc ctgacagcaa cgtgcctcca 120
cgttaccgcg cgcccgtctc ctccctctgc caaataggca acaagcaaat agcggcgttg 180
gtggtatggg cgcgcgacat ccctcatttc gggcagctgg agctggacga tcaagtggta 240
ctcatcaagg cctcctggaa tgagctgcta ctcttcgcca tcgcctggcg ctctatggag 300
tatttggaag atgagaggga gaacggggac ggaacgcgga gcaccactca gccacaactg 360
atgtgtctca tgcctggcat gacgttgcac cgcaactcgg cgcagcaggc gggcgtgggc 420
gccatcttcg accgcgtgct gtccgagctc agtctgaaga tgcgcacctt gcgcatggac 480
caggccgagt acgtcgcgct caaagccatc gtgctgctca accctgatgt gaaaggactg 540
aagaatcggc aagaagttga cgttttgcga gaaaaaatgt tctcttgcct ggacgactac 600
tgccggcggt cgcgaagcaa cgaggaaggc cggtttgcgt ccttgctgct gcggctgcca 660
gctctccgct ccatctcgct caagagcttc gaacacctct acttcttcca cctcgtggcc 720
gaaggctcca tcagcggata catacgagag gcgctccgaa accacgcgcc tccgatcgac 780
gtcaatgcca tgatgtaa 798

<210> SEQ ID NO 57
<211> LENGTH: 1586
<212> TYPE: DNA
<213> ORGANISM: Bamecia argentifoli

<400> SEQUENCE: 57
gaattcgcgg ccgctcgcaa acttccgtac ctctcacccc ctcgccagga ccccccgcca 60
accagttcac cgtcatctcc tccaatggat actcatcccc catgtcttcg ggcagctacg 120
acccttatag tcccaccaat ggaagaatag ggaaagaaga gctttcgccg gcgaatagtc 180
tgaacgggta caacgtggat agctgcgatg cgtcgcggaa gaagaaggga ggaacgggtc 240
ggcagcagga ggagctgtgt ctcgtctgcg gggaccgcgc ctccggctac cactacaacg 300
ccctcacctg cgaaggctgc aagggcttct tccgtcggag catcaccaag aatgccgtct 360
accagtgtaa atatggaaat aattgtgaaa ttgacatgta catgaggcga aaatgccaag 420
agtgtcgtct caagaagtgt ctcagcgttg gcatgaggcc agaatgtgta gttcccgaat 480

```
tccagtgtgc tgtgaagcga aaagagaaaa aagcgcaaaa ggacaaagat aaacctaact    540
caacgacgag ttgttctcca gatggaatca aacaagagat agatcctcaa aggctggata    600
cagattcgca gctattgtct gtaaatggag ttaaacccat tactccagag caagaagagc    660
tcatccatag gctagtttat tttcaaaatg aatatgaaca tccatcccca gaggatatca    720
aaaggatagt taatgctgca ccagaagaag aaaatgtagc tgaagaaagg tttaggcata    780
ttacagaaat tacaattctc actgtacagt taattgtgga attttctaag cgattacctg    840
gttttgacaa actaattcgt gaagatcaaa tagctttatt aaaggcatgt agtagtgaag    900
taatgatgtt tagaatggca aggaggtatg atgctgaaac agattcgata ttgtttgcaa    960
ctaaccagcc gtatacgaga gaatcataca ctgtagctgg catgggtgat actgtggagg   1020
atctgctccg attttgtcga catatgtgtg ccatgaaagt cgataacgca gaatatgctc   1080
ttctcactgc cattgtaatt ttttcagaac gaccatctct aagtgaaggc tggaaggttg   1140
agaagattca agaaatttac atagaagcat taaaagcata tgttgaaaat cgaaggaaac   1200
catatgcaac aaccattttt gctaagttac tatctgtttt aactgaacta cgaacattag   1260
ggaatatgaa ttcagaaaca tgcttctcat tgaagctgaa gaatagaaag gtgccatcct   1320
tcctcgagga gatttgggat gttgtttcat aaacagtctt acctcaattc catgttactt   1380
ttcatatttg atttatctca gcaggtggct cagtacttat cctcacatta ctgagctcac   1440
ggtatgctca tacaattata acttgtaata tcatatcggt gatgacaaat ttgttacaat   1500
attctttgtt accttaacac aatgttgatc tcataatgat gtatgaattt ttctgttttt   1560
gcaaaaaaaa aagcggccgc gaattc                                        1586
```

<210> SEQ ID NO 58
<211> LENGTH: 1109
<212> TYPE: DNA
<213> ORGANISM: Nephotetix cincticeps

<400> SEQUENCE: 58

```
caggaggagc tctgcctgtt gtgcggagac cgagcgtcgg gataccacta caacgctctc     60
acctgcgaag gatgcaaggg cttctttcgg aggagtatca ccaaaaacgc agtgtaccag    120
tccaaatacg gcaccaattg tgaaatagac atgtatatgc ggcgcaagtg ccaggagtgc    180
cgactcaaga agtgcctcag tgtagggatg aggccagaat gtgtagtacc tgagtatcaa    240
tgtgccgtaa aaaggaaaga gaaaaaagct caaaaggaca aagataaacc tgtctcttca    300
accaatggct cgcctgaaat gagaatagac caggacaacc gttgtgtggt gttgcagagt    360
gaagacaaca ggtacaactc gagtacgccc agtttcggag tcaaacccct cagtccagaa    420
caagaggagc tcatccacag gctcgtctac ttccagaacg agtacgaaca ccctgccgag    480
gaggatctca agcggatcga gaacctcccc tgtgacgacg atgacccgtg tgatgttcgc    540
tacaaacaca ttacggagat cacaatactc acagtccagc tcatcgtgga gtttgcgaaa    600
aaactgcctg gtttcgacaa actactgaga gaggaccaga tcgtgttgct caaggcgtgt    660
tcgagcgagg tgatgatgct gcggatggcg cggaggtacg acgtccagac agactcgatc    720
ctgttcgcca acaaccagcc gtacacgcga gagtcgtaca cgatggcagg cgtgggggaa    780
gtcatcgaag atctgctgcg gttcggccga ctcatgtgct ccatgaaggt ggacaatgcc    840
gagtatgctc tgctcacggc catcgtcatc ttctccgagc ggccgaacct ggcggaagga    900
tggaaggttg agaagatcca ggagatctac ctggaggcgc tcaagtccta cgtggacaac    960
cgagtgaaac ctcgcagtcc gaccatcttc gccaaactgc tctccgttct caccgagctg   1020
```

```
cgaacactcg gcaaccagaa ctccgagatg tgcttctcgt taaactacgc aaccgcaaac   1080

atgccaccgt tcctcgaaga aatctggga                                     1109


<210> SEQ ID NO 59
<211> LENGTH: 401
<212> TYPE: PRT
<213> ORGANISM: Choristoneura fumiferana

<400> SEQUENCE: 59

Cys Leu Val Cys Gly Asp Arg Ala Ser Gly Tyr His Tyr Asn Ala Leu
1               5                   10                  15

Thr Cys Glu Gly Cys Lys Gly Phe Phe Arg Arg Ser Val Thr Lys Asn
            20                  25                  30

Ala Val Tyr Ile Cys Lys Phe Gly His Ala Cys Glu Met Asp Met Tyr
        35                  40                  45

Met Arg Arg Lys Cys Gln Glu Cys Arg Leu Lys Lys Cys Leu Ala Val
    50                  55                  60

Gly Met Arg Pro Glu Cys Val Val Pro Glu Thr Gln Cys Ala Met Lys
65                  70                  75                  80

Arg Lys Glu Lys Lys Ala Gln Lys Glu Lys Asp Lys Leu Pro Val Ser
                85                  90                  95

Thr Thr Thr Val Asp Asp His Met Pro Pro Ile Met Gln Cys Glu Pro
            100                 105                 110

Pro Pro Pro Glu Ala Ala Arg Ile His Glu Val Val Pro Arg Phe Leu
        115                 120                 125

Ser Asp Lys Leu Leu Glu Thr Asn Arg Gln Lys Asn Ile Pro Gln Leu
    130                 135                 140

Thr Ala Asn Gln Gln Phe Leu Ile Ala Arg Leu Ile Trp Tyr Gln Asp
145                 150                 155                 160

Gly Tyr Glu Gln Pro Ser Asp Glu Asp Leu Lys Arg Ile Thr Gln Thr
                165                 170                 175

Trp Gln Gln Ala Asp Asp Glu Asn Glu Glu Ser Asp Thr Pro Phe Arg
            180                 185                 190

Gln Ile Thr Glu Met Thr Ile Leu Thr Val Gln Leu Ile Val Glu Phe
        195                 200                 205

Ala Lys Gly Leu Pro Gly Phe Ala Lys Ile Ser Gln Pro Asp Gln Ile
    210                 215                 220

Thr Leu Leu Lys Ala Cys Ser Ser Glu Val Met Met Leu Arg Val Ala
225                 230                 235                 240

Arg Arg Tyr Asp Ala Ala Ser Asp Ser Val Leu Phe Ala Asn Asn Gln
                245                 250                 255

Ala Tyr Thr Arg Asp Asn Tyr Arg Lys Ala Gly Met Ala Tyr Val Ile
            260                 265                 270

Glu Asp Leu Leu His Phe Cys Arg Cys Met Tyr Ser Met Ala Leu Asp
        275                 280                 285

Asn Ile His Tyr Ala Leu Leu Thr Ala Val Val Ile Phe Ser Asp Arg
    290                 295                 300

Pro Gly Leu Glu Gln Pro Gln Leu Val Glu Glu Ile Gln Arg Tyr Tyr
305                 310                 315                 320

Leu Asn Thr Leu Arg Ile Tyr Ile Leu Asn Gln Leu Ser Gly Ser Ala
                325                 330                 335

Arg Ser Ser Val Ile Tyr Gly Lys Ile Leu Ser Ile Leu Ser Glu Leu
            340                 345                 350
```

-continued

```
Arg Thr Leu Gly Met Gln Asn Ser Asn Met Cys Ile Ser Leu Lys Leu
        355                 360                 365

Lys Asn Arg Lys Leu Pro Pro Phe Leu Glu Glu Ile Trp Asp Val Ala
    370                 375                 380

Asp Met Ser His Thr Gln Pro Pro Pro Ile Leu Glu Ser Pro Thr Asn
385                 390                 395                 400

Leu


<210> SEQ ID NO 60
<211> LENGTH: 825
<212> TYPE: DNA
<213> ORGANISM: Drosophila melanogaster

<400> SEQUENCE: 60

gtgtccaggg atttctcgat cgagcgcatc atagaggccg agcagcgagc ggagacccaa      60

tgcggcgatc gtgcactgac gttcctgcgc gttggtccct attccacagt ccagccggac     120

tacaagggtg ccgtgtcggc cctgtgccaa gtggtcaaca aacagctctt ccagatggtc     180

gaatacgcgc gcatgatgcc gcactttgcc caggtgccgc tggacgacca ggtgattctg     240

ctgaaagccg cttggatcga gctgctcatt gcgaacgtgg cctggtgcag catcgtttcg     300

ctggatgacg gcggtgccgg cggcgggggc ggtggactag gccacgatgg ctcctttgag     360

cgacgatcac cgggccttca gccccagcag ctgttcctca accagagctt ctcgtaccat     420

cgcaacagtg cgatcaaagc cggtgtgtca gccatcttcg accgcatatt gtcggagctg     480

agtgtaaaga tgaagcggct gaatctcgac cgacgcgagc tgtcctgctt gaaggccatc     540

atactgtaca acccggacat acgcgggatc aagagccggg cggagatcga gatgtgccgc     600

gagaaggtgt acgcttgcct ggacgagcac tgccgcctgg aacatccggg cgacgatgga     660

cgctttgcgc aactgctgct gcgtctgccc gctttgcgat cgatcagcct gaagtgccag     720

gatcacctgt tcctcttccg cattaccagc gaccggccgc tggaggagct ctttctcgag     780

cagctggagg cgccgccgcc acccggcctg gcgatgaaac tggag                     825
```